(12) United States Patent
Ruddy et al.

(10) Patent No.: US 12,180,130 B2
(45) Date of Patent: Dec. 31, 2024

(54) METHODS, SYSTEMS, AND CATALYSTS FOR THE DIRECT CONVERSION OF SYNGAS TO HIGH-OCTANE HYDROCARBONS

(71) Applicant: Alliance for Sustainable Energy, LLC, Golden, CO (US)

(72) Inventors: Daniel Ruddy, Arvada, CO (US); Jesse Evan Hensley, Arvada, CO (US); Joshua A. Schaidle, Arvada, CO (US); Connor Patrick Nash, Lakewood, CO (US); Anh The To, Denver, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 17/401,778

(22) Filed: Aug. 13, 2021

(65) Prior Publication Data
US 2022/0048834 A1 Feb. 17, 2022

Related U.S. Application Data

(60) Provisional application No. 63/065,648, filed on Aug. 14, 2020.

(51) Int. Cl.
*C07C 1/22* (2006.01)
*B01J 8/04* (2006.01)
(Continued)

(52) U.S. Cl.
CPC ............... *C07C 1/22* (2013.01); *B01J 8/04* (2013.01); *B01J 21/04* (2013.01); *B01J 21/066* (2013.01);
(Continued)

(58) Field of Classification Search
None
See application file for complete search history.

(56) References Cited

U.S. PATENT DOCUMENTS

2012/0022306 A1* 1/2012 Corradini ............. C10L 1/04
585/24
2015/0247100 A1* 9/2015 Bradin ............... C10G 3/49
585/254
(Continued)

FOREIGN PATENT DOCUMENTS

WO 2017155424 A1 9/2017

OTHER PUBLICATIONS

Ahn et al., "Selective homologation routes to 2,2,3-trimethylbutane on solid acids", Angewandte Chemie—International Edition, May 2009, vol. 48, No. 21, pp. 3814-3816.
(Continued)

*Primary Examiner* — In Suk C Bullock
*Assistant Examiner* — Alyssa L Cepluch
(74) *Attorney, Agent, or Firm* — Neal S. Vickery; Michael A. McIntyre

(57) ABSTRACT

The present disclosure relates to a method that includes converting a gas stream that contains hydrogen ($H_2$) and carbon monoxide (CO) to a second mixture that contains a hydrocarbon, for example, a hydrocarbon having between 3 and 15 carbon atoms, where the converting is performed using a first catalyst configured to convert $H_2$ and CO to methanol, a second catalyst configured to convert methanol to dimethyl ether (DME), and a third catalyst configured to convert DME to the hydrocarbon.

7 Claims, 41 Drawing Sheets

(51) Int. Cl.
- *B01J 21/04* (2006.01)
- *B01J 21/06* (2006.01)
- *B01J 21/08* (2006.01)
- *B01J 23/72* (2006.01)
- *B01J 23/80* (2006.01)
- *B01J 29/70* (2006.01)
- *B01J 35/00* (2024.01)
- *C07C 29/154* (2006.01)
- *C07C 41/09* (2006.01)

(52) U.S. Cl.
CPC ............... *B01J 21/08* (2013.01); *B01J 23/72* (2013.01); *B01J 23/80* (2013.01); *B01J 29/7007* (2013.01); *B01J 35/19* (2024.01); *C07C 29/154* (2013.01); *C07C 41/09* (2013.01); *B01J 2208/025* (2013.01); *B01J 2208/027* (2013.01); *C07C 2521/04* (2013.01); *C07C 2521/06* (2013.01); *C07C 2521/08* (2013.01); *C07C 2523/06* (2013.01); *C07C 2523/72* (2013.01)

(56) References Cited

U.S. PATENT DOCUMENTS

2015/0353840 A1* 12/2015 Hensley .............. C07C 29/1518 502/61
2020/0231525 A1* 7/2020 Dakka ..................... C07C 41/01

OTHER PUBLICATIONS

Dupuis et al., "High-Octane Gasoline from Biomass: Experimental, Economic, and Environmental Assessment", Applied Energy, May 2019, vol. 241, pp. 25-33.

Farberow et al., "Exploring Low-Temperature Dehydrogenation at Ionic Cu Sites in Beta Zeolite", ACS Catalysis, 2017, vol. 7, pp. 3662-3667.

Meshcheryakov et al., "Thermodynamic equilibrium in the synthesis of dimethyl ether from synthesis gas", Theoretical Foundations of Chemical Engineering, 2000, vol. 34, No. 1, pp. 85-89.

Pisarenko et al., "Intensification of Natural Gas Conversion to the Key Products of Petrochemical Synthesis and Engine Fuels", Theoretical Foundations of Chemical Engineering, 2009, vol. 43, No. 5, pp. 617-628.

Ruddy et al., "Methanol to high-octane gasoline within a market-responsive biorefinery concept enabled by catalysis", Nature Catalysis, Jul. 2019, vol. 2, pp. 632-640.

Schaidle et al., "Conversion of dimethyl ether to 2,2,3-trimethylbutane over a Cu/BEA catalyst: Role of Cu sites in hydrogen incorporation", ACS Catalysis, 2015, vol. 5, No. 3, pp. 1794-1803.

Tan et al., "Conceptual process design and economics for the production of high-octane gasoline blendstock via indirect liquefaction of biomass through methanol/dimethyl ether intermediates", Biofuels Bio Products & Biorefining, 2016, vol. 10, No. 1, pp. 17-35.

Tan et al., "High-Octane Gasoline from Lignocellulosic Biomass via Syngas and Methanol/Dimethyl Ether Intermediates: 2018 State of Technology and Future Research", 2018, National Renewable Energy Laboratory Technical Report No. NREL/TP-5100-71957, Nov. 2018, patges 1-42.

Tan et al., "High-Octane Gasoline from Lignocellulosic Biomass via Syngas and Methanol/Dimethyl Ether Intermediates: 2019 State of Technology", National Renewable Energy Laboratory Technical Report No., NREL/TP-5100-76619, Apr. 2020, pp. 1-33.

Zhou et al., "New horizon in C1 chemistry: breaking the selectivity limitation in transformation of syngas and hydrogenation of CO2 into hydrocarbon chemicals and fuels", Chemical Society Reviews, 2019, vol. 48, pp. 3193-3228.

* cited by examiner

METHODS, SYSTEMS, AND CATALYSTS FOR THE DIRECT CONVERSION OF SYNGAS TO HIGH-OCTANE HYDROCARBONS

CROSS-REFERENCE TO RELATED APPLICATIONS

This application claims priority from U.S. Provisional Patent Application No. 63/065,648 filed on Aug. 14, 2020, the contents of which are incorporated herein by reference in its entirety.

CONTRACTUAL ORIGIN

This invention was made with government support under Contract No. DE-AC36-08GO28308 awarded by the Department of Energy. The government has certain rights in the invention.

BACKGROUND

The typical approach for biomass- or waste-derived syngas to high-octane gasoline (HOG) involves three steps at slightly different operating conditions: syngas-to-methanol, methanol-to-dimethyl ether (DME), and DME-to-HOG. Incumbent technologies typically utilize three reactors, one for each of these three reactions. Among other things, a three-reactor system can lead to process complexity and higher construction costs and operating costs.

Further, carbon dioxide ($CO_2$) is a by-product of the gasification reaction that is typically removed from the process during the syngas clean-up step, limiting the overall carbon efficiency and fuel product yield. The conversion of $CO_2$ with syngas into the hydrocarbon product would improve the overall carbon efficiency, reduce $CO_2$ emissions, and improve the process economics. Thus, there remains a need for improved catalysts, systems, and methods that enable process simplification and improved conversion of syngas to HOG and other useful hydrocarbons.

SUMMARY

An aspect of the present disclosure is a method that includes converting a gas stream that contains hydrogen ($H_2$) and carbon monoxide (CO) to a second mixture that contains a hydrocarbon, for example, a hydrocarbon having between 3 and 15 carbon atoms, where the converting is performed using a first catalyst configured to convert $H_2$ and CO to methanol, a second catalyst configured to convert methanol to dimethyl ether (DME), and a third catalyst configured to convert DME to the hydrocarbon.

In some embodiments of the present disclosure, the first catalyst may include copper and a zinc oxide. In some embodiments of the present disclosure, the first catalyst may further include at least one of silica, alumina, zirconia, and/or ceria. In some embodiments of the present disclosure, the second catalyst may include at least one of an alumina and/or silica. In some embodiments of the present disclosure, the third catalyst may include at least one of copper and/or a zeolite. In some embodiments of the present disclosure, the zeolite may include a beta zeolite having a silica to alumina ratio between about 20:1 and about 300:1.

In some embodiments of the present disclosure, the copper in the third catalyst may be present at a concentration between about 1 wt % and about 20 wt %, relative to the total weight of the third catalyst. In some embodiments of the present disclosure, the first catalyst and the second catalyst may be present at a ratio between about 1:1 and about 8:1. In some embodiments of the present disclosure, the second catalyst and the third catalyst may be present at a ratio between about 1:1 and about 5:2. In some embodiments of the present disclosure, the first catalyst, the second catalyst, and the third catalyst may be contained in a single reactor. In some embodiments of the present disclosure, the single reactor may be a packed bed.

As described herein, a single packed bed reactor may be provided in a stacked configuration of two or more catalysts, where each catalyst occupies a distinct position or space within the reactor, and where their positions are static in position (e.g., don't move in space). Each individual catalyst's position or space within the reactor can also be visualized as a zone within a reactor. As described herein, these zones may be static. However, in some embodiments of the present disclosure, one or more zones may be dynamic, e.g., capable of moving relative to a fixed reference point. For example, a catalyst may be positioned within a dynamically moving zone, as would be the case in a moving bed reactor or "donut" reactor.

In some embodiments of the present disclosure, the first catalyst may be positioned in the packed bed in a first layer, the second catalyst may be positioned in the packed bed in a second layer, the third catalyst may be positioned in the packed bed in a third layer, and the second layer may be positioned in series between the first layer and the third layer. In some embodiments of the present disclosure, the first catalyst and the second catalyst may be positioned in the packed bed as a well-mixed mixture in a first layer, the third catalyst may be positioned in the packed bed in a second layer, and the first layer and the second layer may be positioned in series. In some embodiments of the present disclosure, the first catalyst, the second catalyst, and the third catalyst may be positioned in the packed bed as a well-mixed mixture in a single layer.

In some embodiments of the present disclosure, the first catalyst may be positioned in the packed bed in a first layer, the second catalyst and the third catalyst may be positioned in the packed bed as a well-mixed mixture in a second layer, and the first layer and the second layer may be positioned in series. In some embodiments of the present disclosure, the first catalyst and the second catalyst may be positioned in a first reactor, the third catalyst may be positioned in a second reactor, and the first reactor and the second reactor are positioned in series. In some embodiments of the present disclosure, the first catalyst and second catalyst may be positioned in a packed bed as a well-mixed mixture.

In some embodiments, the gas stream may further comprise carbon dioxide ($CO_2$), which is also converted to at least one hydrocarbon. The carbon dioxide may be provided at a mol % greater or equal to 1%, 2%, 5%, 10%, or optionally, 20%. The carbon dioxide may be present in the initial feedstock, for example as a biproduct of syngas generation or as a recycled by product from the methods and processes described herein, or both.

An aspect of the present disclosure is a composition that includes a first portion containing copper and a zinc oxide, a second portion containing at least one of an alumina and/or silica, and a third portion containing a zeolite. In some embodiments of the present disclosure, the first portion may be in a first layer, the second layer may be in a second layer, the third layer may be in a third layer, and the second layer may be positioned between the first layer and the third layer.

An aspect of the present disclosure is a system that includes at least one of a first reactor and/or a second reactor, where at least one of the first reactor and/or the second reactor contains a catalyst or composition as described herein.

REFERENCE NUMERALS

Figure 1:
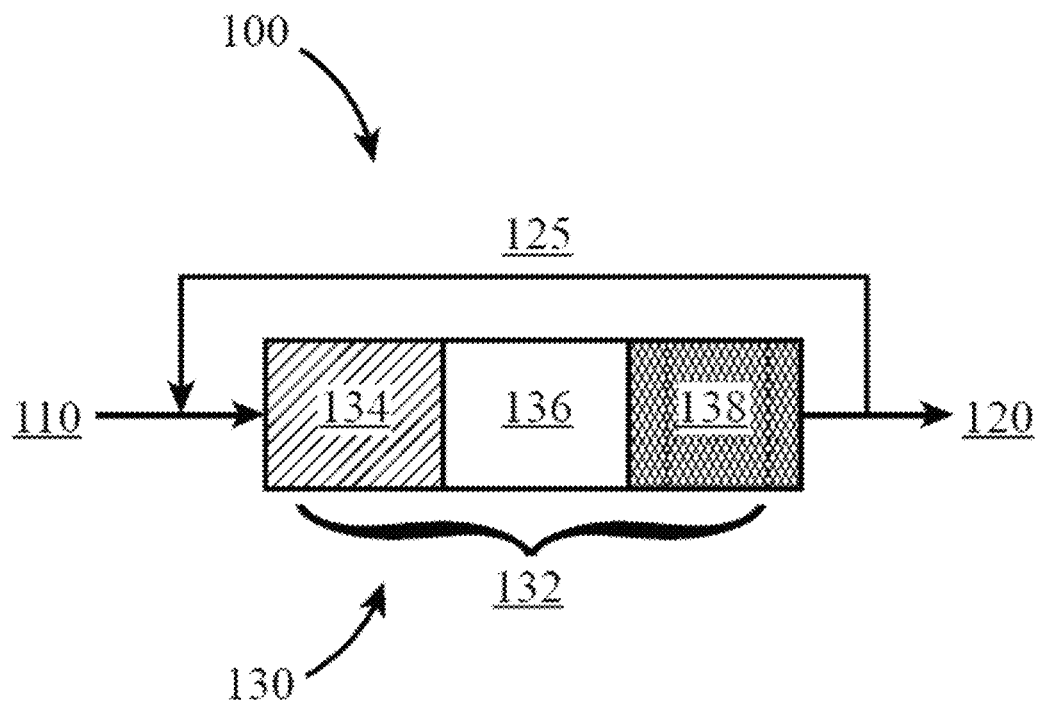
FIG. 1 illustrates a system for converting a feed stream containing at least one of syngas, CO, and/or $CO_2$ to a product stream containing a high-octane gasoline (HOG), according to some embodiments of the present disclosure.

| | |
|---|---|
| 100 | system |
| 110 | feed stream |
| 120 | product stream |
| 125 | recycle stream |
| 130 | packed bed reactor |
| 132 | catalyst bed |
| 134 | first catalyst layer |
| 136 | second catalyst layer |
| 138 | third catalyst layer |

DETAILED DESCRIPTION

The embodiments described herein should not necessarily be construed as limited to addressing any of the particular problems or deficiencies discussed herein. References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein the term "substantially" is used to indicate that exact values are not necessarily attainable. By way of example, one of ordinary skill in the art will understand that in some chemical reactions 100% conversion of a reactant is possible, yet unlikely. Most of a reactant may be converted to a product and conversion of the reactant may asymptotically approach 100% conversion. So, although from a practical perspective 100% of the reactant is converted, from a technical perspective, a small and sometimes difficult to define amount remains. For this example of a chemical reactant, that amount may be relatively easily defined by the detection limits of the instrument used to test for it. However, in many cases, this amount may not be easily defined, hence the use of the term "substantially". In some embodiments of the present invention, the term "substantially" is defined as approaching a specific numeric value or target to within 20%, 15%, 10%, 5%, or within 1% of the value or target. In further embodiments of the present invention, the term "substantially" is defined as approaching a specific numeric value or target to within 1%, 0.9%, 0.8%, 0.7%, 0.6%, 0.5%, 0.4%, 0.3%, 0.2%, or 0.1% of the value or target.

As used herein, the term "about" is used to indicate that exact values are not necessarily attainable. Therefore, the term "about" is used to indicate this uncertainty limit. In some embodiments of the present invention, the term "about" is used to indicate an uncertainty limit of less than or equal to ±20%, ±15%, ±10%, ±5%, or ±1% of a specific numeric value or target. In some embodiments of the present invention, the term "about" is used to indicate an uncertainty limit of less than or equal to ±1%, ±0.9%, ±0.8%, ±0.7%, ±0.6%, ±0.5%, ±0.4%, ±0.3%, ±0.2%, or ±0.1% of a specific numeric value or target.

As used herein, the term "hydrocarbon" refers to a molecule having a molecular structure comprising carbon and hydrogen. Hydrocarbons may refer to straight-chain or branching aliphatic or aromatic compounds. Hydrocarbons may be classified, as described herein, by the total number of carbons within the molecule. In some embodiments, hydrocarbons may include O molecules in functional groups, for example, alcohols, aldehydes, ketones, etc. In some embodiments, hydrocarbons may include other elements as functional groups, for example, N, S, P, etc.

As used herein, the term syngas refers to a mixture of H gas and carbon monoxide gas (CO). Syngas may also include some concentration of carbon dioxide gas ($CO_2$).

Among other things, the present disclosure relates to the direct conversion of syngas to HOG in a single step, using a single reactor, operating at one process condition (e.g., no temperature or minimal pressure gradient through the reactor). Also shown herein is that $CO_2$ with $H_2$ can be converted to HOG in a single step, and in a single reactor, under similar process conditions to conventional three reactor systems and that $CO/CO_2$ mixtures with $H_2$ can be converted to HOG in a single-step, in a single reactor, operating at one process condition. A stacked catalyst bed configuration, as shown herein, is advantageous for all three feed options (syngas, $CO_2$+$H_2$, and $CO/CO_2$+$H_2$). As discussed below in detail, the advantages of a stacked catalyst bed contained in a single reactor is highlighted by the conversion of $CO_2$ to HOG, where C4+ hydrocarbon products were not observed using a mixed catalyst bed in a single reactor. However, C4+ hydrocarbon yields of greater than 25% were achieved in a single-pass using a stacked catalyst bed configuration in a single reactor.

FIG. 1 illustrates a system 100 for converting a feed stream 110 containing at least one of syngas, CO, and/or $CO_2$ to a product stream 120 containing HOG, according to some embodiments of the present disclosure. The system 100 includes a packed bed reactor 130 containing a stacked catalyst bed 132 of three catalyst layers arranged in series; a first catalyst layer 134, a second catalyst layer 136, and a third catalyst layer 138. In some embodiments of the present disclosure, the feed stream 110 may include at least one of hydrogen ($H_2$), carbon monoxide (CO), carbon dioxide ($CO_2$), water, and/or methane. In some embodiments of the present disclosure, at least a portion of the product stream 120 may be recycled back to and combined with the feed stream. Such a recycle stream 125 may include, among other things, syngas, $CO_2$, methanol, DME, C1-C4 hydrocarbons, and/or other hydrocarbons. As used herein syngas (i.e., synthesis gas) is a gas mixture that includes at least CO and $H_2$. The ratio of $H_2$ to CO ($H_2$:CO) may vary depending on the process and process conditions used to manufacture the syngas. In some embodiments of the present disclosure, the $H_2$:CO ratio may be between about 1:1 and about 4:1, or between about 1:1 and about 3:1.

In some embodiments of the present disclosure, a first catalyst layer 134 may include a first catalyst designed to convert at least one of hydrogen ($H_2$), carbon monoxide (CO), carbon dioxide ($CO_2$), and/or water to methanol. A catalyst for converting a feed stream 110 (e.g., of $H_2$, CO, $CO_2$, water) to methanol may include a solid catalyst that includes copper and zinc oxide. As shown herein, a second catalyst layer 136 may include a second catalyst designed to convert methanol to dimethyl ether (DME). In some embodiments of the present disclosure, a second catalyst for converting methanol to DME may include a solid catalyst that includes at least one of alumina and/or silica and/or a zeolite. As shown herein, a third catalyst layer 138 may include a third catalyst designed to convert DME to high-octane gas (HOG). In some embodiments of the present disclosure, a third catalyst for converting DME to HOG may include a solid catalyst that includes at least one of copper and/or a zeolite. A zeolite may for converting DME to HOG may have a silica to alumina ratio between about 20:1 and about 300:1, or between about 25:1 and about 30:1. In some embodiments of the present disclosure, a zeolite for converting DME to HOG may include a beta zeolite. In some embodiments of the present disclosure, a third catalyst for converting DME to HOG may include a zeolite and copper, where the copper is present at a concentration between about 1 wt % and about 20 wt %, relative to the total weight of the third catalyst, or between about 4 wt % and 10 wt %.

In some embodiments of the present disclosure, any of the catalysts described herein may have any solid shape or form suitable for the given application and/or scale of the process. For example, a catalyst may have a cylindrical form, spherical form, irregular granular form, etc. Further, any of the solid catalysts described herein may have any characteristic length and/or diameter needed for a specific application and/or scale. For example, a catalyst may have a characteristic diameter between about 1/16 inch and about 1/4 inch, or a characteristic length between about 1/2 inch and about 2 inches.

Referring again to FIG. 1, in some embodiments of the present disclosure, three catalysts may be positioned in the packed bed reactor 130 in a stacked catalyst bed configuration, where each catalyst is contained in its own distinct layer (i.e., volume space) positioned adjacent to and in series with its neighboring catalysts that are also contained in their own distinct layers/spaces. So, in the example shown in FIG. 1, the packed bed reactor 130 contains a stacked catalyst bed 132 that includes, in series, a first catalyst layer 134 of essentially only a first catalyst, a second catalyst layer 136 of essentially only a second catalyst, and a third catalyst layer 138 of essentially only a third catalyst. Thus, as described herein and illustrated in FIG. 1, a "stacked catalyst bed" refers to a catalyst bed 132 containing two or more distinct catalyst layers "stacked" in series, where each catalyst layer includes one or more catalyst types. As described in more detail below, in some embodiments of the present disclosure, a catalyst bed 132 may be configured to include a mixture of two or more catalysts. Such a catalyst bed configuration is referred to herein as a "mixed catalyst bed".

For example, a stacked catalyst bed 132 of a packed bed reactor 130 may have only two distinct layers of catalyst, where each of the two distinct layers may include a single catalyst or a mixture of at least two catalysts. In some embodiments of the present disclosure, a stacked catalyst bed 132 may include a first catalyst layer 134 and a second catalyst layer 136 (i.e., no third catalyst layer 138), where the first catalyst layer 135 includes a mixture of at least two catalysts, a first catalyst for converting a feed stream 110 to methanol and a second catalyst for converting methanol to DME, and the second catalyst layer 136 includes essentially only one catalyst for converting DME to HOG. In some embodiments of the present disclosure, a stacked catalyst bed 132 of a packed bed reactor 130 may include a first catalyst layer 134 and a second catalyst layer 136 (i.e., no third catalyst layer 138), where the first catalyst layer 135 includes essentially only one catalyst for converting a feed stream 110 to methanol and the second catalyst layer 136 includes a mixture of a second catalyst for converting methanol to DME and a third catalyst for converting DME to HOG. In some embodiments of the present disclosure, a packed bed reactor 130 may have a mixed catalyst bed 132 having only a single catalyst layer where the single catalyst layer includes a mixture of at least three catalysts, a first catalyst for converting a feed stream 110 to methanol, a second catalyst for converting methanol to DME, and a third catalyst for converting DME to HOG.

When combining more than one catalyst into a single layer, the catalysts may be combined into a single homogeneous mixture (i.e., essentially no variation in catalyst concentration as a function of position within the catalyst layer) by standard mixing operations; e.g., tumbling, grinding, pressing, extruding. Such a homogeneous mixture may be formed by combining at least two catalyst powders, mixing them, and pressing them into pellets that contain the two or more catalysts. Or each individual catalyst may be pressed into its own batch of pellets after which the two or more batches of pellets are mixed together into a homogeneous mixture. So, in some embodiments of the present disclosure, a packed bed reactor 130 may include a stacked catalyst bed 132 having two or more distinct catalyst layers, where at least one of the catalyst layers includes two or more catalyst types. In other words, a portion of a stacked catalyst bed may include a mixed catalyst bed. Further, in some embodiments of the present disclosure, a catalyst layer (e.g., 134, 136, and/or 138) may also include an inert solid such as silicon carbide to minimize channeling, axial dispersion, and/or temperature gradients in the packed bed reactor 130.

The ratios of the catalysts present in a packed bed reactor 130 may be varied depending on, among other things, the composition and/or conditions of the feed stream 110. In addition to varying the composition of the feed stream 110, e.g., $H_2$:CO ratio, the temperature of the feed stream 110 entering a packed bed reactor 130 may be in a range between about 180° C. and about 320° C., according to some embodiments of the present disclosure. The pressure of the feed stream 110 entering a packed bed reactor 130 may be between about 300 kPa and about 5.5 MPa. In some embodiments of the present disclosure, the pressure-drop through a packed bed reactor 130 may be between zero Pa and about 500 kPa. In some embodiments of the present disclosure, the feed stream 110 may be provided at a flow rate such that a space velocity is achieved in the packed bed reactor 130 between about 0.2 g CO/g catalyst hr and about 1.5 g CO/g catalyst hr, or between about 0.2 g CO/g catalyst hr and about 0.8 g CO/g catalyst hr. In some embodiments of the present disclosure, the feed stream 110 may be provided at a flow rate such that a space velocity is achieved in the packed bed reactor 130 between about 0.2 g DME/g catalyst hr and about 1.5 g DME/g catalyst hr, or between about 0.2 g DME/g catalyst hr and about 0.8 g DME/g catalyst hr. The ratio of the first catalyst to the second catalyst may be between about 1:1 and about 8:1, or between about 1:1 and about 32:5, according to some embodiments of the present disclosure. The ratio of the second catalyst to the third catalyst may be between about 0.1:1 and about 5:2, or between about 0.1:1 and 3:1, according to some embodiments of the present disclosure. As described herein, these catalyst ratios may be used both for the embodiment where each catalyst is provided in its own distinct layer and also for the embodiments utilizing mixtures of catalysts.

Referring again to FIG. 1, the packed bed reactor 130 is shown in a horizontal position. This is for illustrative purposes only, and other orientations fall within the scope of the present disclosure. For example, a packed bed reactor 130 may be positioned vertically, where in some cases the feed stream 110 flows from the bottom through the packed bed reactor 130, such that the product stream 120 exits the packed bed reactor 130 at a height above the point of entry of the feed stream 110 into the packed bed reactor 130 (i.e., bottom-up configuration). In some embodiments of the present disclosure, a vertical packed bed reactor 130 may be configured such that the feed stream 110 flows from the top through the packed bed reactor 130, such that the product stream 120 exits the packed bed reactor 130 at a height below the point of entry of the feed stream 110 into the packed bed reactor 130 (i.e., top-down configuration).

Referring again to FIG. 1, the exemplary system 100 illustrates the use of a single packed bed reactor 130, which provides, among other things, process simplification. However, in some embodiments of the present disclosure, a system for converting syngas to HOG may utilize two packed bed reactors positioned in series. Thus, in some embodiments of the present disclosure, a first reactor (not shown) may include a single catalyst layer of one or more catalysts, or a first reactor may include a first catalyst layer of a first catalyst positioned in series with a second catalyst layer of a second catalyst. The product stream from the first reactor may then be directed to a second reactor, where the second reactor may include a single catalyst layer of one or more catalysts, or the second reactor may include a first catalyst layer of a first catalyst positioned in series with a second catalyst layer of a second catalyst. In some embodiments of the present disclosure, the product stream from a second reactor may then be directed to a third reactor, where the third reactor may include a single catalyst layer of one or more catalysts, or the third reactor may include a first catalyst layer of a first catalyst positioned in series with a second catalyst layer of a second catalyst. Among other things, separating different catalysts and/or catalyst mixtures into separate reactors may enable better process control of the different reactions occurring in the different reactors.

In a first example, a first packed bed reactor may include a stacked catalyst bed having a first catalyst layer that includes essentially only a catalyst for converting syngas to methanol, followed in series by a second catalyst layer that includes essentially only a catalyst for converting methanol to DME. The DME produced in the first packed bed reactor may then be directed to a second packed bed reactor (e.g., via conduit, piping, etc.) that includes a stacked catalyst bed of essentially only a single catalyst layer of only one catalyst for converting DME to HOG. In a second example, a first packed bed reactor may include a mixed catalyst bed having only a single catalyst layer of a mixture of two catalysts, a first catalyst for converting syngas to methanol and a second catalyst for converting methanol to DME. The DME produced in the first packed bed reactor may then be directed to a second packed bed reactor (e.g., via conduit, piping, etc.) that includes a stacked catalyst bed of essentially only a single catalyst layer having only a single catalyst for converting DME to HOG. In a third example, a first packed bed reactor may include a stacked catalyst bed having a single catalyst layer that includes essentially only one catalyst for converting syngas to methanol. The methanol produced in the first packed bed reactor may then be directed to a second packed bed reactor (e.g., via conduit, piping, etc.) having a stacked catalyst bed that includes a first catalyst layer of a first catalyst for converting methanol to DME and a second catalyst layer of a second catalyst in series for converting DME to HOG. In a fourth example, a first packed bed reactor may include a stacked catalyst bed having a single catalyst layer that includes essentially only one catalyst for converting syngas to methanol. The methanol produced in the first packed bed reactor may then be directed to a second packed bed reactor (e.g., via conduit, piping, etc.) having a mixed catalyst bed of a single catalyst layer of a mixture of a first catalyst and a second catalyst, where the first catalyst converts methanol to DME and the second catalyst converts DME to HOG. Among other things, the systems and methods and their corresponding features described above may improve the overall yield of HOG, reduce $CO_2$ emissions, and improve the process economics for producing HOG.

The systems, methods, and catalysts described herein, among other things, convert CO and/or $CO_2$ with co-fed $H_2$ to hydrocarbons through a series of reactions performed by each catalyst in a single reactor, or in one or more reactors. As described herein, a single reactor was tested that included a first catalyst of copper-zinc oxide-alumina (CZA) to perform methanol synthesis as shown in Reaction 1, a second catalyst of gamma-alumina (A) to perform methanol dehydration as shown in in Reaction 2, and a third catalyst of Cu/BEA to perform hydrocarbon synthesis as shown in Reaction 3, where the targeted hydrocarbon product was a high-octane gasoline (HOG) mixture, rich in 2,2,3-trimethylbutane (a.k.a. triptane). When feeding syngas, Reactions 1, 2, and 3 occur sequentially in this scheme, suggesting that an optimum HOG yield can be achieved by controlling the relative activity of each catalyst and/or the mass ratio of catalysts in the reactor. Reaction 4, the water-gas shift reaction (WGSR), is a known side-reaction in this system that can be catalyzed by both CZA and Cu/BEA. When feeding $CO_2$ and $H_2$, the reverse-WGSR is the first step in the reaction sequence, converting $CO_2$ to CO that can then be converted to methanol via Reaction 1. Note that all of Reactions 1-4 have a thermodynamic equilibrium at the reaction temperatures tested here (between about 220° C. and about 240° C.) that can limit the extent to which reactants may be converted. Further, the reverse of Reactions 1 and 2 can occur at high concentrations of water or MeOH in the reactor. For methanol synthesis, Reaction 1, this equilibrium limitation is especially problematic as its equilibrium constant is small, ranging from $K_{eq,rxn1}$(T=220° C.)=0.0016 to $K_{eq,rxn1}$(T=240° C.)=0.0006.

CO+2H$_2$↔CH$_3$OH    [Reaction 1; methanol synthesis]

2 CH$_3$OH↔CH$_3$OCH$_3$+H$_2$O    [Reaction 2; methanol dehydration; i.e. DME synthesis]

$x$ CH$_3$OCH$_3$+$y$ H$_2$→$z$ C$_n$H$_{2n+2}$+$x$ H$_2$O    [Reaction 3; HOG synthesis]

CO+H$_2$O↔CO$_2$+H$_2$    [Reaction 4; water-gas shift reaction]

When these reactions take place in the same reactor and are catalyzed with a multifunctional catalyst system such as the CZA+A tested here, the equilibrium conversion of CO can be increased due to a synergistic effect between Reactions 1 and 2. Specifically, by including A to catalyze methanol dehydration (Reaction 2), the in situ concentration of MeOH can be kept low, but a greater flux of MeOH through Reaction 1 can be achieved than the thermodynamic equilibrium would allow if Reaction 1 were performed independently. Similar thermodynamic arguments can be made with the addition of Reaction 3, whereby irreversible conversion of DME over Cu/BEA ($K_{eq,rxn3}$>10$^{50}$) keeps the in situ DME concentration low, thus preventing Reaction 2 from reaching equilibrium.

The equilibrium constant $K_{eq}$ is only a function of temperature for these gas-phase reactions and is not a function of pressure or composition. However, through Le Chatelier's principle the equilibrium concentration of MeOH in the reactor can be increased by increasing the absolute reactor pressure. Assuming ideal gas behavior (fugacity coefficients=1), Equation 1 specifies the equilibrium constant for methanol synthesis:

$$K_{eq,rxn1} = \Pi_i a_i^{\gamma_i} = \frac{x_{MeOH}}{(x_{CO})(x_{H_2})^2(P)^2}$$    Equation (1)

where $a_i$ are the activities, $\gamma_i$ are stoichiometric coefficients, $x_i$ are the mole fractions of reactants and products and P is the reactor pressure. As $K_{eq}$ is constant at a given temperature, an increase in reactor pressure P at constant temperature results in an increase in $x_{MeOH}$. Reactions 2 and 4 are stoichiometrically equimolar, and therefore the concentrations of reactants and products in those reactions are not directly affected by reactor pressure. The thermodynamics of syngas conversion to hydrocarbons outlined here exemplifies the need to balance reaction rates and/or equilibria of each reaction step to achieve optimal performance. One method of control is the catalyst composition (i.e., the relative CZA, A, and Cu/BEA mass loadings). Additionally, the reaction temperature and pressure are expected to alter the concentration of key intermediate species (MeOH, DME), thus requiring condition-specific compositions of CZA, A, and Cu/BEA for optimal hydrocarbon production.

Figure 2A:
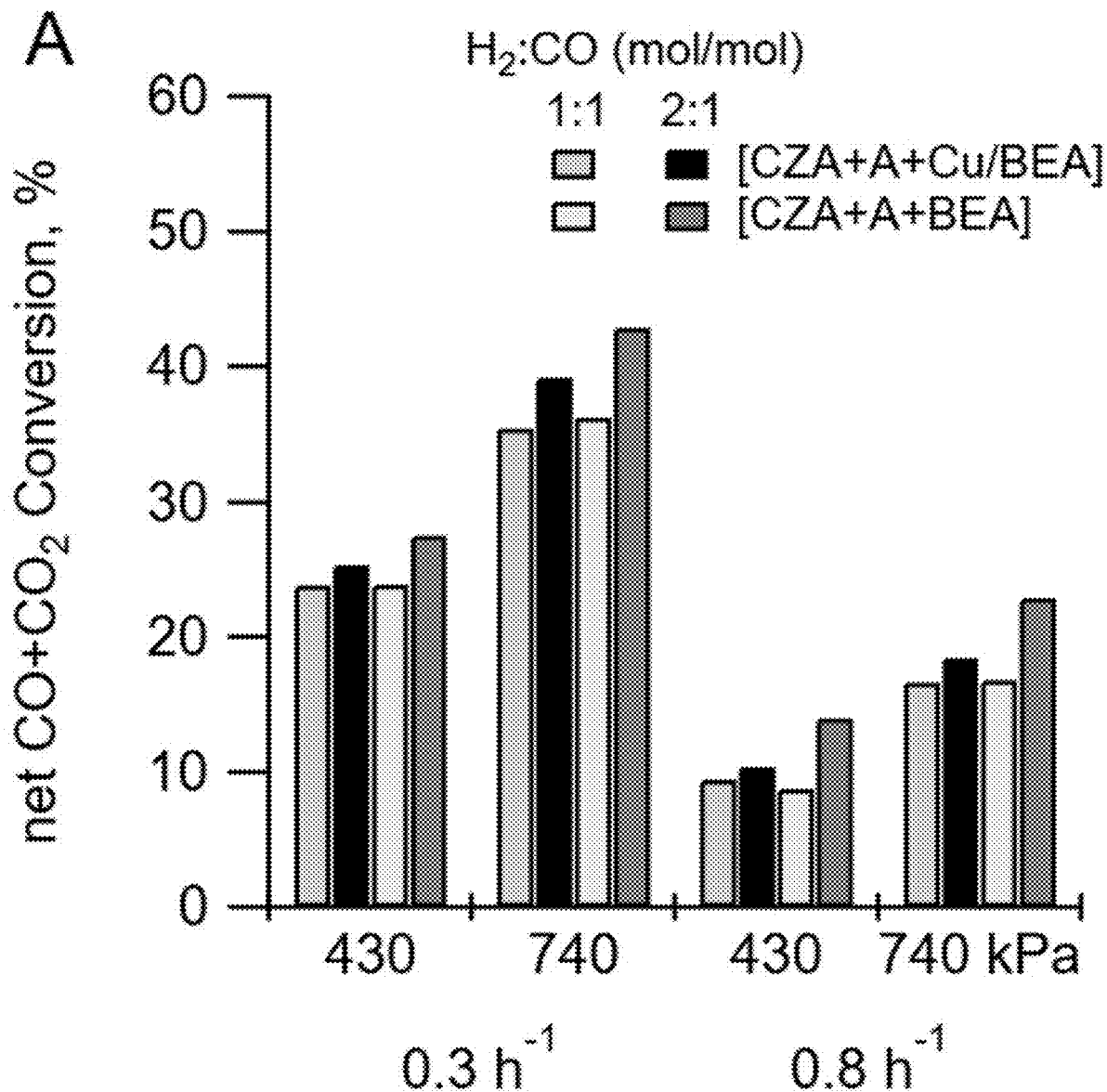
FIGS. 2A-2B illustrate the effect of zeolite (BEA or Cu/BEA) on (A) $CO+CO_2$ conversion and (B) $C_{4+}$ hydrocarbon yield during syngas-to-HOG reactions, according to some embodiments of the present disclosure. Experiments were performed at 220° C., with a reactant mixture of 1:1 or 2:1 $mol_{H2}$-$mol_{CO}^{-1}$, and weight-hourly space velocity of CO ($SV_{CO}$) of 0.3 or 0.8 $g_{CO}$-$g_{CZA+A}^{-1}$-$h^{-1}$. The absolute reaction pressure was 430 or 740 kPa, respectively.

Reactions of Syngas with and without Co-Fed CO$_2$:

Mixed catalyst beds of CZA+A with BEA versus Cu/BEA: The effect of the zeolite catalyst for Reaction 3 was compared between unmodified BEA and Cu-modified BEA (Cu/BEA) in a mixed catalyst bed configuration with combined press-crush-sieve preparation procedure, denoted [CZA+A+BEA] and [CZA+A+Cu/BEA]. The reaction temperature was 220° C., SV$_{CO}$ was 0.3 or 0.8 h$^{-1}$, H$_2$:CO mol ratio was 1:1 or 2:1, and reaction pressure was 430 or 740 kPa. The net CO+CO$_2$ conversion at each condition was similar when using BEA or Cu/BEA (see FIG. 2A). Despite the overall low C$_{4+}$ hydrocarbon yields, the Cu/BEA catalyst demonstrated yields at each condition that were at least double the yield from BEA (see FIG. 2B). These data indicate that the unmodified BEA catalyst is active for hydrocarbon production from syngas under a variety of conditions, but that the Cu/BEA catalyst provides greater activity.

Stacked versus Mixed Bed Configuration: Two catalyst bed configurations were tested. A stacked catalyst bed configuration, CZA+A|Cu/BEA, was loaded such that the top bed, or up-stream bed, consisted of physically mixed CZA and A (ca. 3.1, 0.50 g, respectively). The second, or downstream, bed consisted of Cu/BEA (ca. 0.20 g). In this example, the two catalyst beds were isolated by a thin plug of quartz wool, which may not be necessary. The second configuration was a single, mixed catalyst bed of CZA+A+Cu/BEA (ca. 3.1, 0.50, 0.20 g, respectively). For both catalyst bed configurations, the three materials were sieved to an identical particle size distribution (between 212 μm and 300 μm) to mitigate size- and shape-dependent settling. Therefore, the mixed catalyst bed was assumed to be evenly dispersed throughout the bed.

Figure 3A:
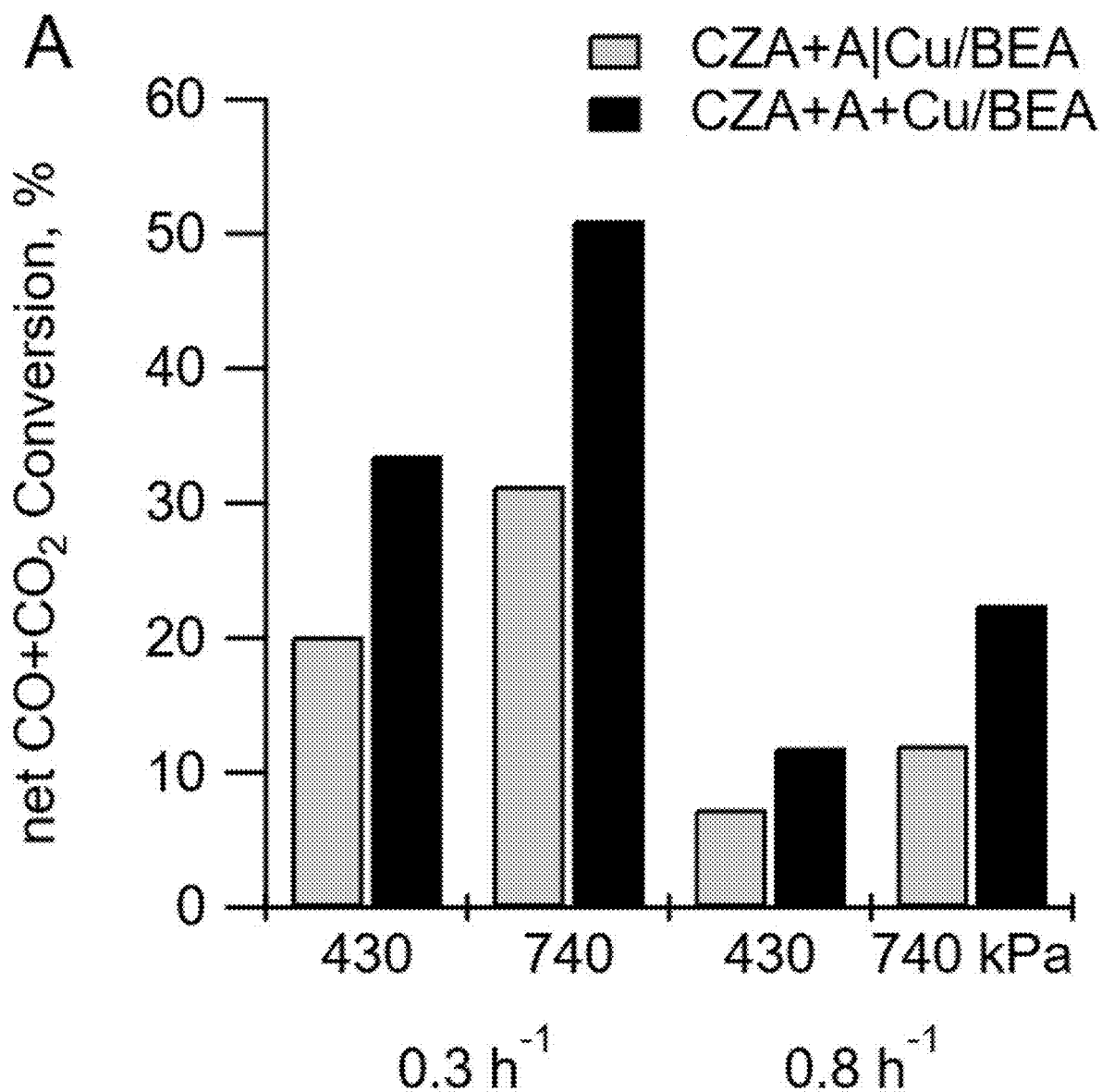
FIGS. 3A-3D illustrate the effect of catalyst bed configurations, stacked catalyst bed versus mixed catalyst bed, according to some embodiments of the present disclosure. (A) net $CO+CO_2$ conversion, (B) DME carbon selectivity, (C) $C_{4+}$ hydrocarbon yield, and (D) carbon number product selectivity during syngas-to-HOG reactions. Experiments were performed over CZA+A|Cu/BEA and CZA+A+Cu/BEA at 220° C., 430 or 740 kPa absolute, and $SV_{CO}$ of 0.3 or 0.8 $g_{CO}$-$g_{CZA+A}^{-1}$-$h^{-1}$. All syngas data shown at $H_2$:CO=1.0. Data from reactions with syngas in FIG. 3D were collected at $SV_{CO}$ of 0.3 $g_{CO}$-$g_{CZA+A}^{-1}$-$h^{-1}$. Data for the reference DME to HOG were collected at 220° C., 320 kPa absolute, with $SV_{DME}$ of 0.6 $g_{DME}$-$g_{CuBEA}^{-1}$-$h^{-1}$ and $H_2$:DME=ca. 1.0 $mol_{H2}$-$mol_{DME}^{-1}$.
Figure 3B:
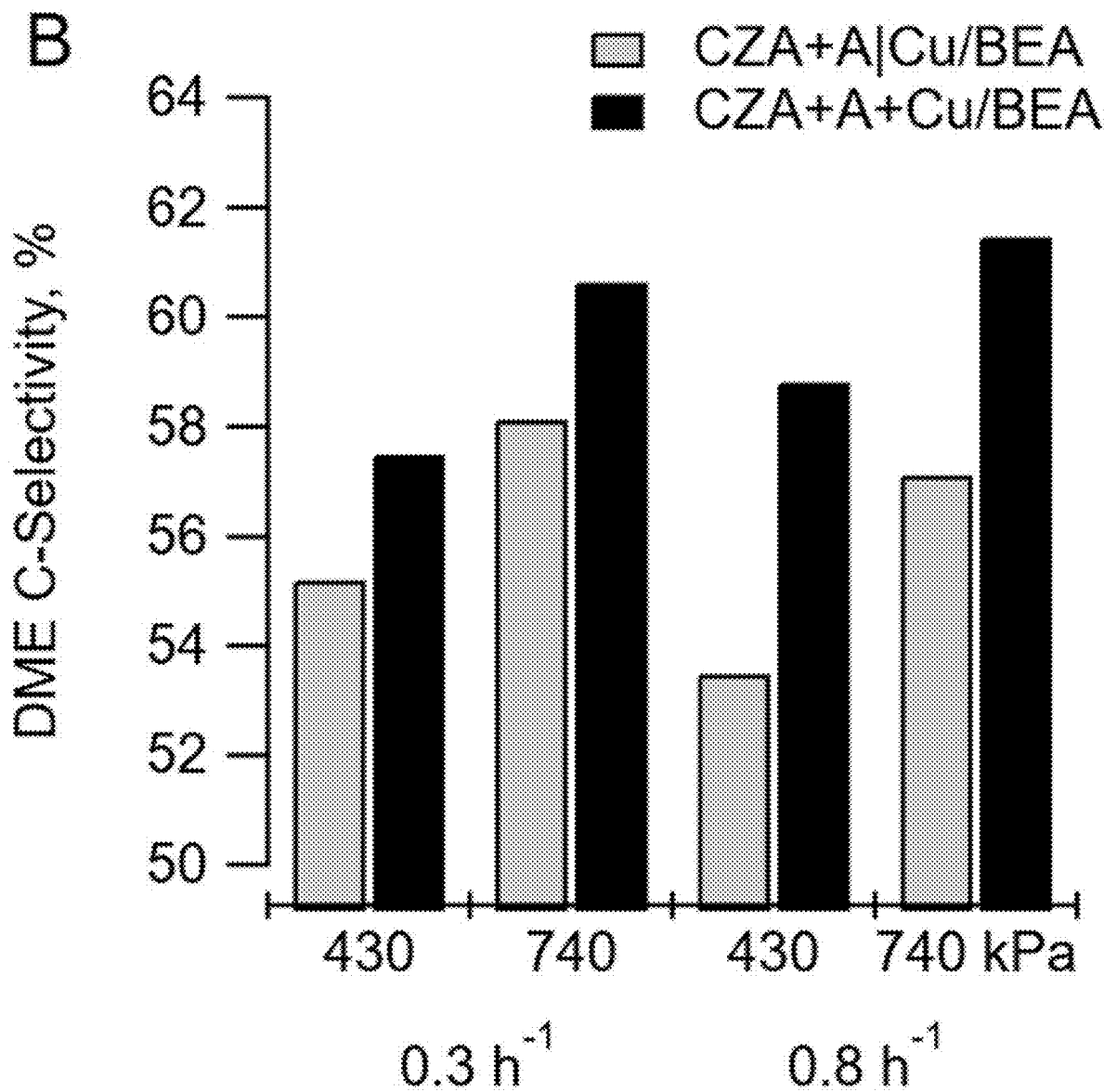
Figure 3C:
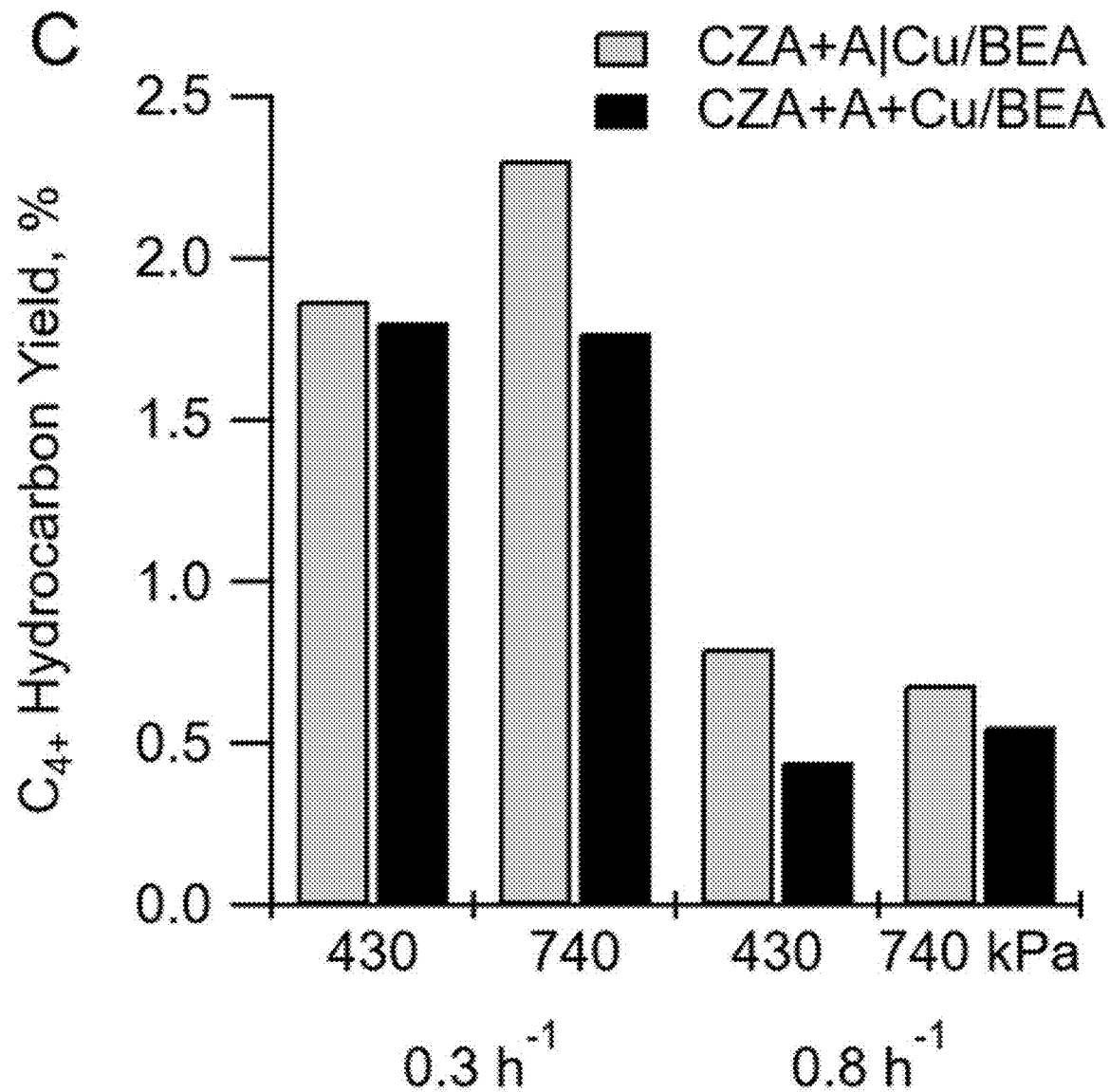

The net CO+CO$_2$ conversion from the mixed catalyst bed experiment exceeded that of the stacked catalyst bed over a series of SV and reaction pressure conditions, exhibiting a relative increase of 40-60% (see FIG. 3A). Conversion increased with pressure (430 to 740 kPa) and with decreasing SV (0.8 to 0.3 h$^{-1}$), attributed to greater MeOH production at higher pressure, where the reaction equilibrium shifts toward higher MeOH concentration with increasing pressure, and with longer residence time in the reactor. The sequential reactions are affected by increased MeOH yield, initially generating more DME, which is exemplified by a greater selectivity to DME under higher pressure and lower SV conditions (see FIG. 3B). Subsequently, increased C$_{4+}$ hydrocarbon yield is expected at higher pressures and lower SV. FIG. 3C shows that this trend is generally followed, but that lower SV is more impactful to the hydrocarbon yield.

Figure 2B:
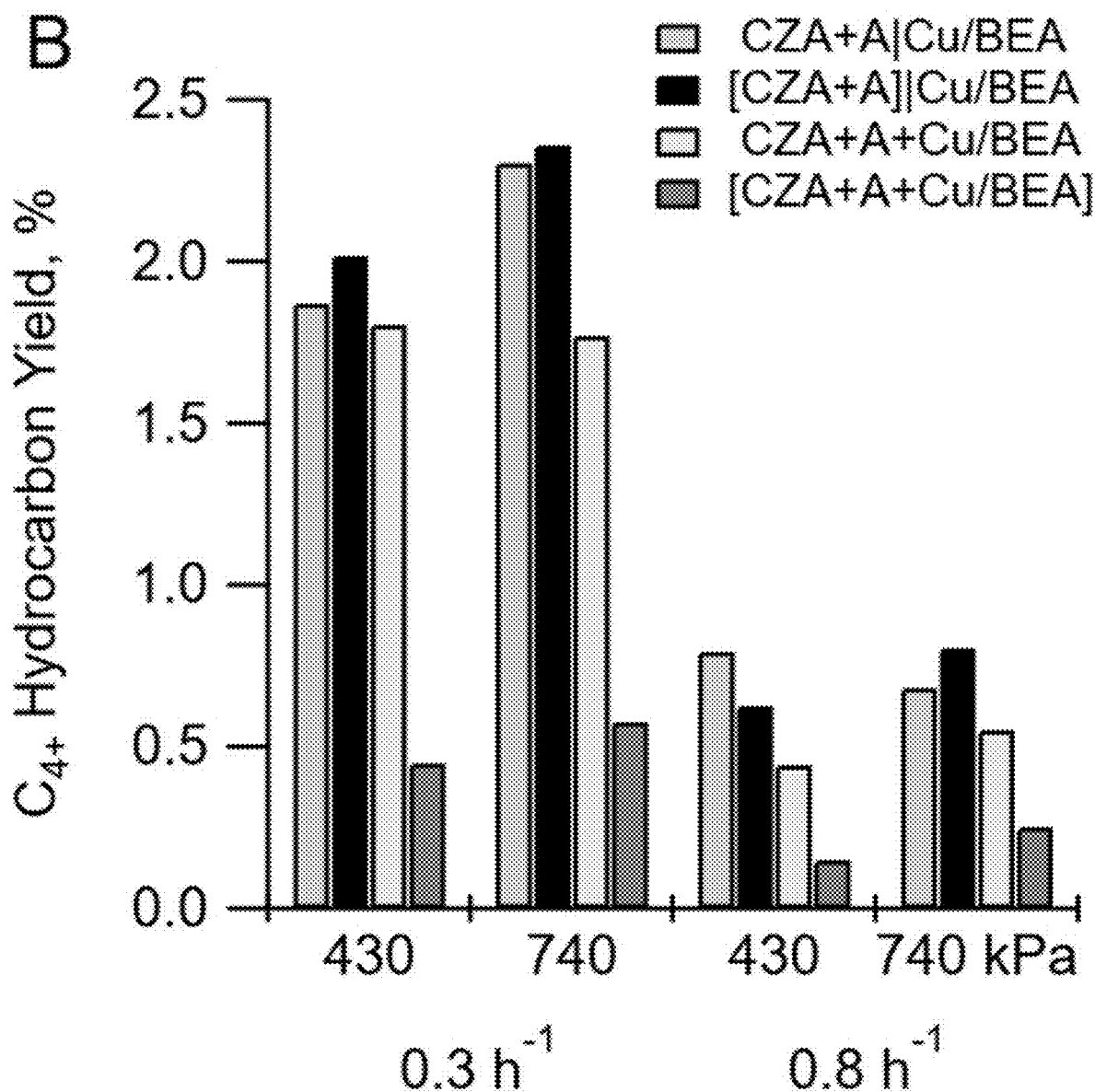

The hydrocarbon yield from the stacked catalyst bed experiments exceeded that of the mixed catalyst bed. A yield of 2.3% was achieved for the stacked catalyst bed at 740 kPa with a SV of 0.3 h$^{-1}$. Note that the higher C4+ yields shown in FIG. 3C compared to FIG. 2B are attributed to catalyst preparation procedure, which is discussed in more detail in the subsequent section. Despite greater DME production, the lower C$_{4+}$ hydrocarbon yield from the mixed catalyst bed configuration may be due to kinetic effects. For the mixed catalyst bed, the Cu/BEA component was evenly dispersed throughout the bed, however, an appreciable concentration of DME is unlikely to have formed in the initial length of the catalyst bed. Therefore, a non-negligible fraction of the Cu/BEA in the top of the mixed catalyst bed may have been inactive or reactant-limited, leading to the observed lower hydrocarbon yield and higher DME selectivity. In contrast, for the stacked catalyst bed experiment, the entire Cu/BEA catalyst was exposed to the full concentration of DME generated in the up-stream bed of CZA+A, leading to greater hydrocarbon production and a lower observed DME selectivity.

Figure 3D:
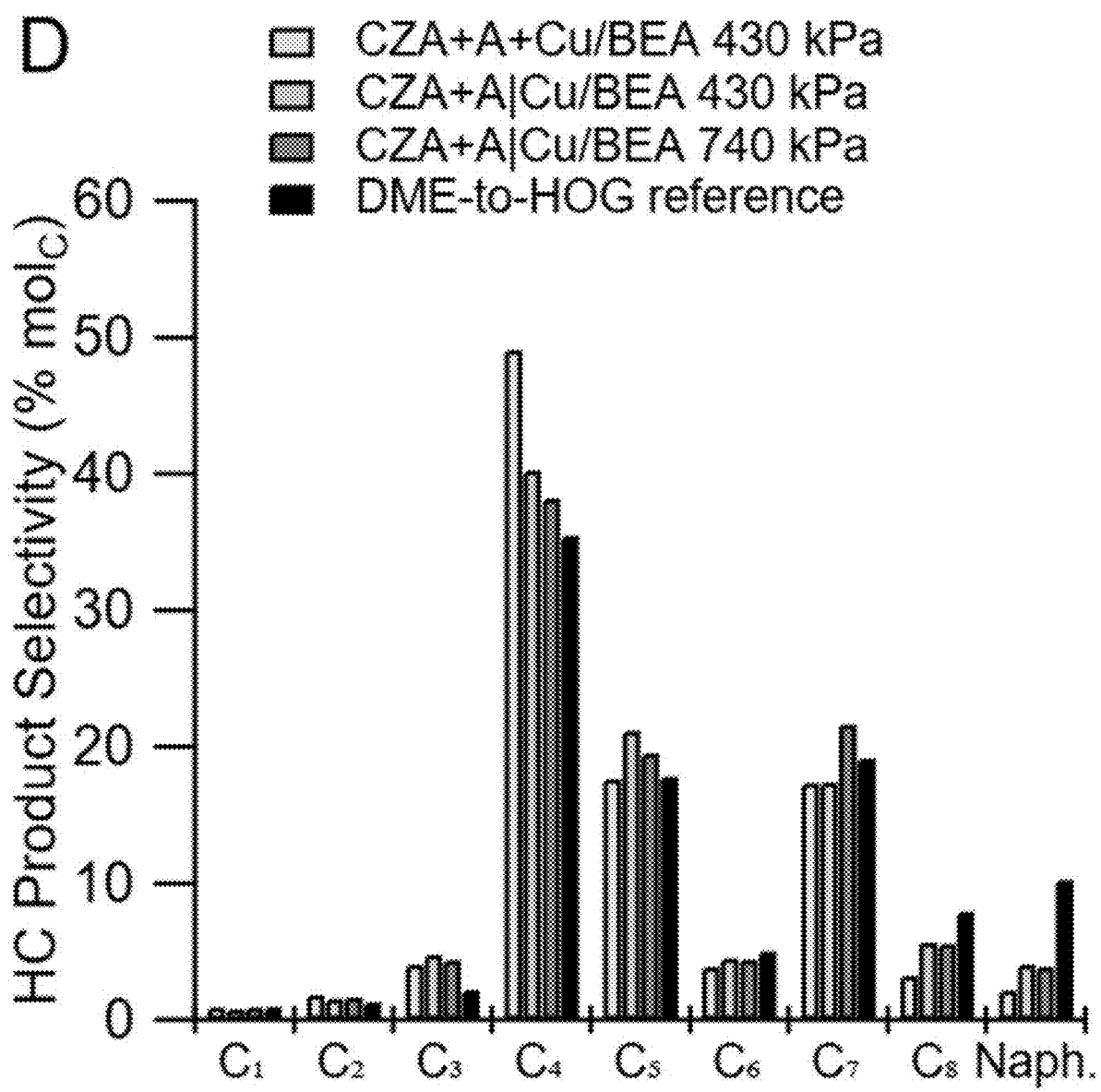

The oxygenate-free carbon selectivity to hydrocarbon products grouped by carbon number (determined using Equation 5) are provided in FIG. 3D, comparing mixed catalyst bed data and stacked catalyst bed data at a common SV of 0.3 h$^{-1}$. The production of naphthenes (i.e., methylated cyclohexanes) was observed in all datasets. These cyclic products can be attributed to cyclization reactions of dienes with mono-olefins followed by hydrogenation (e.g., Diels-Alder reactions), intramolecular cyclization of long-chain trienes followed by hydrogenation, and/or hydrogenation of aromatic intermediates such as hexamethylbenzene, which is the only aromatic product observed in this chemistry over BEA zeolite catalysts. Of the observed naphthene products, more than 95% of these are $C_{8+}$ cyclic products. The selectivity values observed from syngas conversion illustrate that the hydrocarbon pool chemistry of DME to hydrocarbons over the Cu/BEA catalyst remains intact despite the substantial changes to process conditions (i.e., high concentrations of CO and $H_2$, higher temperature, higher pressure). Relatively high selectivity to $C_4$ products and relatively low selectivity to the $C_{7-9}$ products was observed over the mixed catalyst bed. This shift toward $C_4$ products may be the result of low DME conversion through the sequential reactions from syngas, or of decreased DME partial pressure relative to typical DME-to-hydrocarbons reactions that directly feed DME. Importantly, for both catalyst bed configurations (stacked and mixed) and across all conditions, no products from unforeseen side-reactions were observed, evidenced by typical selectivity to $CH_4$ and the absence of methyl acetate, ethanol, or higher alcohols. The selectivity for both stacked catalyst bed conditions (430 and 740 kPa) exhibited a lower $C_4$ selectivity than the mixed catalyst bed, with increasing selectivity to the desired $C_{5+}$ and $C_{7-9}$ products. At 740 kPa, the product selectivity for $C_7$ increased to 21.6%, exceeding that of the reference case (19.1%).

Catalyst processing procedure: The effect of catalyst processing procedure was investigated by varying whether catalyst components were pressed, crushed, and sieved together (notated in [brackets]) or separately (notated without brackets) in FIGS. 4A-4C. All catalyst components were prepared for catalytic testing after a similar press, crush, and sieve procedure, where the only difference was whether components were processed together or were mixed together after independent processing. The stacked catalyst bed configuration had CZA and A components processed together prior to loading, with a final bed configuration of [CZA+A]|Cu/BEA. The mixed catalyst bed included all three catalyst components processed together, giving [CZA+A+Cu/BEA], such that each particle would contain each of the three catalyst components.

Figure 4A:
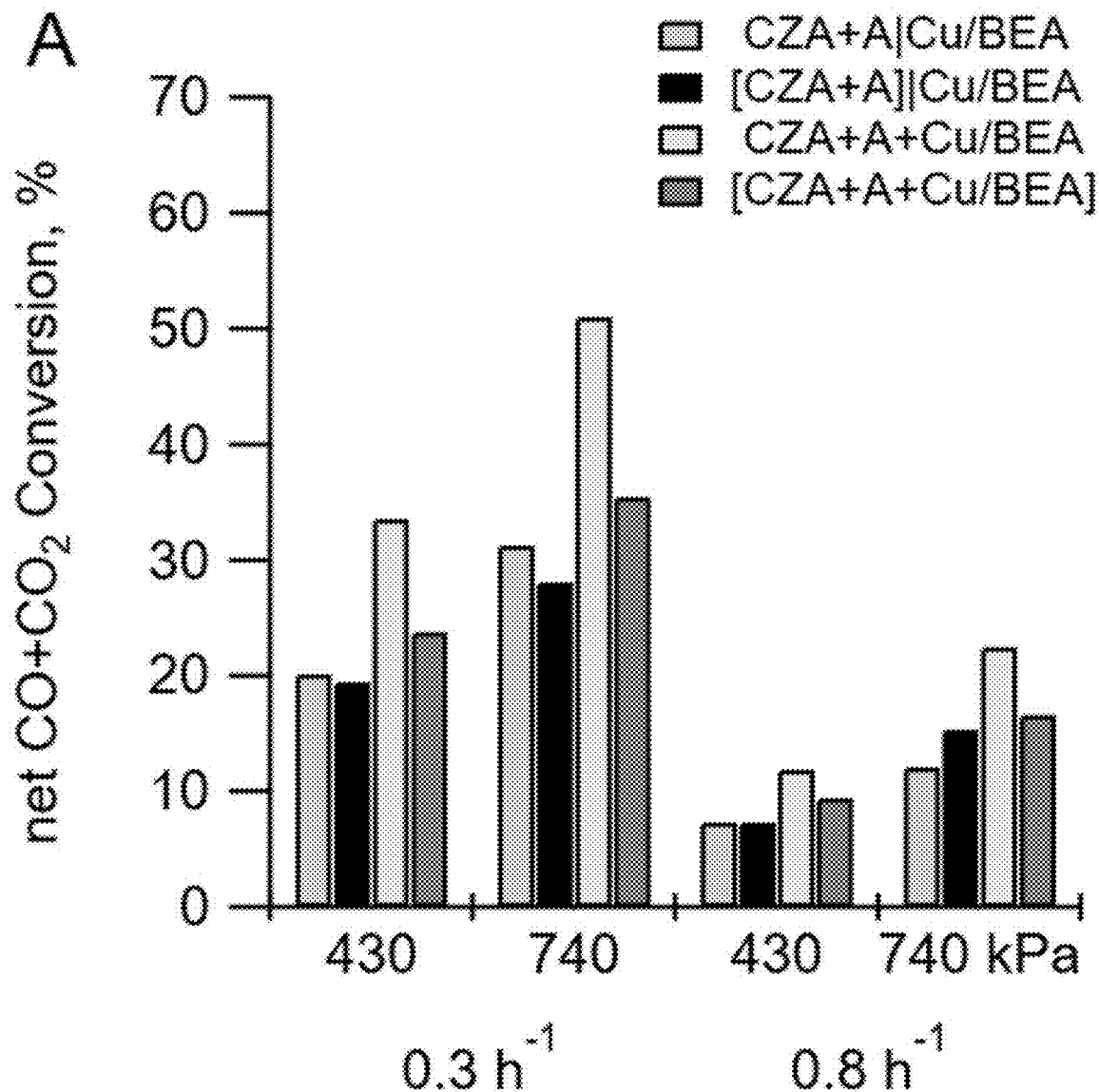
FIGS. 4A-4C illustrate the effect of catalyst press, crush, sieve procedure on (A) net $CO+CO_2$ conversion, (B) $C_{4+}$ hydrocarbon yield, and (C) $C_1$ oxygenate yield during syngas-to-HOG reactions, according to some embodiments of the present disclosure. Experiments were performed at 220° C., with a reactant mixture of 1:1 $mol_{H2}$-$mol_{CO}^{-1}$. The $SV_{CO}$ and absolute reaction pressure were 0.3 or 0.8 $g_{CO}$-$g_{CZA+A}^{-1}$-$h^{-1}$ and 430 or 740 kPa, respectively.
Figure 4B:
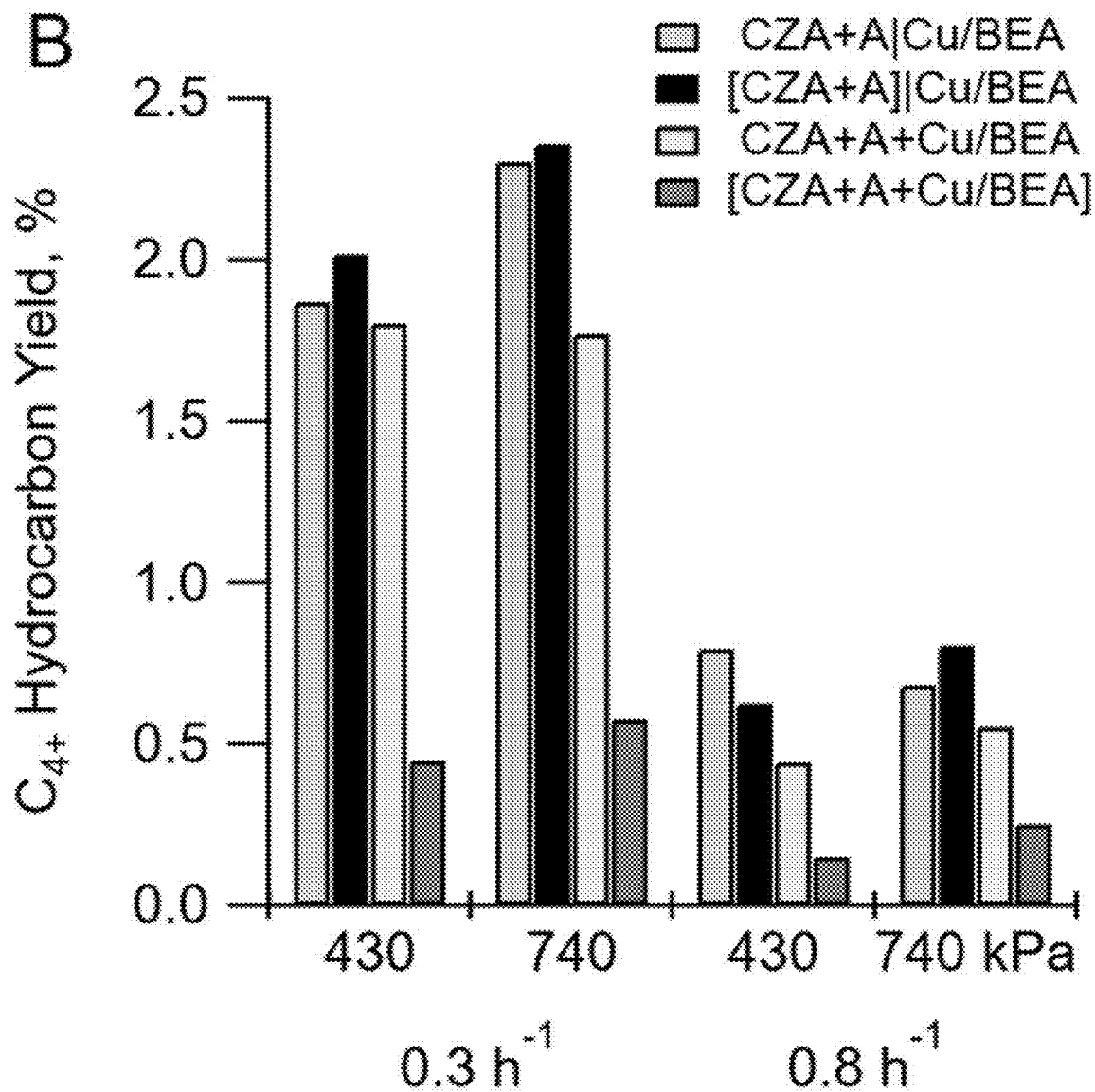
Figure 4C:
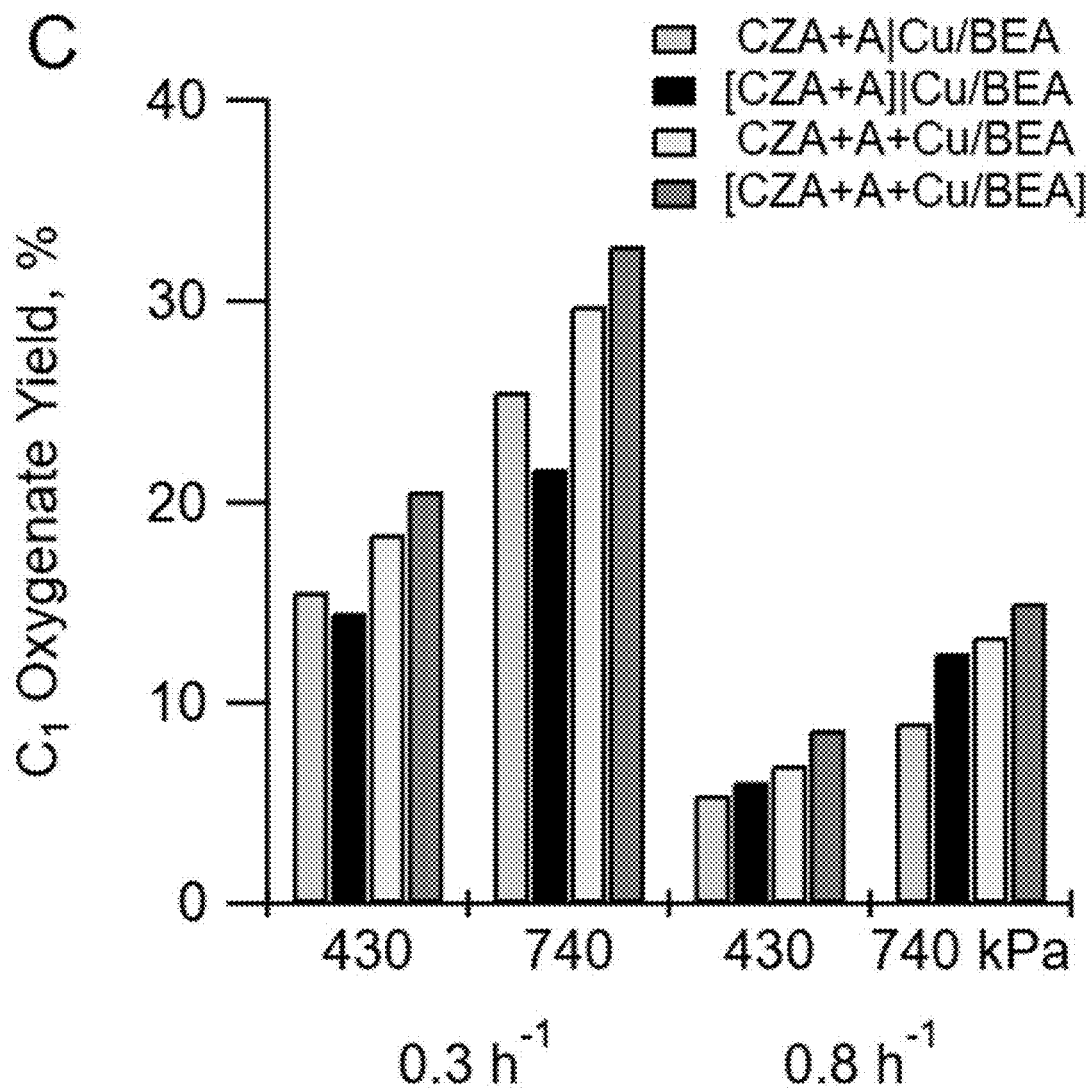

The hypothesis was that bringing catalyst components in closer proximity than could otherwise occur by physical mixing of homogenous particles would lead to an increase in $CO+CO_2$ conversion and hydrocarbon yield, however, the $CO+CO_2$ conversion for the stacked catalyst bed was not dramatically affected by preparation procedure, and the conversion over the mixed catalyst bed exhibited a relative decrease of 10-25% (see FIG. 4A). Similarly, FIG. 4B shows that the $C_{4+}$ hydrocarbon yield was either not strongly affected, especially for stacked catalyst bed configurations, or reduced, especially for mixed catalyst bed configurations. The hydrocarbon product selectivity was comparable between the two stacked catalyst bed configurations and the mixed catalyst bed of CZA+A+Cu/BEA. A shift to greater $C_{1-3}$ selectivity and lower $C_{5+}$ selectivity was observed for the [CZA+A+Cu/BEA], but selectivity comparisons are difficult to make due to the significantly lower yield. The marked reduction in $C_{4+}$ hydrocarbon yield for the combined mixed catalyst bed [CZA+A+Cu/BEA], relative to the independently prepared CZA+A+Cu/BEA mixed catalyst bed, yet only minor difference between the stacked catalyst bed configurations (CZA+A|Cu/BEA versus [CZA+A]/Cu/BEA), suggests that the preparation procedure is most disruptive when Cu/BEA is processed with the other catalyst components. Comparing a number of additional metrics, the pressing, crushing, and sieving of CZA+A together (i.e., [CZA+A]) did not significantly affect performance across the conditions explored here.

In contrast to the decrease in $C_{4+}$ hydrocarbon yield observed over [CZA+A+Cu/BEA], comparable $C_1$ oxygenate yield was observed between the two mixed catalyst bed configurations, CZA+A+Cu/BEA and [CZA+A+Cu/BEA] (see C). These results suggest that the catalytic activity over CZA and A remained intact (i.e., Reactions 1, 2 and 4), while the subsequent activity for conversion of MeOH/DME to hydrocarbons over Cu/BEA (i.e., Reaction 3) was considerably reduced. A reduction in the Cu/BEA activity could be due to: (i) mass transport limitations, such as limited intraparticle diffusion rendering a portion of the Cu/BEA catalyst inactive or reactant-limited, (ii) pore blockage and/or a reduction in surface area of the zeolite catalyst after the processing procedure, or (iii) an intrinsic disadvantage to having the various catalyst components in close proximity, such as additional side-reactions that are promoted under these conditions. If the lower activity is due to mass transport limitations or pore blockage/reduced surface area, one mitigation approach is a catalyst composition comprising the multiple active sites necessary for each reaction (e.g., metallic Cu, ionic Cu-zeolite, ZnO, $Al_2O_3$, BEA zeolite) assembled with a hierarchical pore structure to enable efficient mass transport.

Figure 5A:
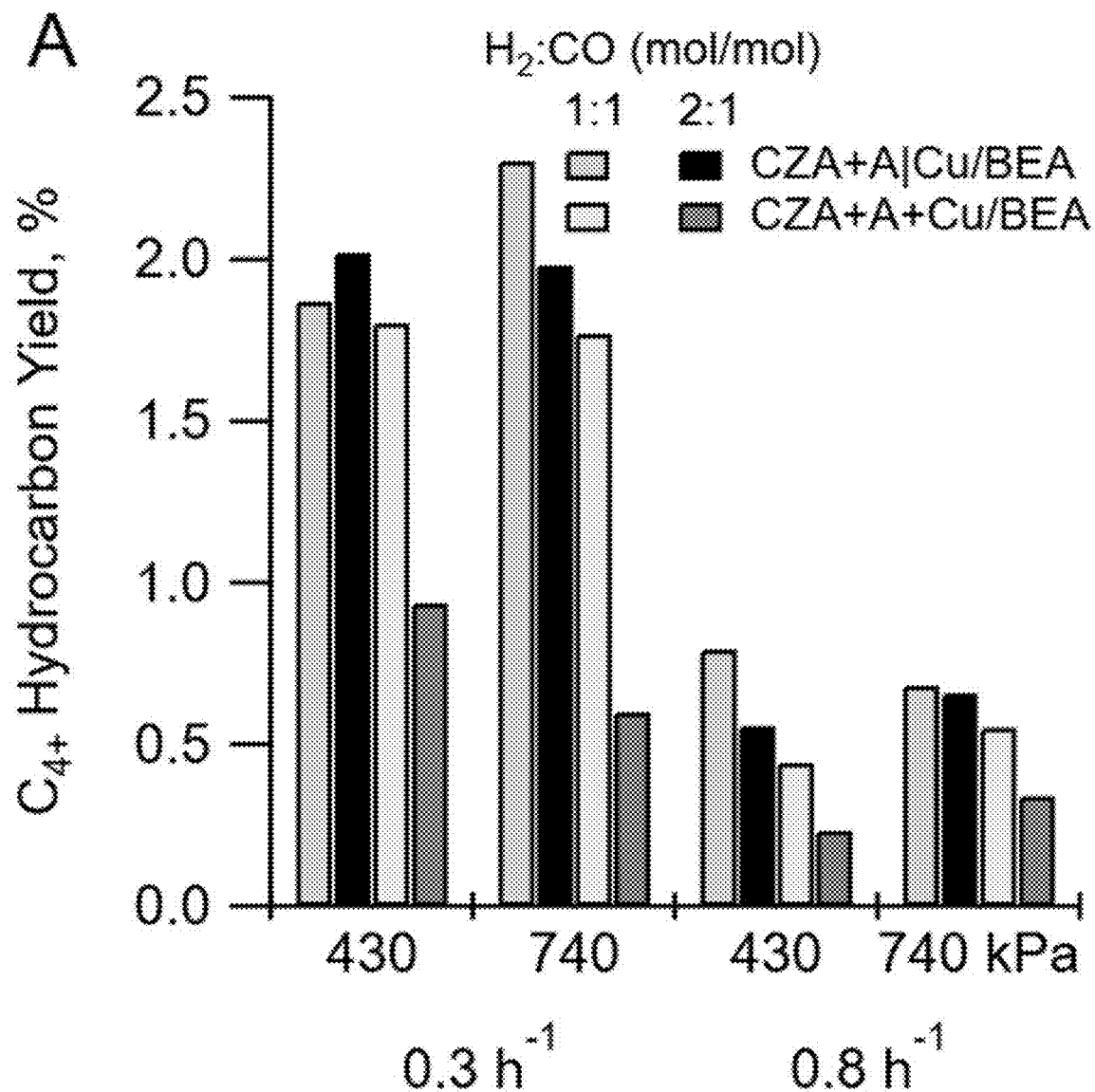
FIGS. 5A-5C illustrate the effect of $H_2$ to CO molar ratio on (A) $C_{4+}$ hydrocarbon yield, (B) $CO_2$ carbon selectivity, and (C) DME carbon selectivity during syngas-to-HOG reactions, according to some embodiments of the present disclosure. Experiments were performed over CZA+A|Cu/BEA and CZA+A+Cu/BEA at 220° C. The $SV_{CO}$ and absolute reaction pressure were 0.3 or 0.8 $g_{CO}$-$g_{CZA+A}^{-1}$-$h^{-1}$ and 430 or 740 kPa, respectively.
Figure 5B:
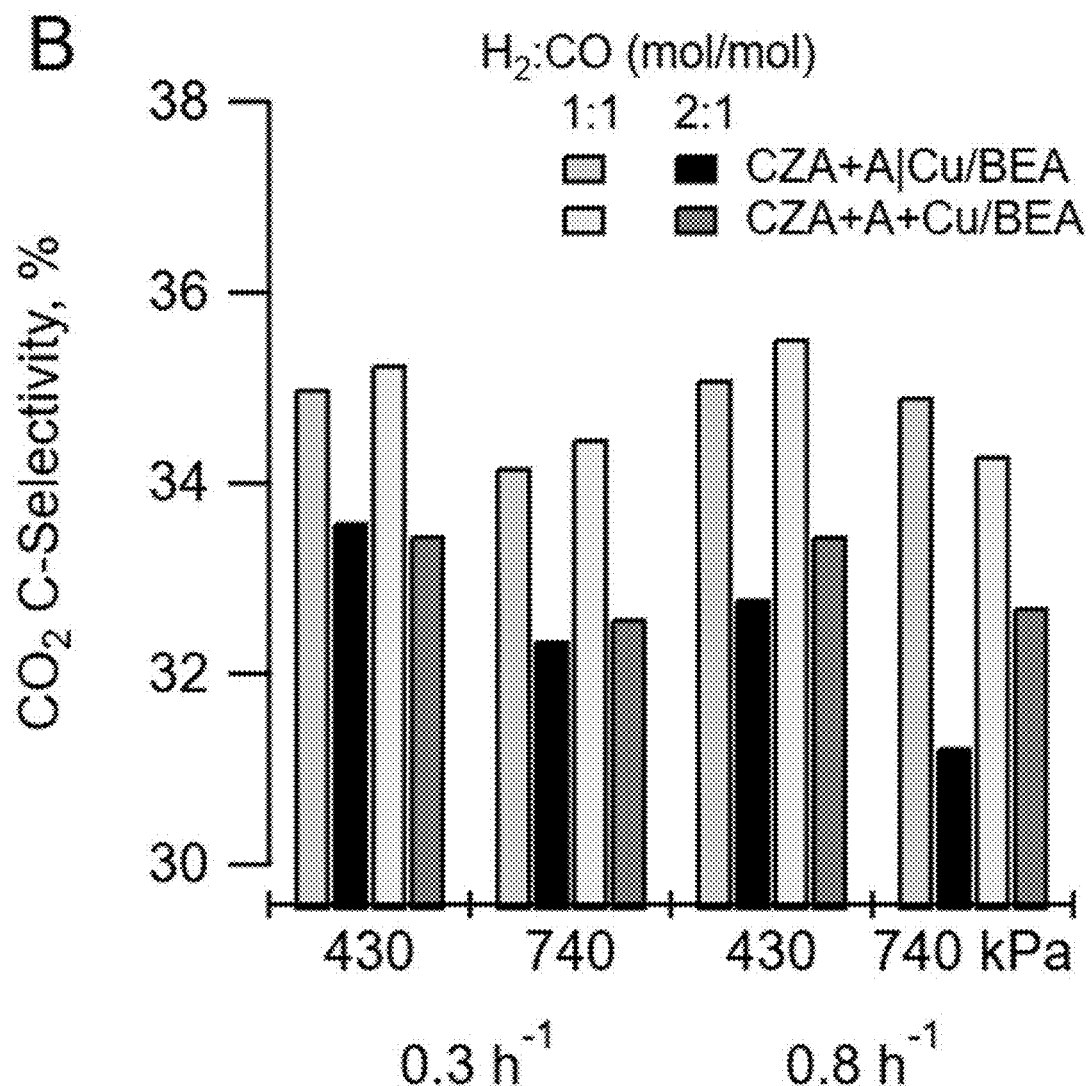
Figure 5C:
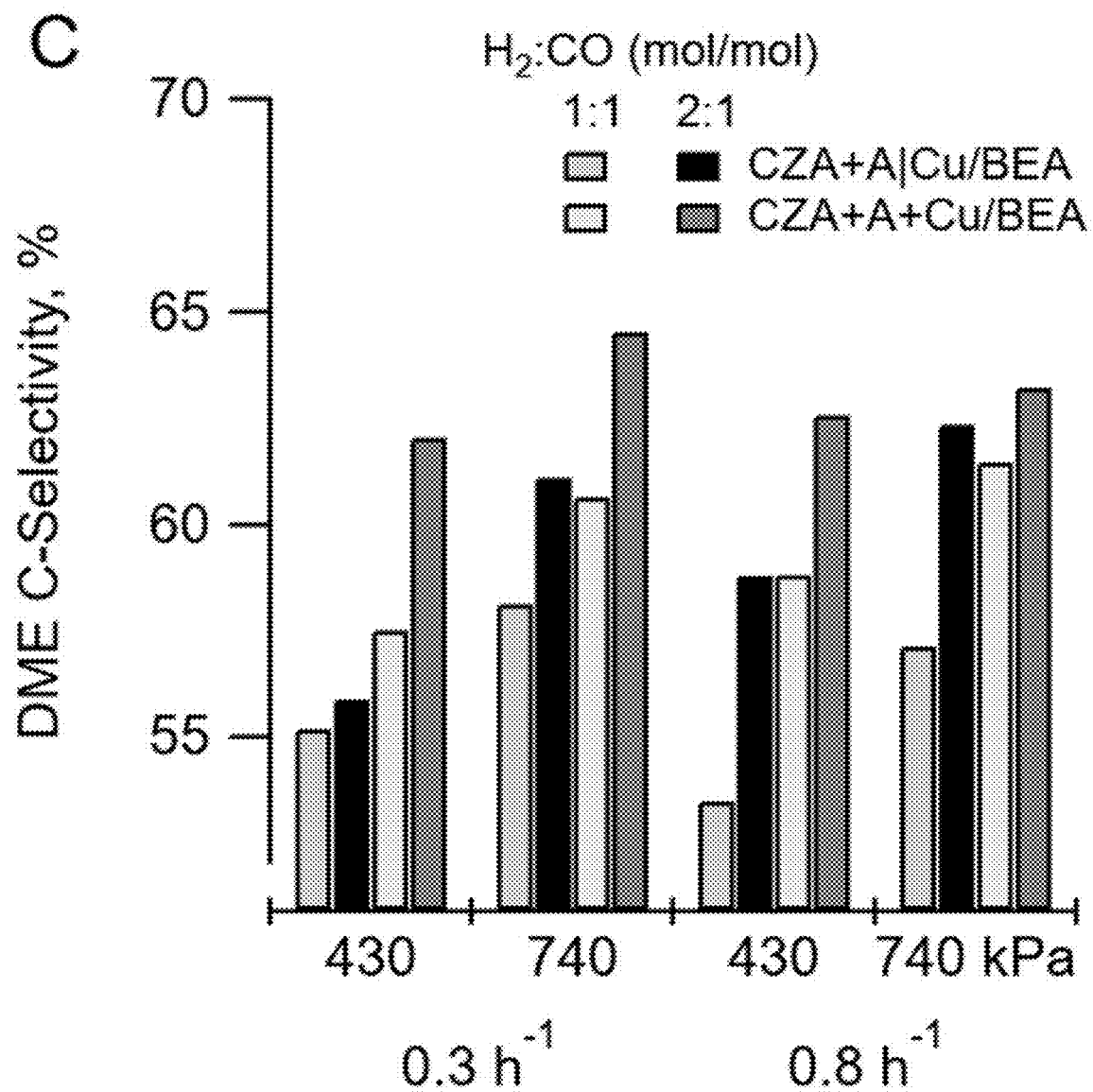

Hydrogen to carbon monoxide ratio: In initial experiments, the selectivity to $CO_2$ from WGSR was between 34% and 36%, which was among the highest of all carbon-containing products. Approaches to minimize the formation of $CO_2$ would have beneficial effects on the overall carbon efficiency of the process. Increasing the $H_2$:CO ratio should shift the WGSR reaction (Reaction 4) towards CO, leading to reduced $CO_2$ selectivity. Calculations for Reactions 1, 2 and 4 across all conditions explored here (T, P, $H_2$ to CO feed ratio) indicate an equilibrium $CO_2$ selectivity between 42% and 50%, suggesting that the WGSR did not reach equilibrium in these experiments. The effect of $H_2$:CO ratio on hydrocarbon yield was investigated at 1:1 and 2:1. The reaction temperature was 220° C., pressure was 430 or 740 kPa, SV was 0.3 or 0.8 $g_{CO} \cdot g_{CZA+A}^{-1} \cdot h^{-1}$, and two bed configurations were tested: CZA+A|Cu/BEA and CZA+A+Cu/BEA. For the stacked catalyst bed, increasing the $H_2$:CO ratio from 1:1 to 2:1 had little effect on the $C_{4+}$ hydrocarbon yield (see FIG. 5A). For the mixed catalyst bed, there was a more substantial effect, where a relative decrease of ca. 50% was observed for the $C_{4+}$ hydrocarbon yield. Towards the goal of decreasing the $CO_2$ selectivity, increasing the $H_2$:CO ratio was effective at shifting the WGSR equilibrium toward CO, as evidenced by the small but consistent decrease in $CO_2$ selectivity of ca. 1.5% at each condition (see FIG. 5B). Equilibrium calculations suggest an absolute decrease of 3 or 5% could be achieved at 430 or 740 kPa, respectively. Interestingly, increasing the $H_2$:CO ratio led to increased DME selectivity for both catalyst configurations under all conditions, up to a maximum absolute difference of 5.3% relative to the 1:1 $H_2$:CO condition (see FIG. 5C), mixed catalyst bed, 0.3 $h^{-1}$, 430 kPa). The observation of unreacted DME suggests that a greater content of Cu/BEA in the catalyst composition may be needed when operating with greater $H_2$:CO ratios to fully convert the DME intermediate to improve the $C_{4+}$ hydrocarbon yield.

Increasing HOG yield from CO-Catalyst Composition: The intermediates between syngas and hydrocarbons, MeOH and DME, were observed as products for both catalyst bed configurations and all conditions described above, suggesting that a catalyst composition with a greater Cu/BEA content may enable full conversion of these oxygenate intermediates and a correspondingly greater hydrocarbon yield. Towards this end, the catalyst composition in the stacked catalyst bed configuration was adjusted from 31:5:2 (CZA:A:Cu/BEA) to 32:5:4 and 32:5:8 (i.e., ca. 2× and 4× the base case). Performance was evaluated at 220° C., 740 kPa, with $SV_{CO}$ of 0.3 $g_{CO}\text{-}g_{CZA+A}^{-1}\text{-}h^{-1}$, and $H_2$:CO molar ratios of 1:1 and 2:1. The total mass of catalyst ($m_{CZA}+m_A+m_{Cu/BEA}$) in each experiment was held constant (ca. 3.75 g), however, the absolute mass of CZA, A and Cu/BEA varied to achieve the desired catalyst composition.

Figure 6A:
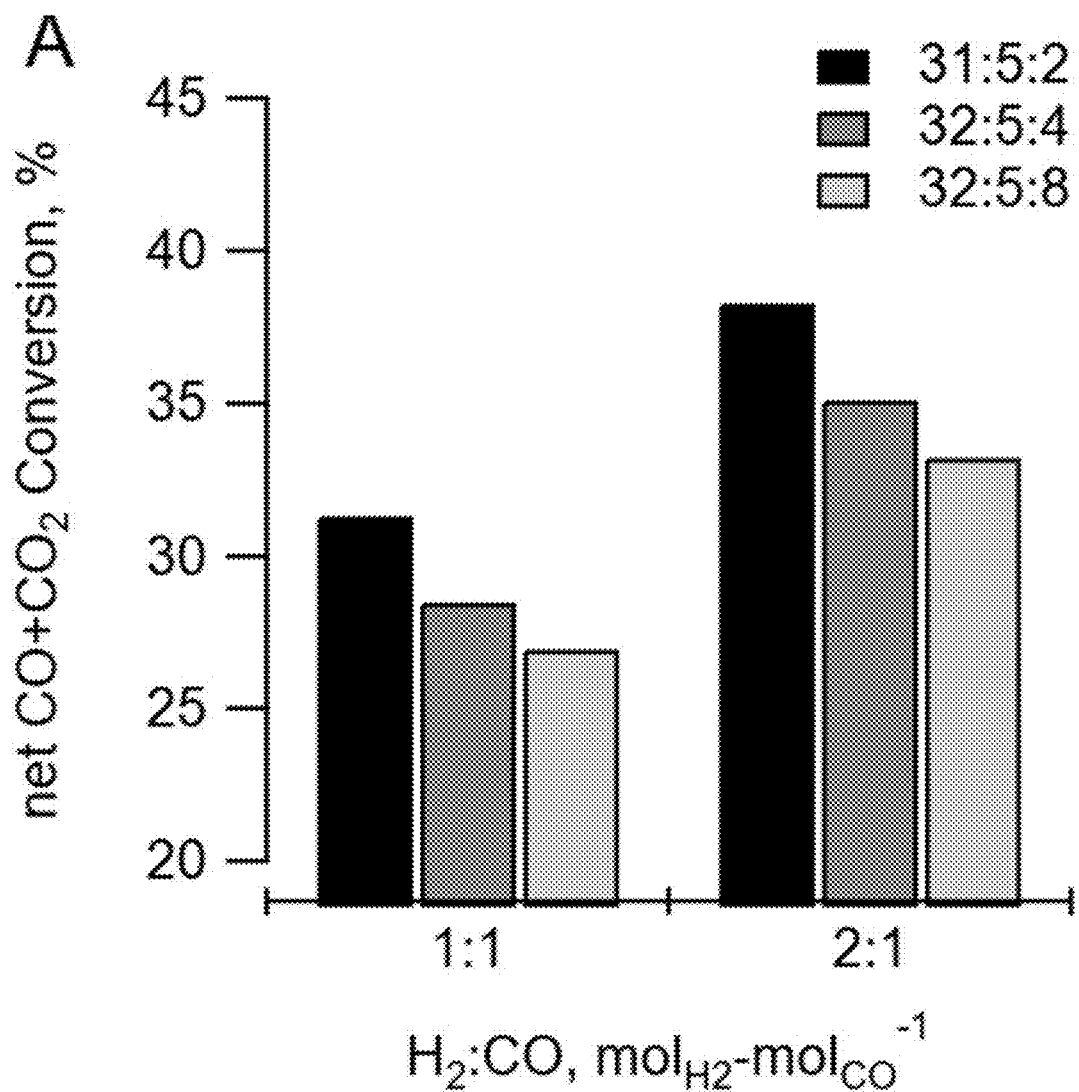
FIGS. 6A-6D illustrate the effect of greater relative Cu/BEA loadings on (A) net $CO+CO_2$ conversion, (B) gravimetric activity for DME, (C) $C_{4+}$ hydrocarbon yield, and (D) DME carbon selectivity during syngas-to-HOG reactions, according to some embodiments of the present disclosure. The catalyst compositions in the order CZA:A:Cu/BEA are listed in the legend. Experiments were performed at 220° C., 740 kPa, with $SV_{CO}$ of 0.3 $g_{CO}$-$g_{CZA+A}^{-1}$-$h^{-1}$.
Figure 6B:
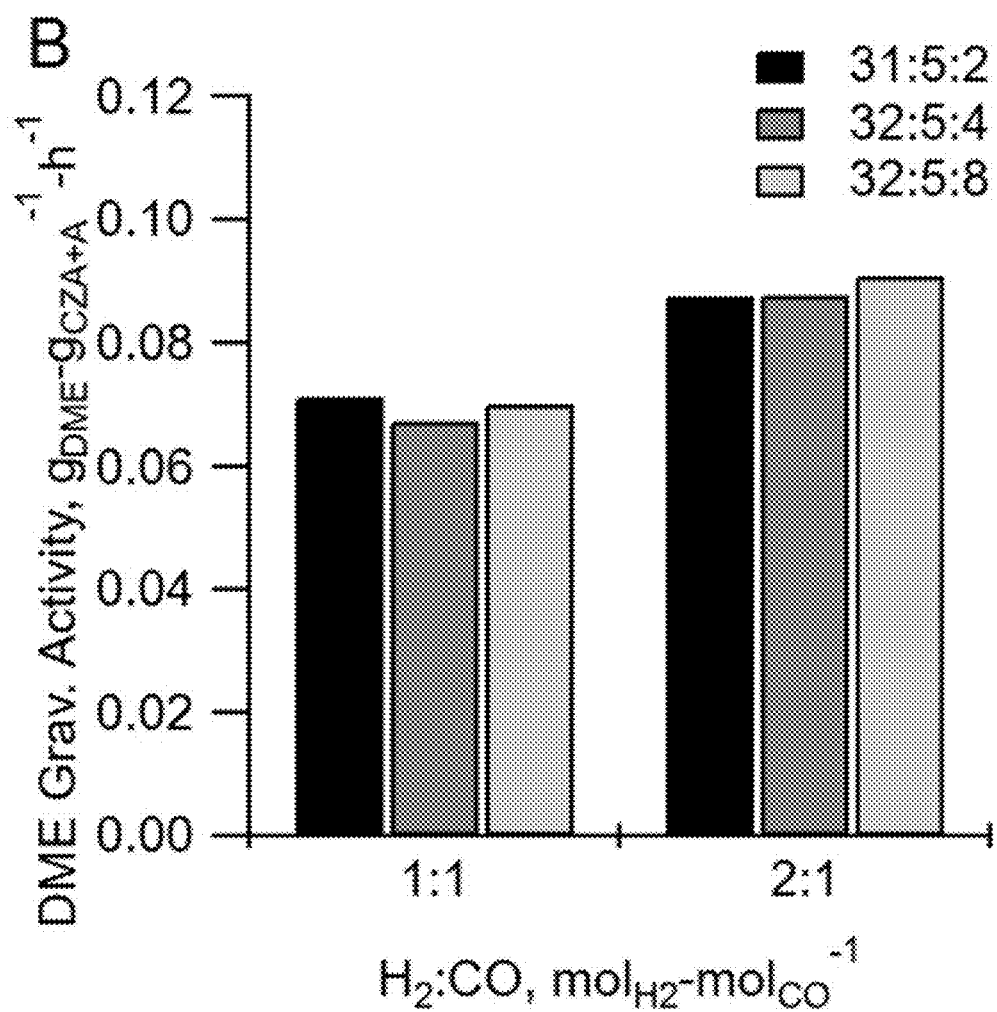

For each $H_2$:CO ratio, a decrease in the net $CO+CO_2$ conversion was observed with increasing relative Cu/BEA content, decreasing from 31.3 to 28.5 to 26.9% for the 1:1 condition and 38.3 to 35.1 to 33.2% for the 2:1 condition (see FIG. 6A). This decrease is easily explained by a decrease in the absolute mass of CZA+A loaded into the reactor. When the converted carbon is visualized as the gravimetric activity for DME formation normalized to $m_{CZA}+m_A$ (see FIG. 6B), differences in DME formation rate at a given condition are less evident, suggesting that the absolute DME formation rate can be controlled by $m_{CZA}+m_A$ in this system. The approach to equilibrium was calculated for each condition using the reaction quotient (Q) from the experimentally observed product composition and the equilibrium constant ($K_{eq}$). An approach to equilibrium ($Q/K_{eq}$) of 1.0 indicates that the reaction is at the thermodynamic limit. Values less than 1.0 indicate that the reaction has not achieved equilibrium, and values greater than 1.0 indicate that the reaction has been "pulled" past equilibrium through Le Chatelier's principle. At the 1:1 condition, $Q/K_{eq}$ values for Reaction 1 were between 0.92 and 1.25, but $Q/K_{eq}$ values for Reaction 2 were less than 0.61. Despite the observed increase in net $CO+CO_2$ conversion observed with 2:1 $H_2$:CO being in-line with the general trend predictions based on thermodynamics, the $Q/K_{eq}$ values for Reaction 1 were comparable at 0.62, 0.77, and 0.75 for the low, medium, and high Cu/BEA compositions, respectively. The $Q/K_{eq}$ values for Reaction 2 were less than 0.16 for all three Cu/BEA compositions at the 2:1 condition. That is, the MeOH to DME reaction was far below equilibrium under the conditions explored here. Considering the consistently lower $Q/K_{eq}$ values for Reaction 2 than Reaction 1, two approaches can be employed to increase the $Q/K_{eq}$ value for Reaction 2: (i) increase the relative content of A, and/or (ii) decrease the SV for CO relative to CZA+A.

Figure 6C:
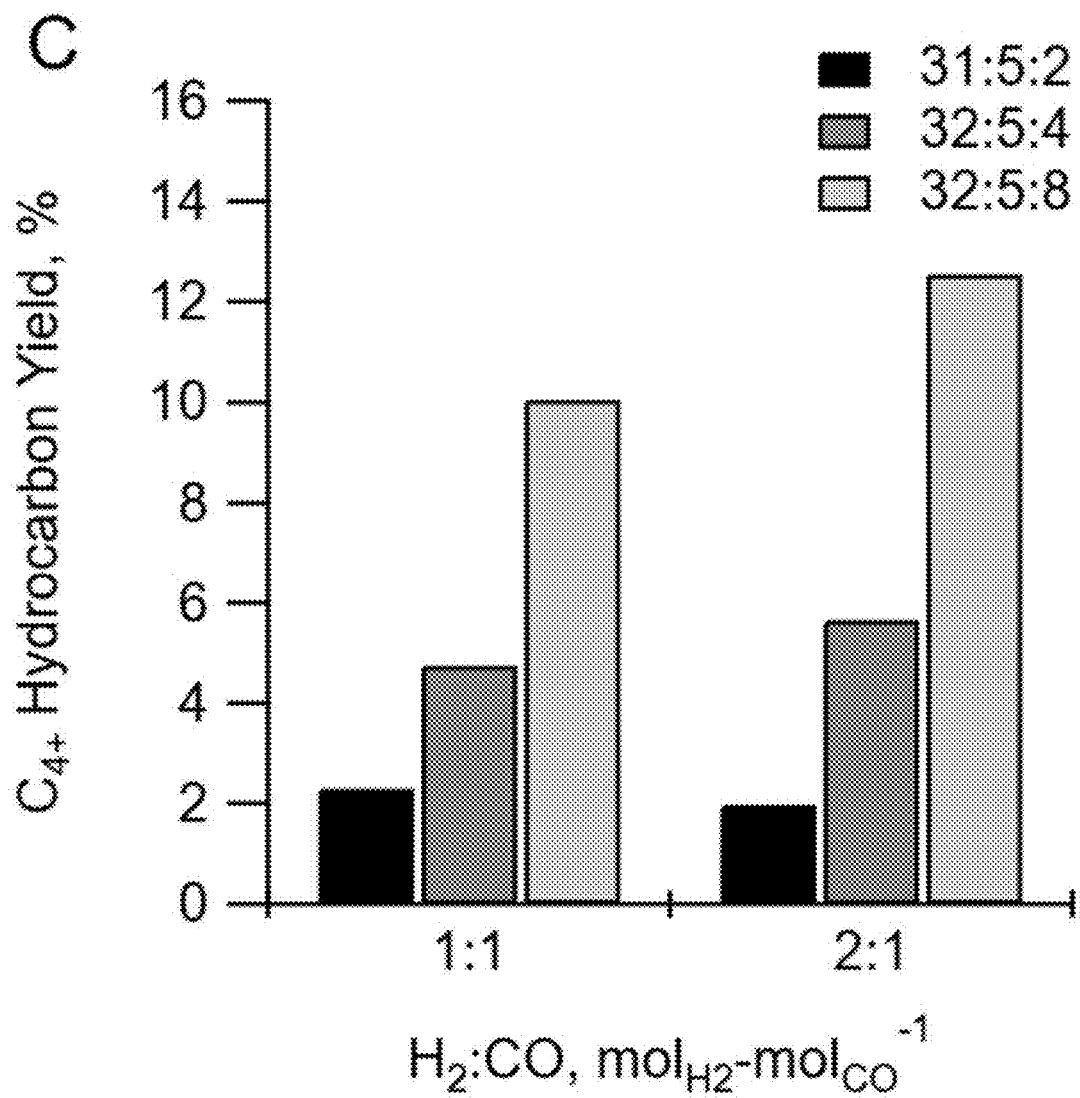
Figure 6D:
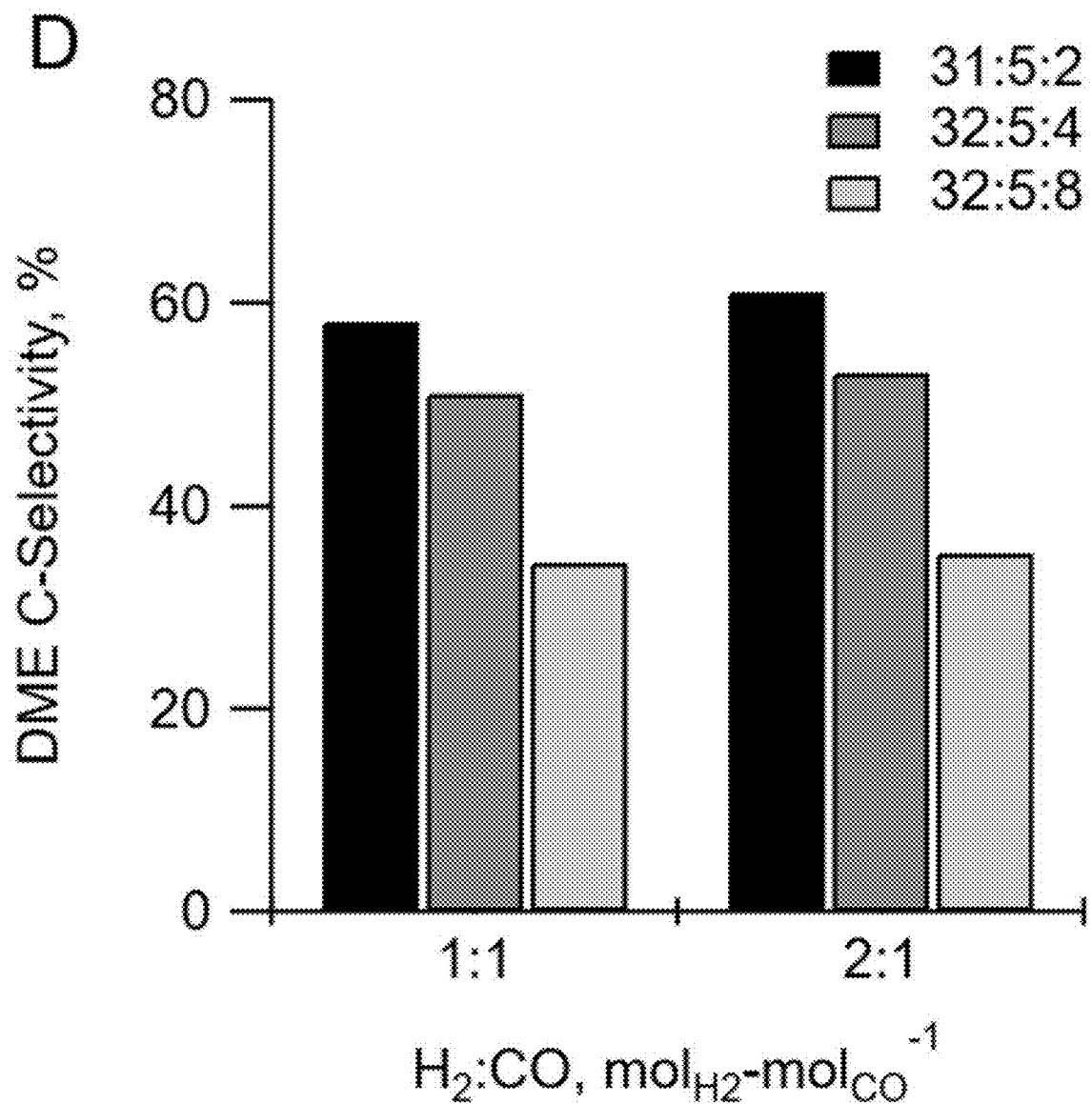

For each $H_2$:CO ratio tested, there was a marked increase in $C_{4+}$ hydrocarbon yield with greater relative Cu/BEA content, increasing from 2.3 to 4.7 to 10% for the 1:1 condition and 2.0 to 5.7 to 13% for the 2:1 condition (see FIG. 6C). The increased yield is attributed to greater conversion of intermediate DME, via Reaction 3, and supported by the observed decrease in DME carbon selectivity with greater relative Cu/BEA content (see FIG. 6D).

Figure 7:
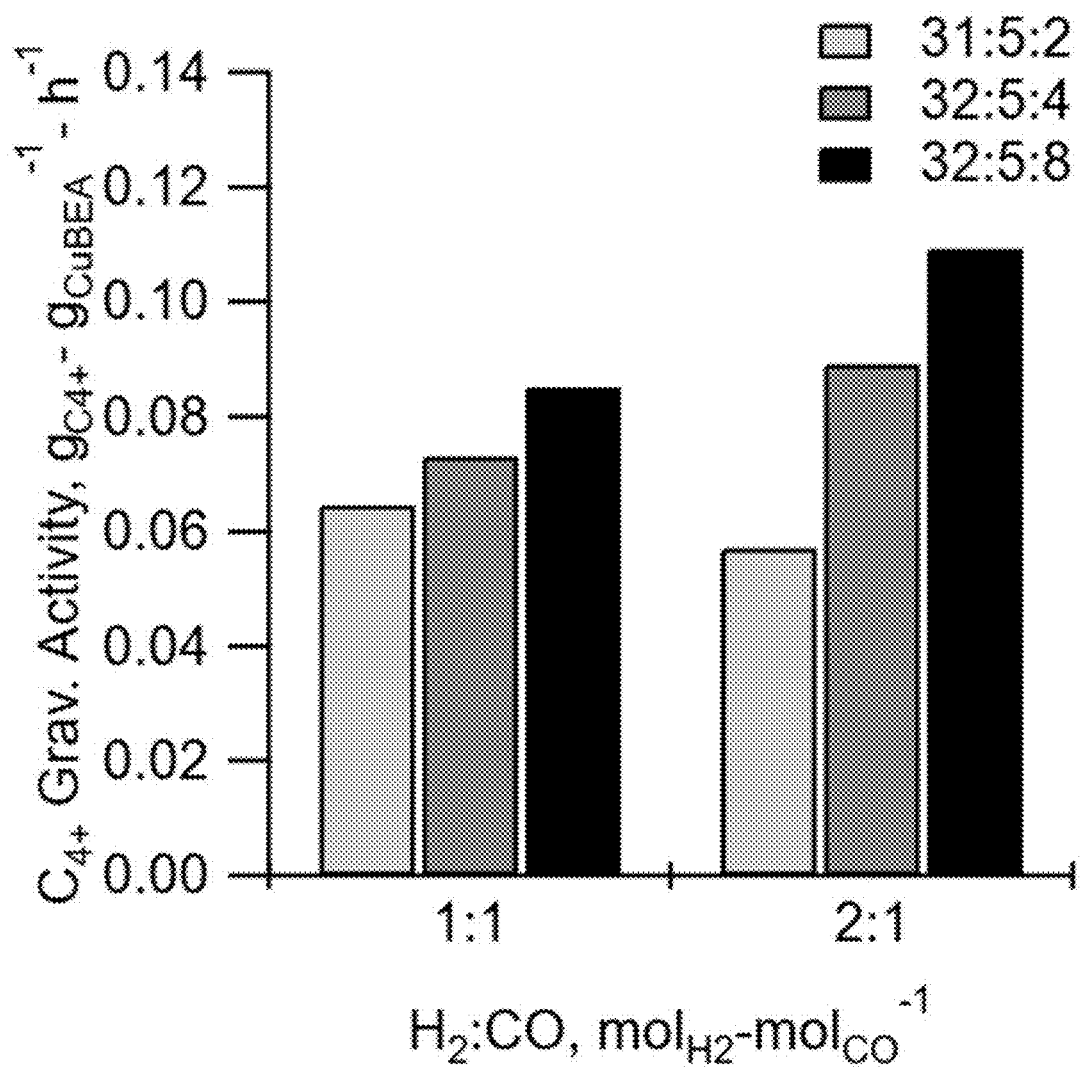
FIG. 7 illustrates the effect of greater relative Cu/BEA content on $C_{4+}$ hydrocarbon gravimetric activity during syngas-to-HOG reactions, according to some embodiments of the present disclosure. The catalyst compositions in the order CZA:A:Cu/BEA are listed in the legend. Experiments were performed at 220° C., 740 kPa, with $SV_{CO}$ of 0.3 $g_{CO}$-$g_{CZA+A}^{-1}$-$h^{-1}$. The patterned region represents typical total hydrocarbon gravimetric activity from DME-to-HOG reactions over Cu/BEA.

For both $H_2$:CO ratios, the $C_{4+}$ gravimetric activity steadily increased with increasing Cu/BEA content, from 0.065 to 0.073 to 0.085 $g_{C4+}\text{-}g_{Cu/BEA}^{-1}\text{-}h^{-1}$ for the 1:1 condition and 0.057 to 0.089 to 0.11 $g_{C4+}\text{-}g_{Cu/BEA}^{-1}\text{-}h^{-1}$ for the 2:1 condition (see FIG. 7). The highest $C_{4+}$ activity (0.11 $g_{C4+}\text{-}g_{Cu/BEA}^{-1}\text{-}h^{-1}$) observed was with the catalyst composition of 32:5:8 and a 2:1 $H_2$:CO ratio was high. In DME to hydrocarbons experiments demonstrating 0.07 $g_{C4+}\text{-}g_{Cu/BEA}^{-1}\text{-}h^{-1}$ at 220° C. and 323 kPa, the partial pressure of DME at the reactor inlet was 80-100 kPa. Here in syngas to HOG experiments, the partial pressure of DME at the reactor effluent was 2-75 kPa. Even if reacted DME is accounted for, DME partial pressure alone does not account for the increase in observed hydrocarbon formation in syngas to HOG reactions. These data demonstrate that increasing the amount of Cu/BEA relative to CZA+A in the catalyst composition resulted in greater hydrocarbon yield and gravimetric activity. It is worth noting that even at the highest hydrocarbon yields, the DME carbon selectivity was still 35%, suggesting that further increases in the relative Cu/BEA content, such as 1:1:1 CZA:A:Cu/BEA, could lead to greater hydrocarbon yields and gravimetric activity than those described herein.

Figure 8:
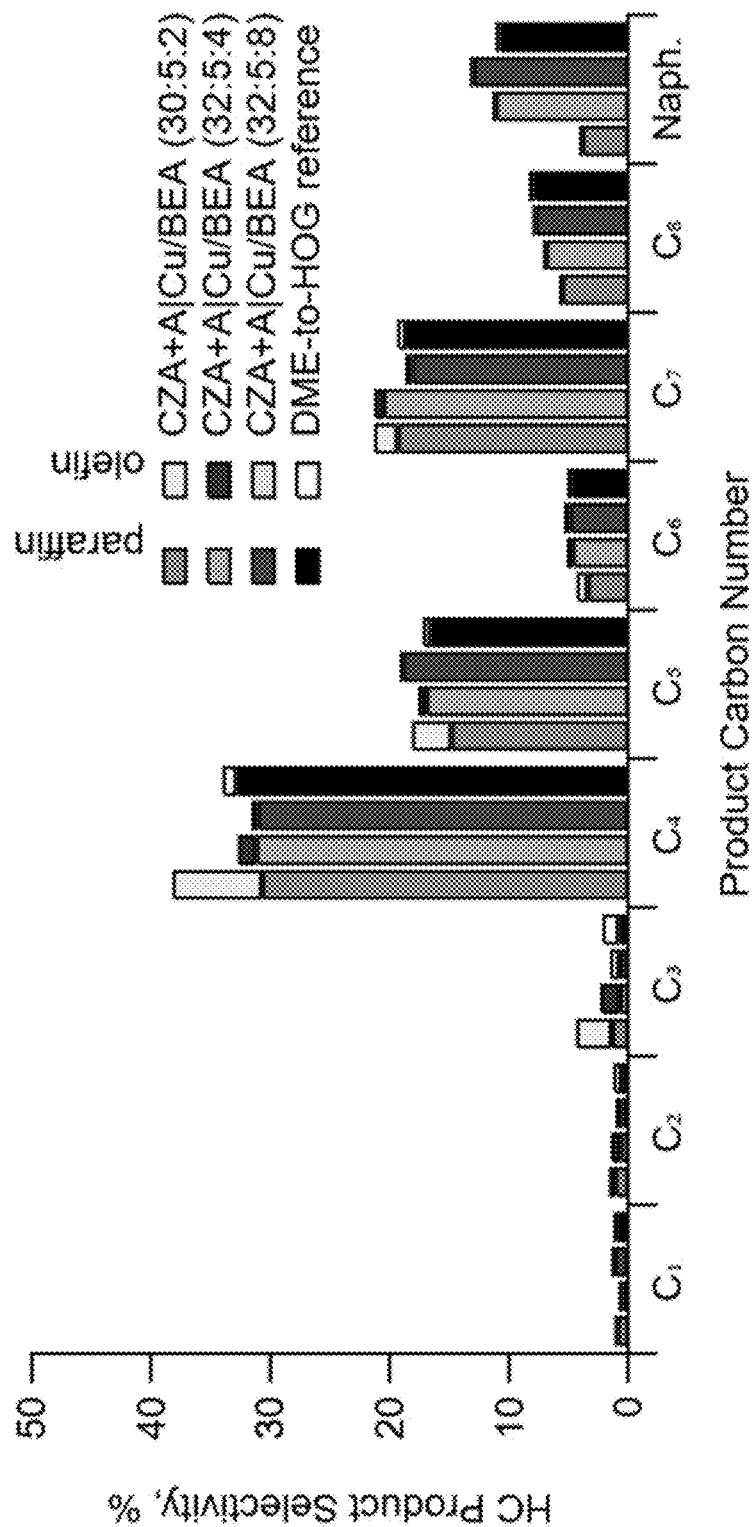
FIG. 8 illustrates carbon selectivity grouped by carbon number of hydrocarbon products comparing syngas-to-HOG over a CZA+A|Cu/BEA catalyst, according to some embodiments of the present disclosure. The catalyst compositions in the order CZA:A:Cu/BEA are listed in the legend. Syngas conversion experiments were performed at 220° C., 730 kPa absolute, $SV_{CO}$ of 0.3 $g_{CO}$-$g_{CZA+A}^{-1}$-$h^{-1}$, and $H_2$:CO=1.0 $mol_{H2}$-$mol_{CO}^{-1}$. Data for DME-to-HOG were collected at 220° C., 320 kPa absolute, with $SV_{DME}$ of 0.6 $g_{DME}$-$g_{CuBEA}^{-1}$-$h^{-1}$ and $H_2$:DME=ca. 1.0 $mol_{H2}$-$mol_{DME}^{-1}$. Carbon selectivities from syngas reactions are presented as $S_{i, oxygenate-free}$ (see Equation 6), and for DME to HOG data as $S_{i,MeOH-free}$, where only MeOH was excluded from the selectivity calculation. Carbon selectivities within a category are presented for paraffins and olefins.

The carbon selectivity of hydrocarbon products for the varying catalyst compositions at 730 kPa are illustrated in FIG. 8, with data from DME homologation with co-fed $H_2$ over Cu/BEA included for reference. Similar to the hydrocarbon product selectivity observed over the stacked catalyst beds and the mixed catalyst beds described above with varying reaction pressure and SV, it closely resembles that from DME homologation, exhibiting high selectivity to $C_4$, $C_5$ and $C_7$ products. The overall carbon number distribution did not vary appreciably with catalyst composition. The total hydrocarbon product was comprised predominantly of paraffins, with an olefin-to-paraffin ratio (O/P) less than 0.1 $mol_{C\text{-}olefin}/mol_{C\text{-}paraffin}$ for the majority of temperature and pressure conditions explored here. This is attributed to olefin hydrogenation under the high concentration of $H_2$ and in the presence of metallic Cu catalysts. The major products, $C_4$, $C_5$ and $C_7$ hydrocarbons, were essentially olefin-free, especially as the relative Cu/BEA content was increased (see FIG. 8).

Figure 9:
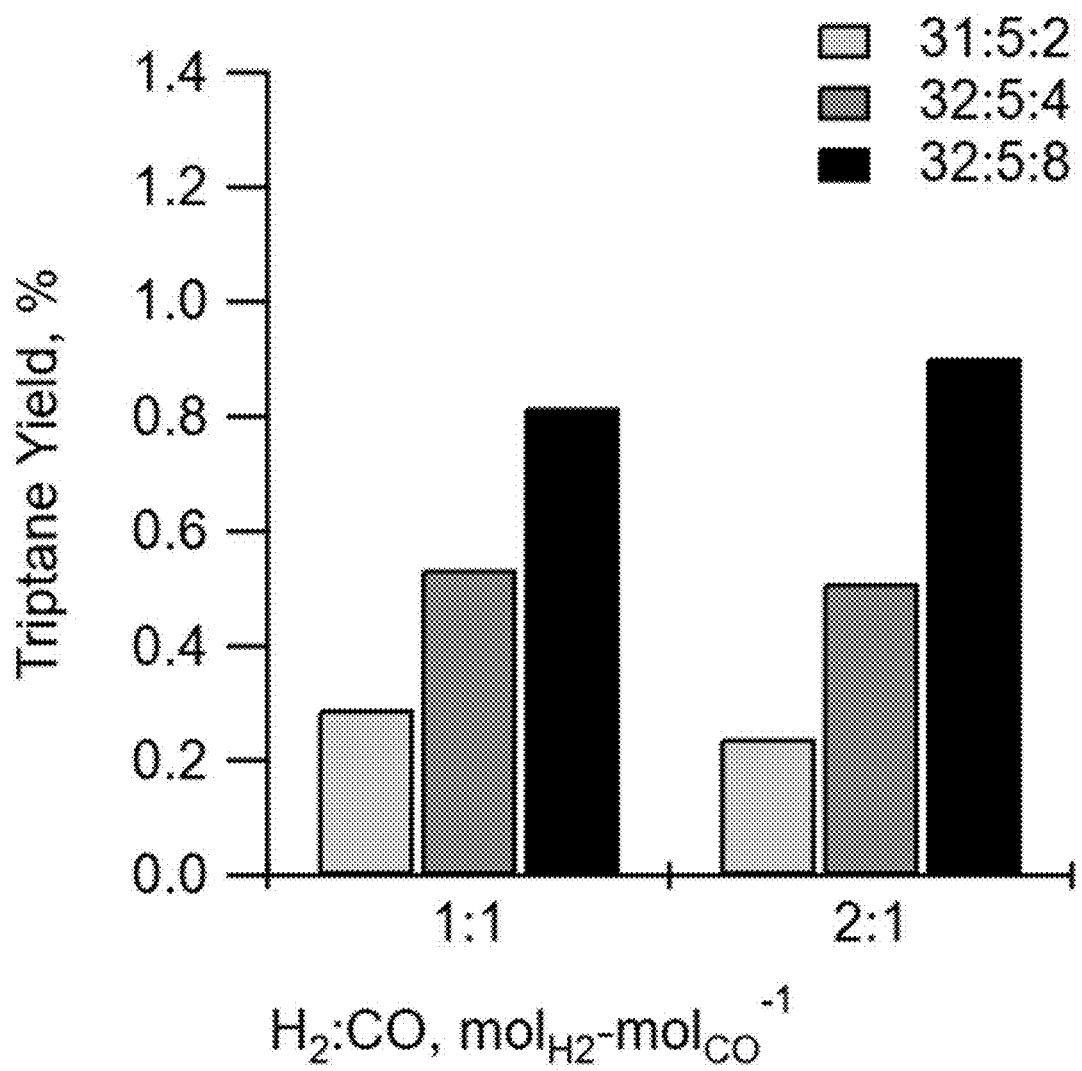
FIG. 9 illustrates the effect of increased Cu/BEA content on triptane (2,3,3-trimethylbutane) carbon yield during syngas-to-HOG reactions, according to some embodiments of the present disclosure. The catalyst compositions in the order CZA:A:Cu/BEA are listed in the legend. Experiments were performed at 220° C., 740 kPa, with $SV_{CO}$ of 0.3 $g_{CO}$-$g_{CZA+A}^{-1}$-$h^{-1}$.

Within the $C_7$ hydrocarbon products, triptane (2,3,3-trimethylbutane) is a molecule of particular interest due to its high octane rating of 113 and 101 for research and motor octane number, respectively. For both $H_2$:CO ratios, the carbon yield to triptane markedly increased with relative Cu/BEA content from 0.29 to 0.53 to 0.82% for the 1:1 condition and from 0.24 to 0.51 to 0.90% for the 2:1 condition (see FIG. 9). For reference, the triptane carbon yield from DME homologation with co-fed $H_2$ over Cu/BEA typically varies from 1.0 to 2.5%, depending on reaction temperature, pressure, and DME space velocity.

Increasing HOG yield from CO:Temperature: Another strategy toward increasing HOG yield is increasing the reaction temperature to increase the reaction rates. Stacked catalyst bed CZA+A|Cu/BEA catalysts having compositions of 32:5:4 and 32:5:8 were evaluated at three temperatures of 220° C., 230° C., and 240° C., 740 kPa, with $SV_{CO}$ of 0.3 $g_{CO}\text{-}g_{CZA+A}^{-1}\text{-}h^{-1}$, and a feed composition of 1:1 $mol_{H2}\text{-}mol_{CO}^{-1}$.

Figure 10A:
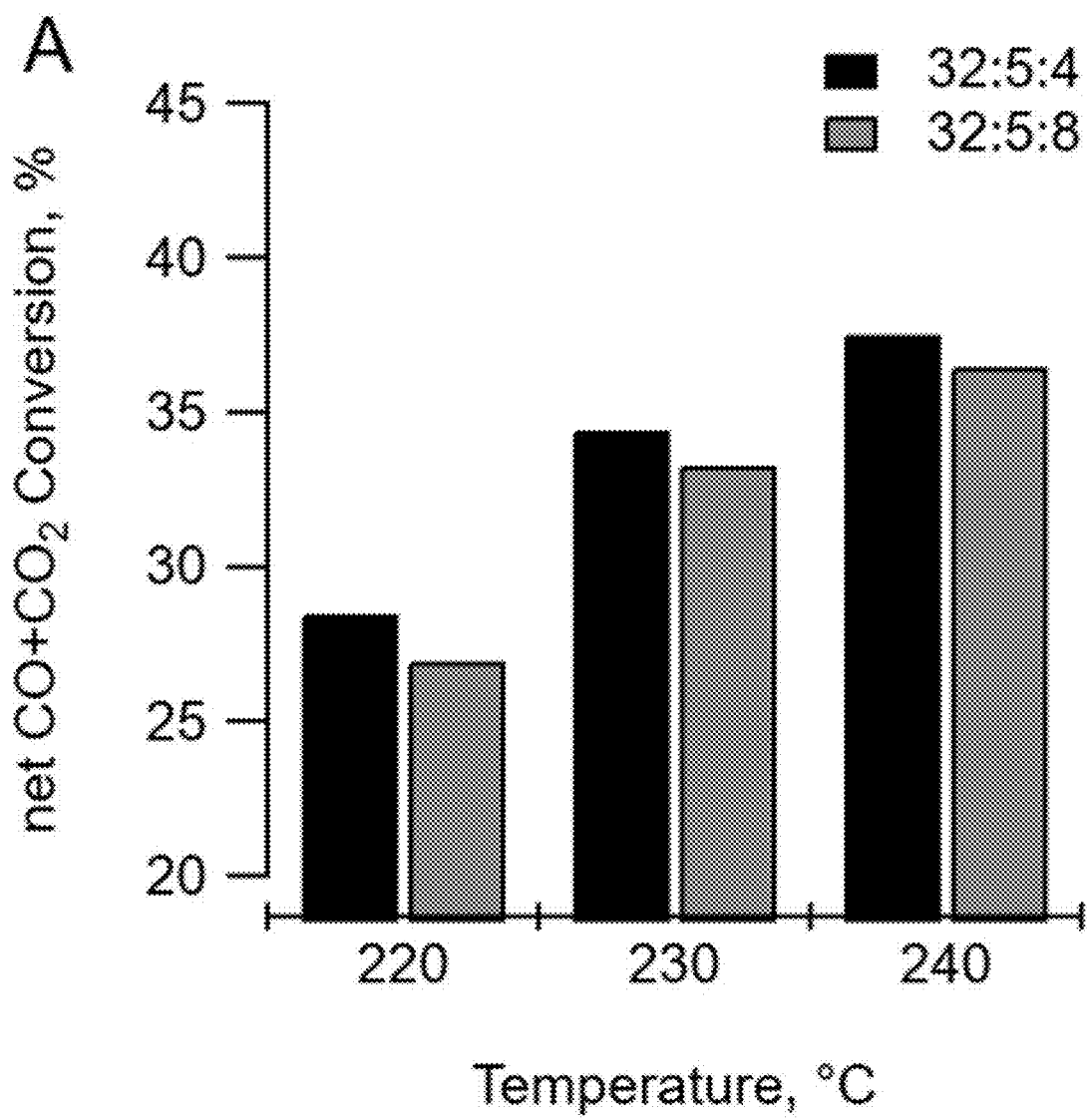
FIGS. 10A-10E illustrate the effect of temperature on (A) net $CO+CO_2$ conversion, (B) $C_{4+}$ hydrocarbon yield, (C) DME gravimetric activity, (D) DME carbon selectivity, and (E) $C_{4+}$ gravimetric activity during syngas-to-HOG reactions, with increasing reaction temperature, according to some embodiments of the present disclosure. The catalyst compositions in the order CZA:A:Cu/BEA are listed in the legend. Experiments were performed at a reaction pressure of 740 kPa, with a reactant mixture of 1:1 $mol_{H2}$-$mol_{CO}^{-1}$ at a $SV_{CO}$ of 0.3 $g_{CO}$-$g_{CZA+A}^{-1}$-$h^{-1}$.
Figure 10B:
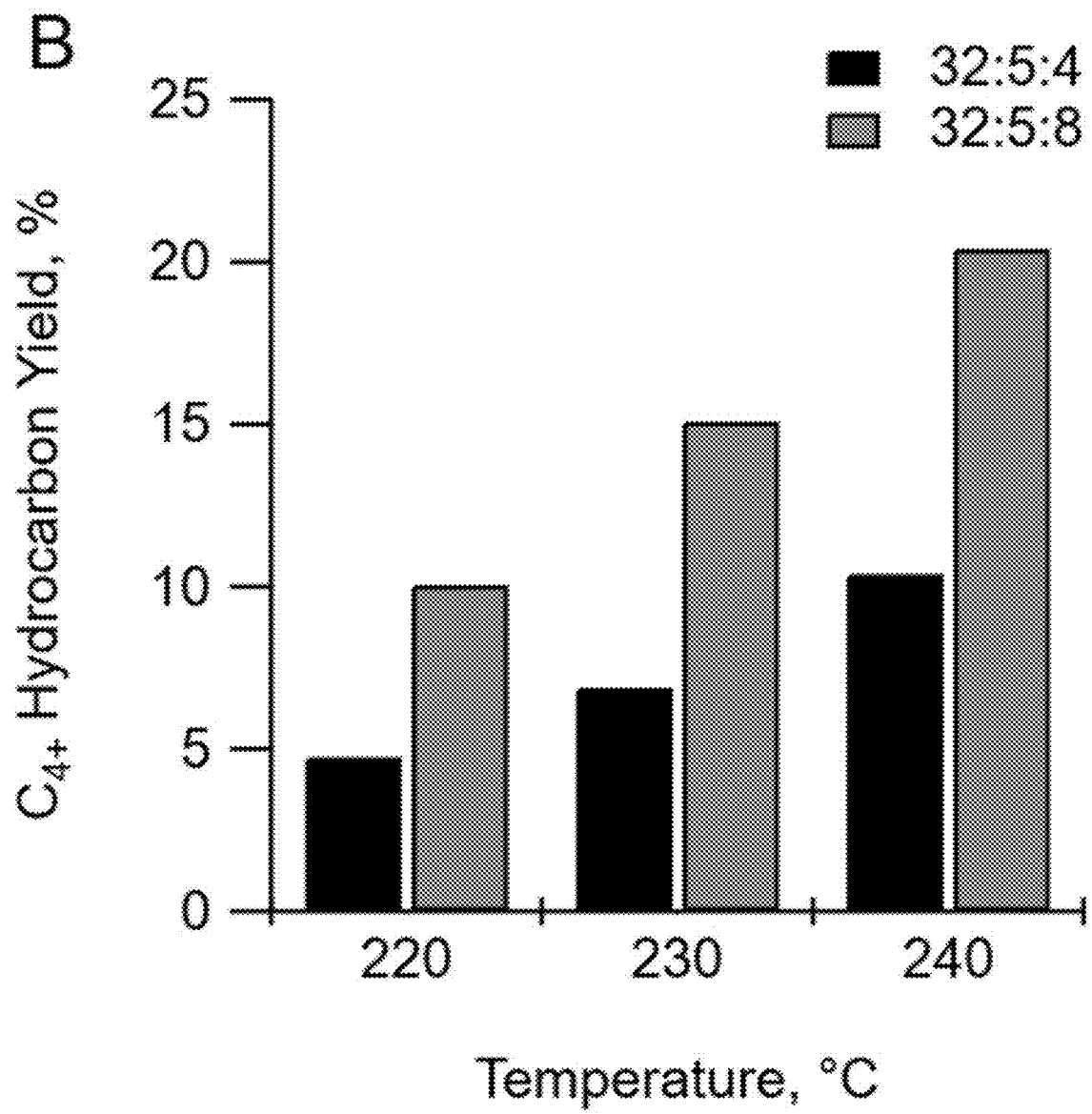
Figure 10C:
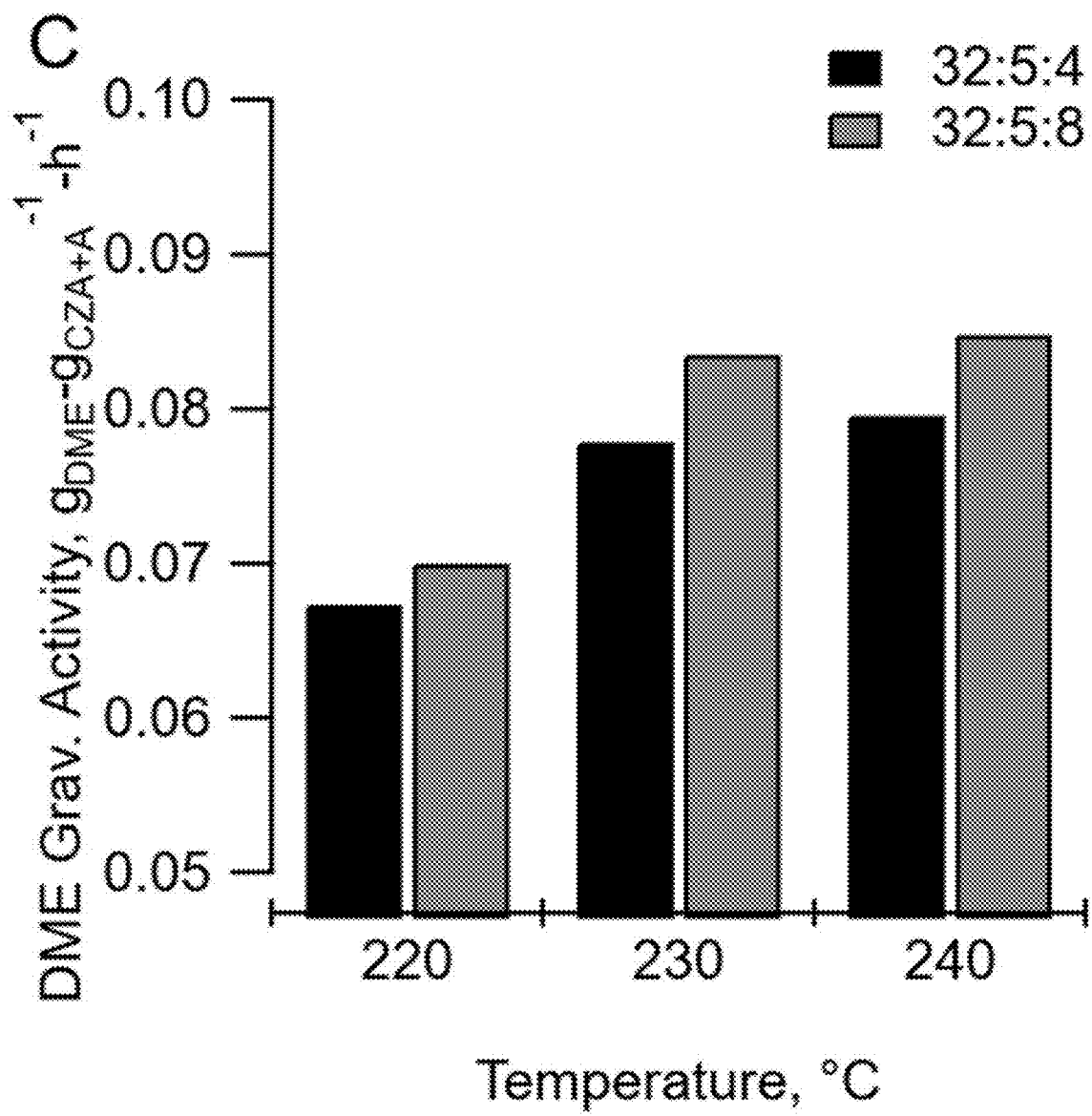
Figure 10D:
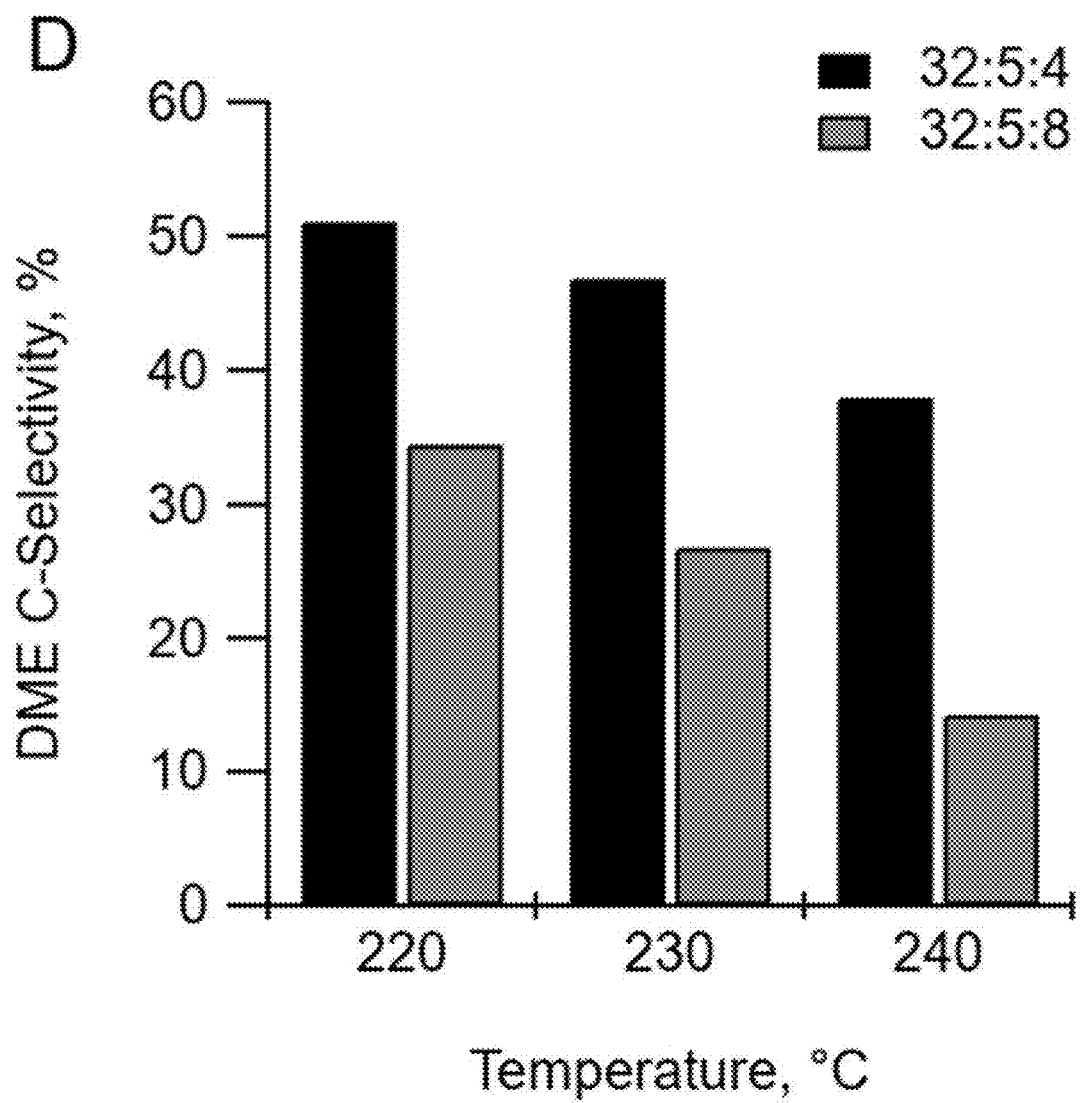
Figure 10E:
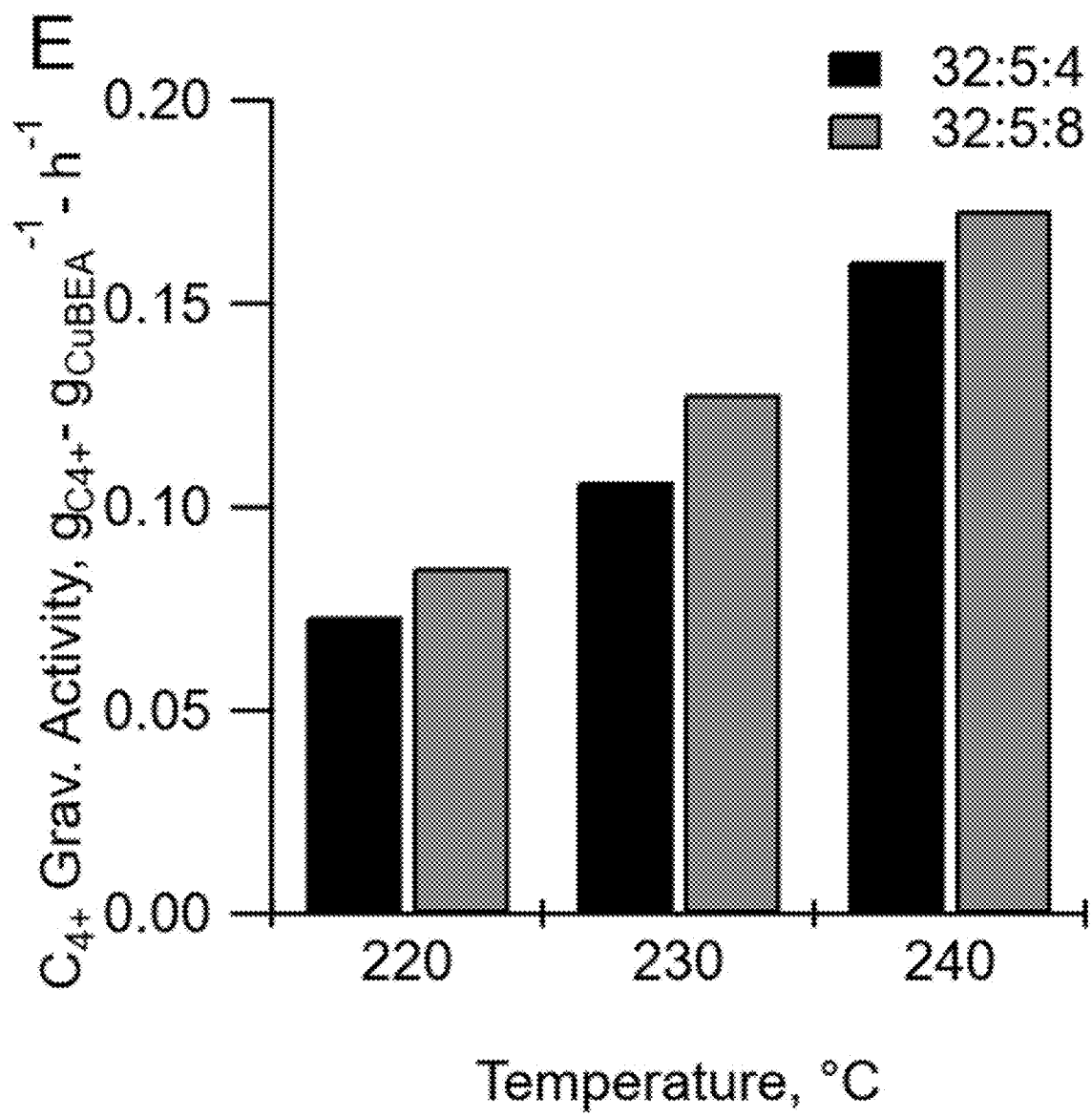

The net $CO+CO_2$ conversion increased with increasing temperature, from 28.5 to 34.4 to 37.5% with catalyst composition 32:5:4 and from 26.9 to 33.3 to 36.5% with catalyst composition 32:5:8 (see FIG. 10A). A corresponding increase in $C_{4+}$ hydrocarbon yield with increasing temperature was observed, reaching maximum values of 10.4 and 20.4% at 240° C. for catalyst compositions 32:5:4 and 32:5:8, respectively (see FIG. 10B). The observed increase in activity may be due to increased activity in Reactions 1 and 2, as evidenced by a modest increase to the DME gravimetric activity when temperature increased from 220 to 230° C. (see FIG. 10C). However, similar to as described above, this increase in hydrocarbon yield is primarily attributed to increased conversion of DME over Cu/BEA via Reaction 3 and is supported by the observed decrease in DME carbon selectivity with increasing temperature and greater relative Cu/BEA content in the catalyst (see FIG. 10D). For example, with the catalyst composition of 32:5:8, the DME carbon selectivity decreased from 35% at 200° C. to 14% at 240° C. Despite the large decrease in DME selectivity achieved under these conditions, observing DME as a product suggests that there remains opportunity for improvement of the hydrocarbon yield. Finally, the $C_{4+}$ gravimetric activity also increased with temperature, reaching maximum values of 0.16 and 0.17 $g_{C4+}$-$g_{Cu/BEA}^{-1}$-$h^{-1}$ at 240° C. for catalyst compositions 32:5:4 and 32:5:8, respectively (See FIG. 10E). These gravimetric activity values nearly double those observed from DME homologation with co-fed $H_2$ over Cu/BEA.

Figure 11A:
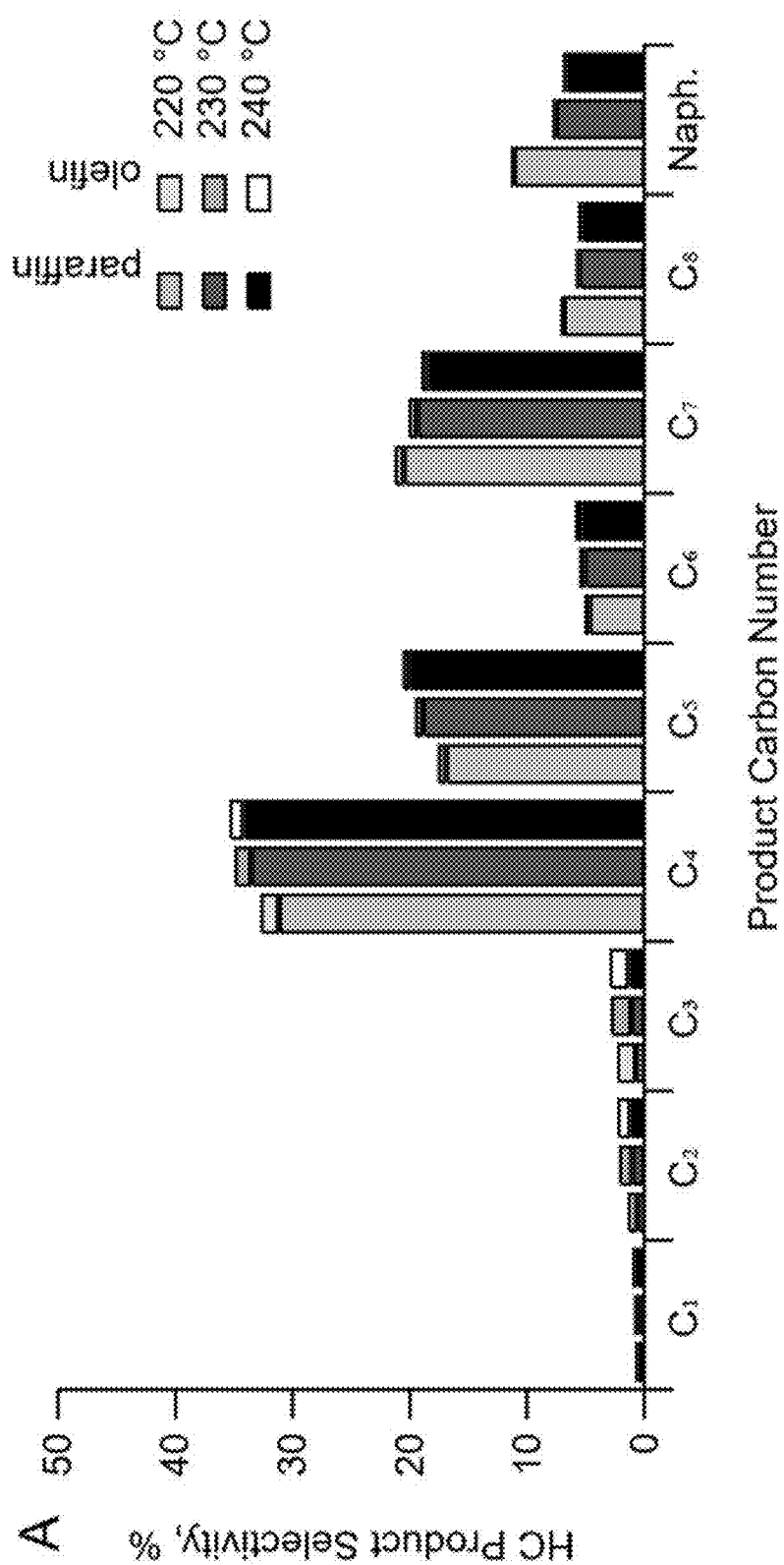
FIGS. 11A-11B illustrate the carbon number distribution from a stacked catalyst bed of CZA+A|Cu/BEA catalyst having catalyst compositions of (A) 32:5:4 and (B) 32:5:8 during syngas to HOG reactions, according to some embodiments of the present disclosure. Syngas conversion experiments were performed at 220, 230 or 240° C., 740 kPa absolute, $SV_{CO}$ of 0.3 $g_{CO}$-$g_{CZA+A}^{-1}$-$h^{-1}$, and $H_2$:CO of 1.0 $mol_{H2}$-$mol_{CO}^{-1}$. Carbon selectivities from syngas reactions are presented as oxygenate-free (Equation 6), and within a category are presented for paraffins (patterned bars) and olefins (shaded bars).
Figure 11B:
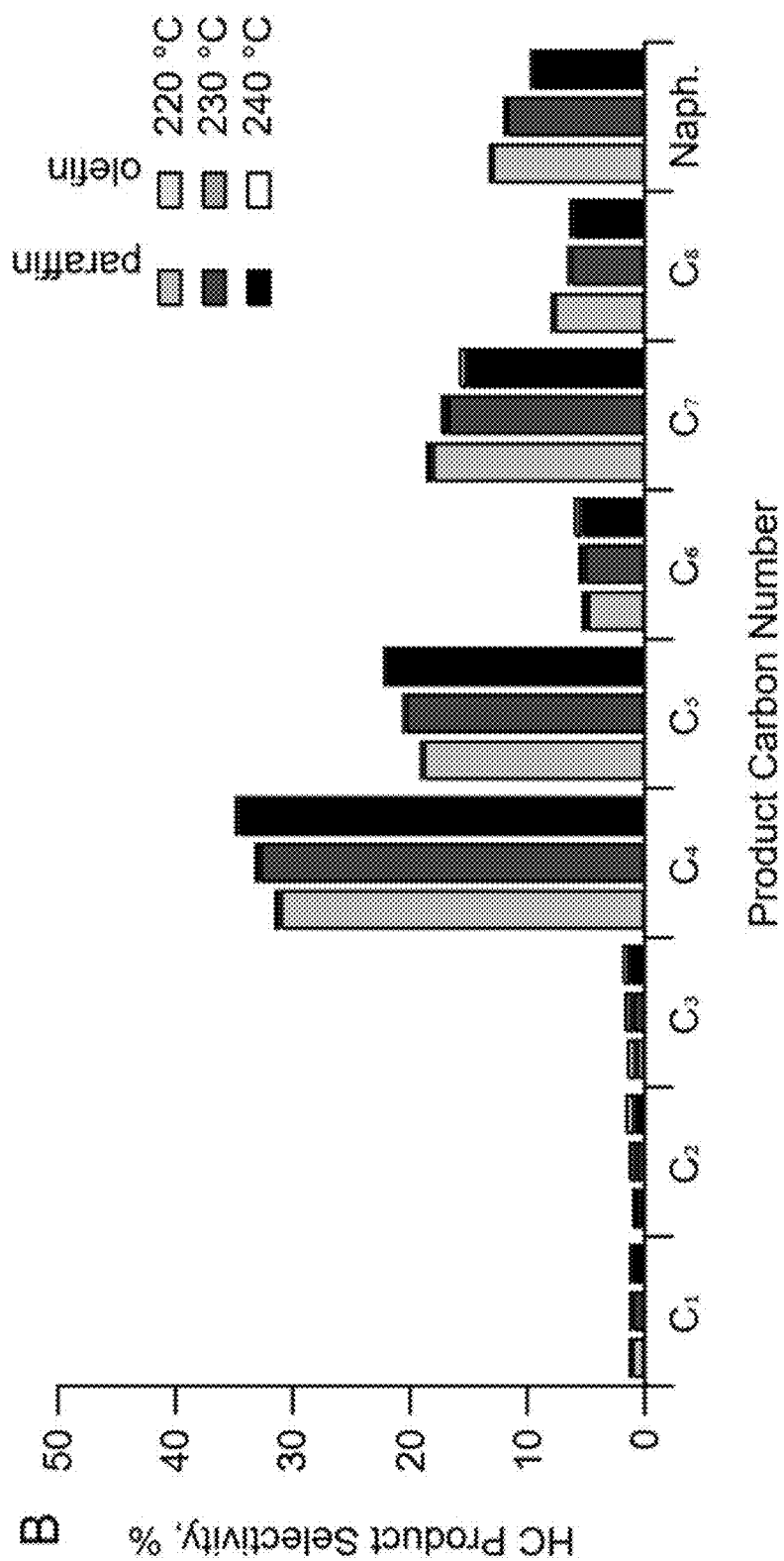

Similar to the selectivity presented above, the carbon number distribution from the reactions at higher temperature also closely resembles that from DME homologation, exhibiting high selectivity to $C_4$, $C_5$ and $C_7$ products (see FIGS. 11A and 11B). In the direct conversion of syngas to hydrocarbons over a stacked catalyst bed of CZA+A|Cu/BEA catalyst, an increase in temperature from 220° C. to 240° C. resulted in an increase in $C_4$ selectivity with an associated decrease in $C_7$ selectivity. For both catalyst compositions, increasing the temperature slightly shifted the product slate to $C_6$ and smaller hydrocarbons and away from $C_7$ and larger products. For each catalyst composition, the absolute decrease in $C_7$ selectivity was ca. 1% for each 10° C. increase in temperature. Despite the small shift in selectivity away from heavier products, the overall increases to hydrocarbon yield and gravimetric activity indicate that elevated temperature had a beneficial effect on catalyst performance.

Figure 12:
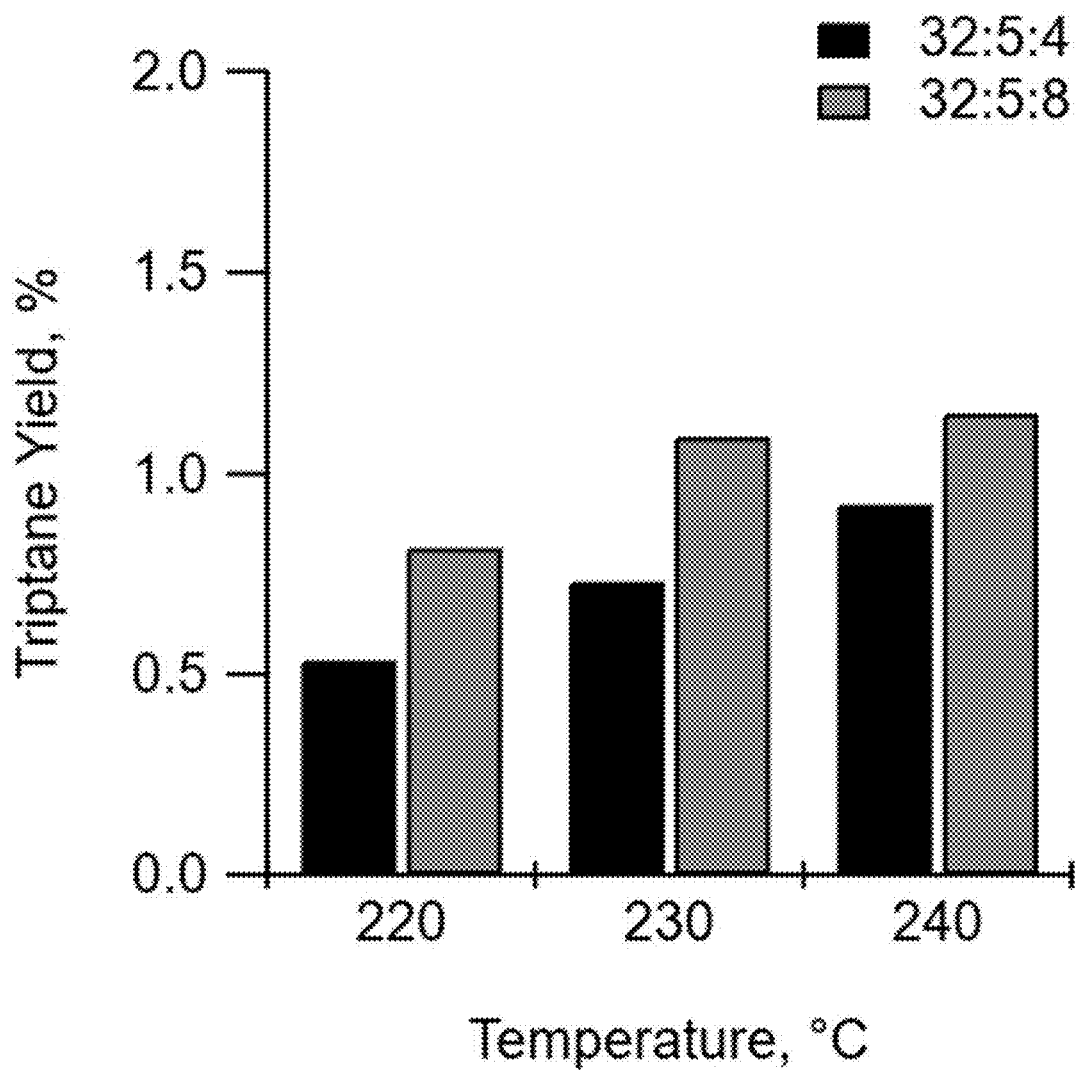
FIG. 12 illustrates the effect of reaction temperature on triptane (2,3,3-trimethylbutane) carbon yield during syngas-to-HOG reactions, according to some embodiments of the present disclosure. The catalyst compositions in the order CZA:A:Cu/BEA are listed in the legend. Experiments were performed at 740 kPa, with $SV_{CO}$ of 0.3 $g_{CO}$-$g_{CZA+A}^{-1}$-$h^{-1}$, and a feed composition of 1:1 $mol_{H2}$-$mol_{CO}^{-1}$.

Finally, despite the small shift in selectivity away from $C_7$ products, the overall increase in activity resulted in increasing triptane yield with increasing temperature (see FIG. 12). Maximum values of 0.92 and 1.1% were observed at 240° C. for catalyst compositions 32:5:4 and 32:5:8, respectively.

Increasing HOG yield from CO by increasing Pressure: Another strategy toward increasing HOG yield is increasing both the reaction temperature and pressure to increase the reaction rates. Based on the reactivity trends with increasing content of Cu/BEA in the reactor, a stacked catalyst bed CZA+A|Cu/BEA catalyst having a composition of 3:1:3 was evaluated at temperatures of between 250° C. and 320° C. (see Table 1 below), 1800-5250 kPa, with $SV_{CO}$ of 0.3-1.5 $g_{CO}$-$g_{CZA+A}^{-1}$-$h^{-1}$, and a feed composition of 2:1 $mol_{H2}$-$mol_{CO}^{-1}$.

The CO conversion remained high (>75%) across the range of temperatures and pressures employed (see Table 1). The $C_{4+}$ selectivity and per-pass $C_{4+}$ yield generally increased with increasing pressure at a given temperature until unconverted DME was observed (compare conditions 3-7 at 290° C.). When temperature and pressure were increased together, comparable C4+ selectivity, yield, and total hydrocarbon production rate could be maintained across this range of conditions. These results highlight the operational flexibility of the process to operate across a range of conditions from relatively low temperatures and pressures (conditions described above, and Conditions 1 and 2 in Table 1) through relatively high temperatures and pressures (Conditions 3-12), which are important considerations for practicing the process at the commercial scale. A maximum total hydrocarbon productivity of 0.29 $g_{HC}$-$g_{Cu/BEA}^{-1}$-$h^{-1}$ was achieved using a $SV_{CO}$ of 1.5 $g_{CO}$-$g_{CZA+A}^{-1}$-$h^{-1}$ (Condition 12).

TABLE 1

Catalytic performance data for reactions of syngas over a stacked catalyst bed of CZA + A|Cu/BEA catalysts with composition 3:1:3 at varying reaction conditions of temperature and pressure. The $SV_{CO}$ was 0.9 $g_{CO}$-$g_{CZA+A}^{-1}$-$h^{-1}$, unless otherwise noted, and the molar feed composition as 2:1 for $H_2$:CO.

| Condition | Temp. (° C.) | Pressure (kPa) | CO Conv. (%) | $C_{4+}$ Selectivity (C %) | $C_{4+}$ Yield (C %) | Total HC productivity ($g_{HC}$/$g_{CuBEA}$/h) |
|---|---|---|---|---|---|---|
| 1 | 250 | 1800 | 82.8 | 57.3 | 36.3 | 0.18 |
| 2 | 270 | 2150 | 83.2 | 59.2 | 41.3 | 0.21 |
| 3 | 290 | 2500 | 77.2 | 56.8 | 37.9 | 0.21 |
| 4 | 290 | 2840 | 79.3 | 54.8 | 35.9 | 0.20 |
| 5 | 290 | 3190 | 82.6 | 56.0 | 39.0 | 0.21 |
| 6 | 290 | 3530 | 85.7 | 55.1 | 36.7 | 0.20 |
| 7[a] | 290 | 4220 | 87.1 | 29.8 | 21.0 | 0.12 |
| 8[a] | 300 | 5250 | 88.9 | 39.6 | 28.2 | 0.17 |
| 9[a] | 310 | 5250 | 86.1 | 48.8 | 36.3 | 0.22 |
| 10 | 320 | 5250 | 82.1 | 46.8 | 34.1 | 0.21 |
| 11[a,b] | 305 | 5250 | 87.3 | 47.2 | 31.8 | 0.18 |
| 12[a,b] | 310 | 5250 | 84.9 | 48.7 | 32.3 | 0.29 |

[a]DME observed as a product under this condition at greater than approximately 5%
[b]The $SV_{CO}$ was 1.5 $g_{CO}$-$g_{CZA+A}^{-1}$-$h^{-1}$ for this condition Reactions of $CO_2$-Rich Syngas to HOG-Improving Carbon Efficiency:

In addition to approaches to minimize the formation of $CO_2$, approaches that co-convert $CO_2$ with CO would increase the overall carbon efficiency. Comparable to using the $H_2$:CO ratio to affect the WGSR equilibrium (Reaction 4), co-feeding $CO_2$ in the presence of $H_2$ should shift the WGSR reaction towards CO and enable the $CO_2$ to enter into the reaction network via conversion to CO, MeOH, and DME. Stacked catalyst beds of CZA+A|Cu/BEA catalysts having catalyst compositions of 32:5:4, 32:5:8, and 3:1:3 were evaluated at 220° C., 740 kPa, with $SV_{CO}$ of 0.3 $g_{CO}$-$g_{CZA+A}^{-1}$-$h^{-1}$, and a molar feed composition of 2:1 for $H_2$:CO without co-fed $CO_2$ and 2:1:0.8 for $H_2$:CO:$CO_2$.

Figure 13:
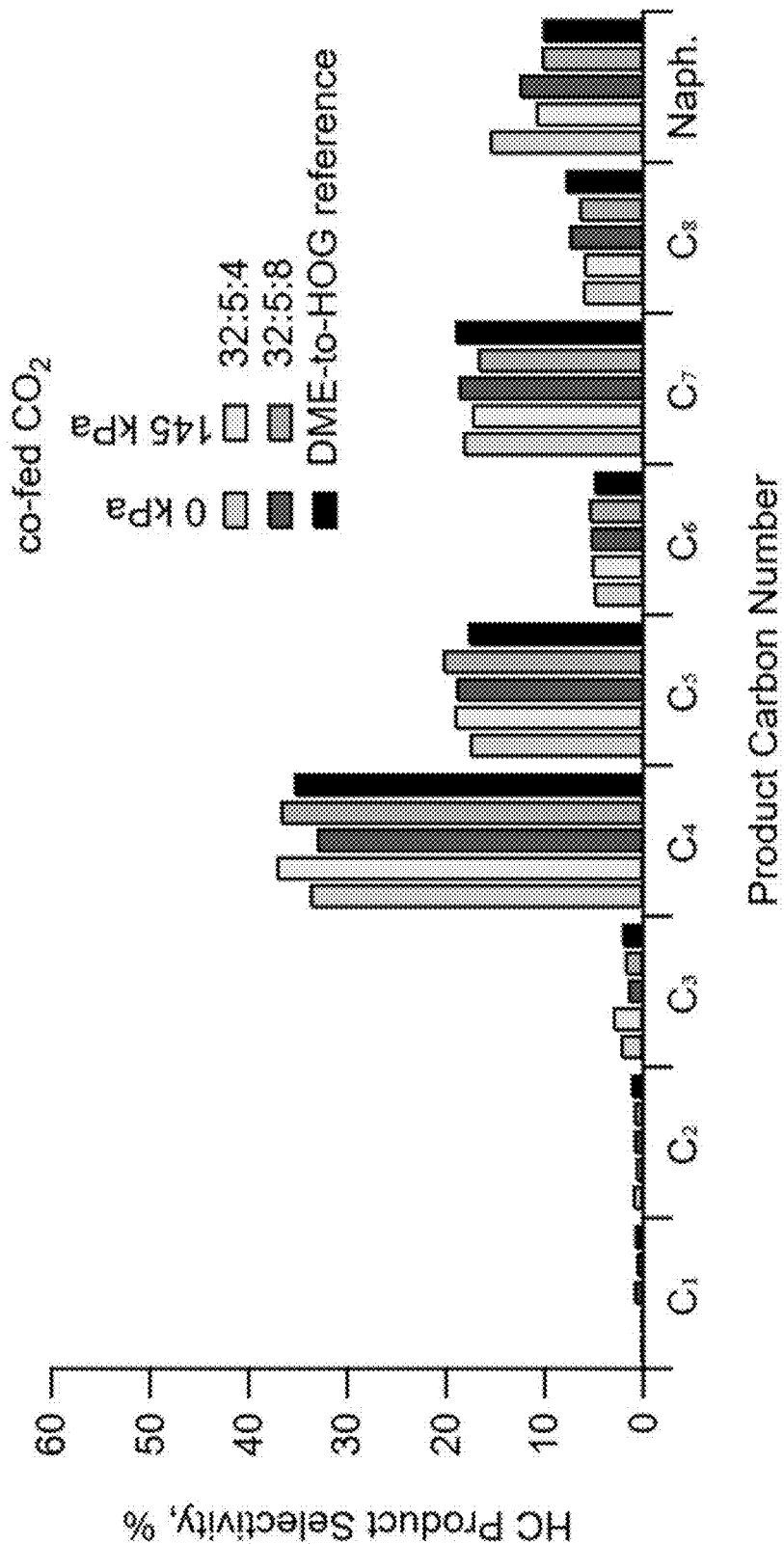
FIG. 13 illustrates hydrocarbon carbon number distribution from a stacked catalyst bed with CZA+A|Cu/BEA catalyst having compositions of 32:5:4 and 32:5:8 during syngas to HOG reactions with and without co-fed $CO_2$, according to some embodiments of the present disclosure. Reaction conditions were 220° C., 740 kPa absolute, $SV_{CO}$ of 0.3 $g_{CO}$-$g_{CZA+A}^{-1}$-$h^{-1}$. Reactions without $CO_2$ had a $H_2$:CO ratio of 2:1. Reactions with $CO_2$ had a $H_2$:CO:$CO_2$ ratio of 2:1:0.8. Data for DME to HOG were collected at 220° C., 320 kPa absolute, with $SV_{DME}$ of 0.6 $g_{DME}$-$g_{CuBEA}^{-1}$-$h^{-1}$ and $H_2$:DME=ca. 1.0 $mol_{H2}$-$mol_{DME}^{-1}$. Carbon selectivities from syngas reactions are presented as $S_{i, oxygenate-free}$ (Equation 6), and for DME to HOG data as $S_{i,MeOH-free}$, where only MeOH was excluded from the selectivity calculation.
Figure 14A:
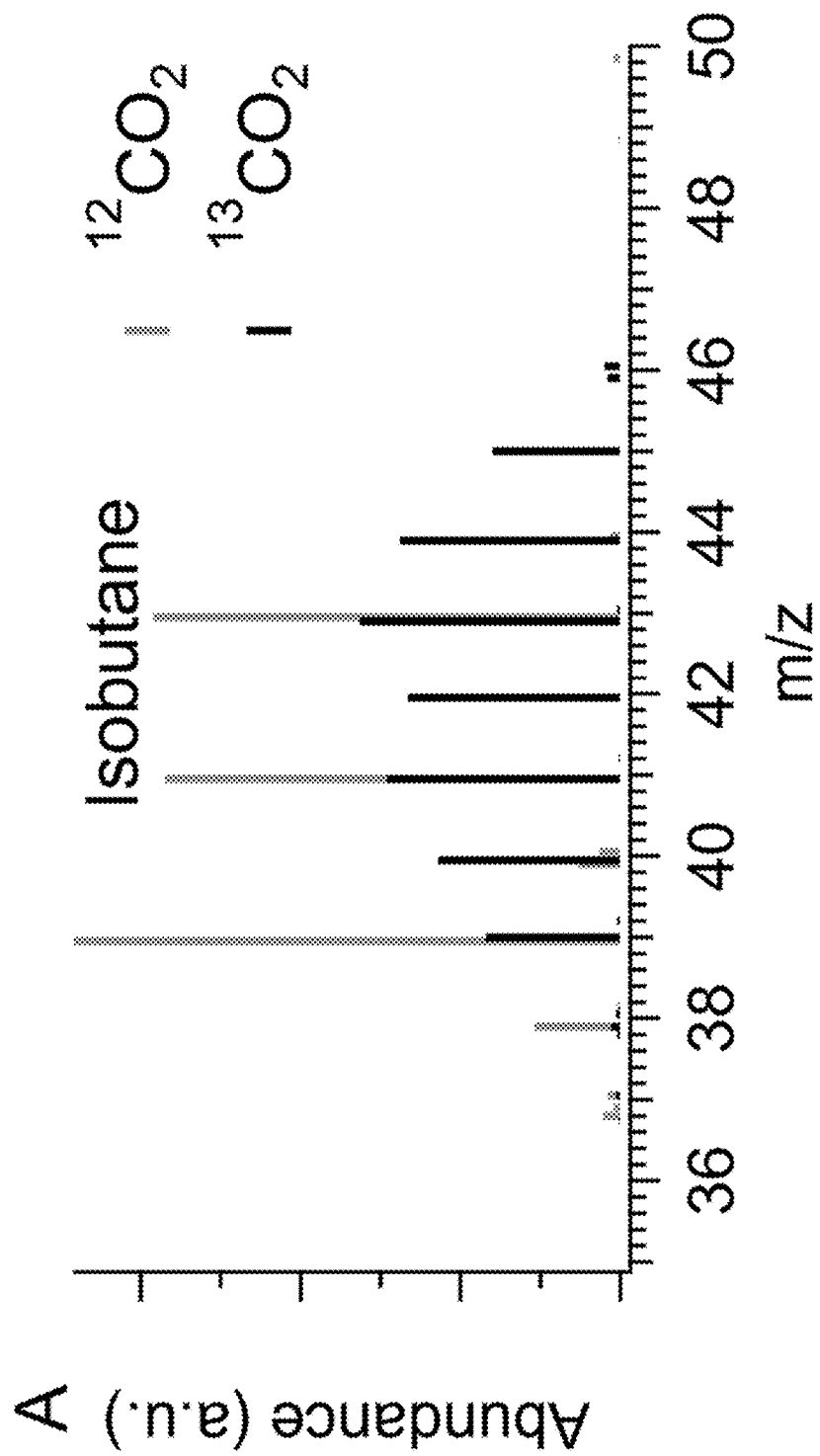
FIGS. 14A-D illustrate mass spectra of abundant $C_4$-$C_7$ products (A) isobutane, (B) isopentane, (C) isohexane, and (D) triptane from $CO_2$-rich syngas conversion over CZA+A|Cu/BEA catalyst with co-fed unlabelled $^{12}CO_2$ (gray) and isotopically-labelled $^{13}CO_2$ (black), according to some embodiments of the present disclosure. The mass peaks at greater m/z with co-fed $^{13}CO_2$ indicate $CO_2$ activation and incorporation into hydrocarbon products.
Figure 14B:
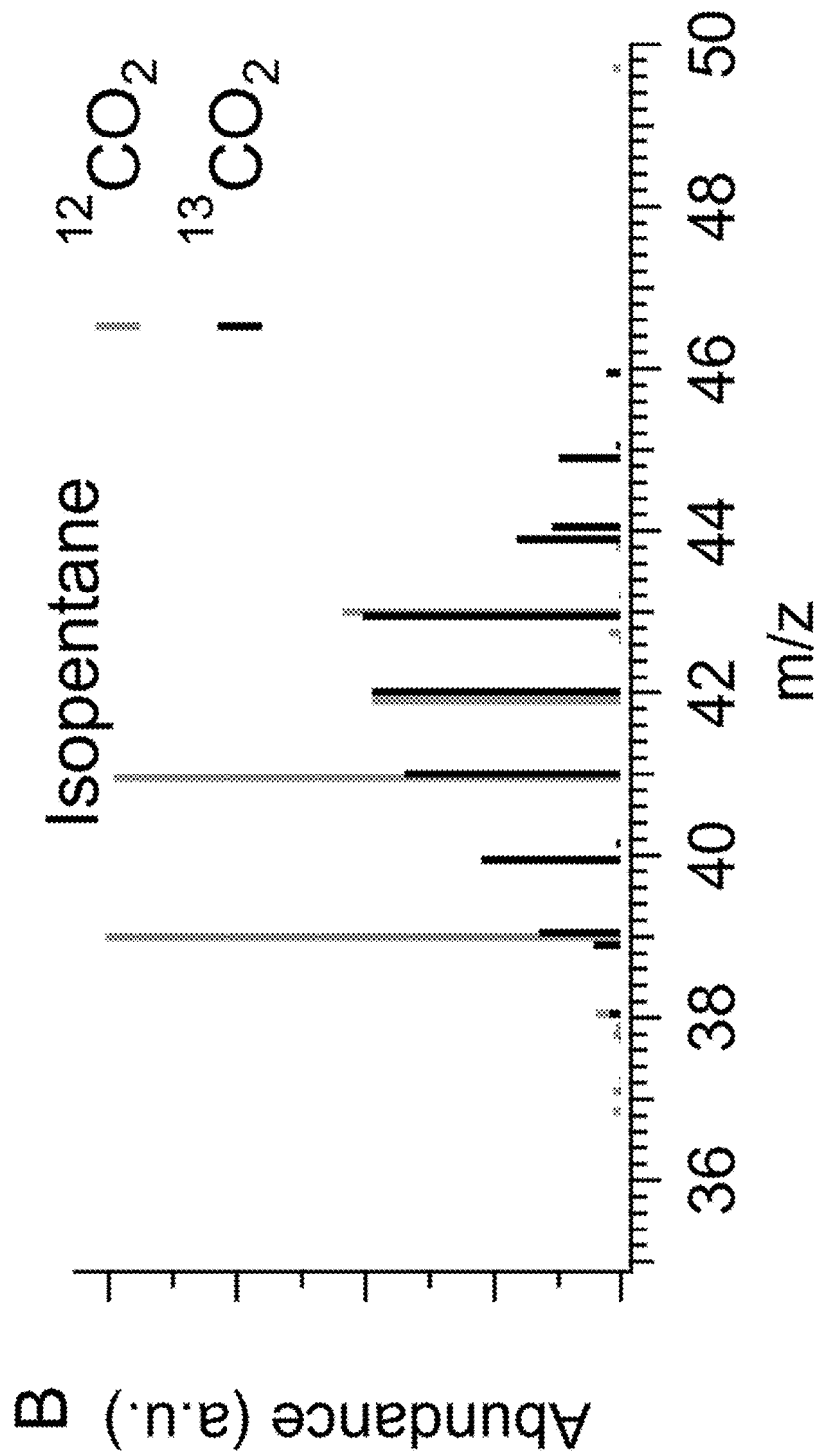
Figure 14C:
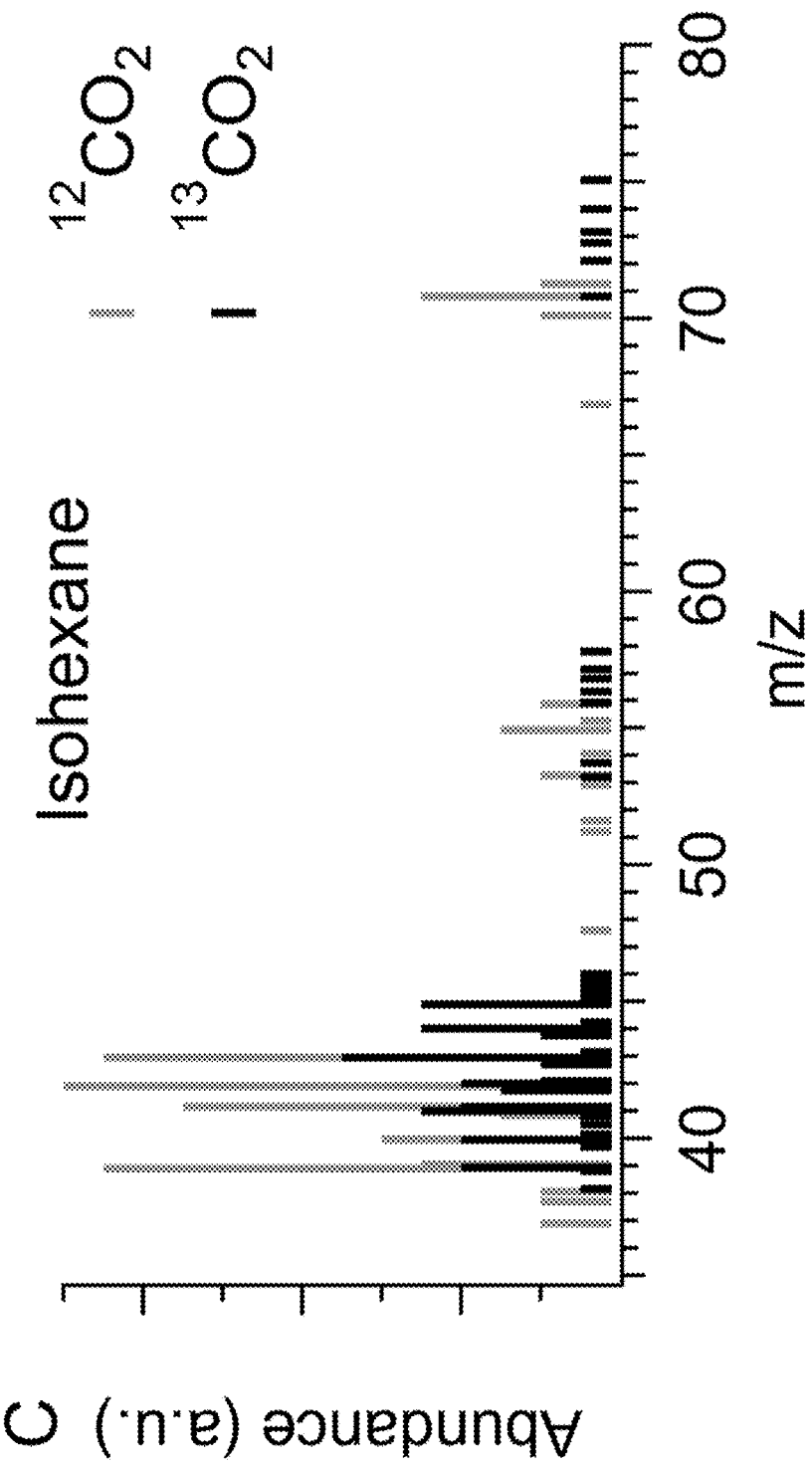
Figure 14D:
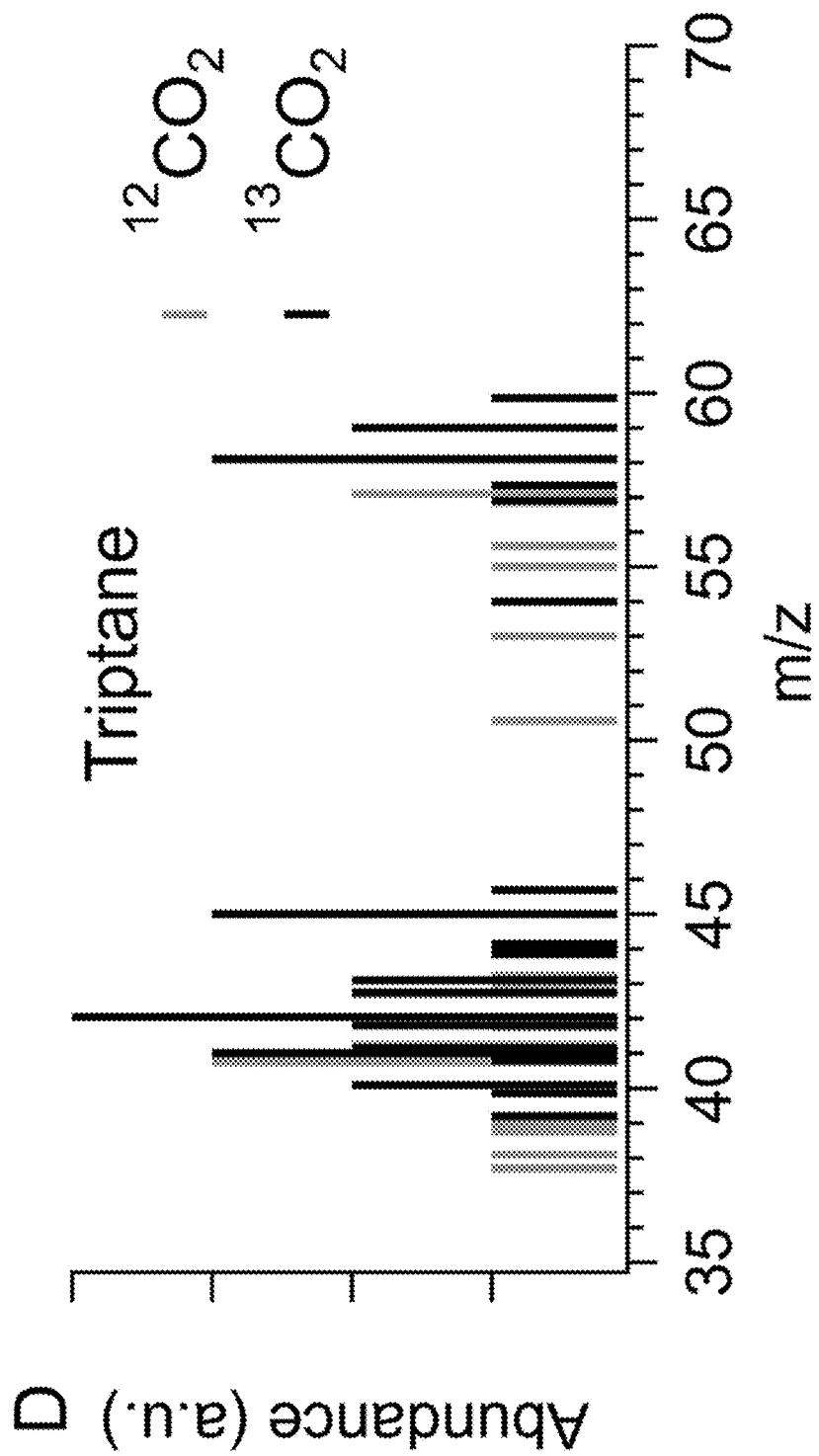

The catalytic data for reactions with co-fed $CO_2$ and comparisons to analogous experiments without co-fed $CO_2$ are presented in Table 2. Compared to catalytic performance without co-fed $CO_2$, a marked decrease in activity was observed with co-fed $CO_2$ at the relatively high ratio explored here (i.e., CO:$CO_2$ of 1:0.8). This may be due to the combination of a 20% relative decrease in CO partial pressure in experiments with co-fed $CO_2$ (e.g., CO partial pressure decreased from 225 kPa to 180 kPa with co-fed $CO_2$) and an associated doubling of the gas-hourly space velocity from 0.4 to 0.8 $cm^3$-$g_{total\,catalyst}^{-1}$-$min^{-1}$ as a result of co-feeding $CO_2$. The net CO+$CO_2$ conversion decreased to approximately one-third of the value for the syngas-only feed, accompanied by corresponding decreases in the $C_{4+}$ hydrocarbon yield and triptane carbon yield. The $C_{4+}$ hydrocarbon yield increased with increasing Cu/BEA content in the catalyst bed, with the 3:1:3 catalyst composition exhibiting per-pass $C_{4+}$ hydrocarbon yields of 44.9% without co-fed $CO_2$ and 23.8% with co-fed $CO_2$. In addition, co-fed $CO_2$ was effective in reducing the overall C-selectivity to $CO_2$. With a catalyst composition of 32:5:4, a decrease from 31.5 to 21.4% was observed. With a catalyst composition of 32:5:8, a decrease from 31.9 to 20.1% was observed. With a catalyst composition of 3:1:3, a decrease from 38.8 to 28.4% was observed. With decreasing $CO_2$ selectivity, the overall selectivity for $C_{4+}$ hydrocarbon products (i.e., $C_{4+}$ hydrocarbons among all products including oxygenates) also increased substantially, reaching 63.2% for the 3:1:3 catalyst composition with co-fed $CO_2$. The hydrocarbon product distribution from reactions with co-fed $CO_2$ were comparable to those without $CO_2$, exhibiting low selectivity to $C_{1-3}$ products (<5% total) and high selectivity to $C_4$, $C_5$, and $C_7$ products (see FIG. 13).

Mass spectra analysis with $^{13}CO_2$ co-feed: During the $CO_2$ co-feed experiment with the catalyst composition of 3:1:3, the $CO_2$ source was switched to isotopically-labelled $^{13}CO_2$ and product analysis using mass spectroscopy was employed to investigate the propagation of $^{13}C$ from $^{13}CO_2$. FIGS. 14A-14D display mass spectra for abundant $C_{4-7}$ hydrocarbon products with both unlabelled $^{12}CO_2$ and the labelled $^{13}CO_2$ co-feeds. For each of these products, peaks in the mass spectra at m/z+1 (or greater) were observed with co-fed $^{13}CO_2$ compared to the peaks observed with co-fed $^{12}CO_2$, indicative of 13C in the hydrocarbon products that originated from $^{13}CO_2$. This mass spectra analysis illustrates that $CO_2$ can be activated under these conditions, and importantly, demonstrates the feasibility for $CO_2$ to be incorporated into the hydrocarbon products. From a process standpoint, these data reduce the importance of $CO_2$ removal from syngas prior to hydrocarbon synthesis. Further, the carbon distribution data indicates that the product quality is retained, evidenced by a comparable distribution of carbon number products and isomers with high-octane ratings.

Reactions of $CO_2$ to Hydrocarbons:

Stacked versus Mixed Bed Configuration: Similar to the syngas conversion reactions, two different catalyst bed configurations were investigated: (i) a mixed catalyst bed configuration, CZA+A+Cu/BEA having a catalyst composition for CZA:A:Cu/BEA of 1:1:0.6, and (ii) a stacked catalyst bed configuration, CZA+A|Cu/BEA, having a catalyst composition for CZA:A:Cu/BEA of 1:1:0.5, respectively. Reactant flowrates were adjusted to achieve the same WHSV of 0.75 $g_{CO2}\text{-}g_{CZA+A}^{-1}\text{-}h^{-1}$ to maintain comparable $CO_2$-to-DME activity, and to study the effect of catalyst bed configuration on the subsequent MeOH and DME conversion to hydrocarbons.

Table 3 presents conversion and product C-selectivity for the reaction at 220° C. over the two bed configurations at varying pressure (at 0.5 MPa or 1.0 MPa). The $CO_2$ conversion values were similar for the two bed configurations at each studied pressure, as expected when the same WHSV with respect to CZA+A was maintained. For the mixed catalyst bed configuration, $CO_2$ conversion increased slightly with reaction pressure from 13.2% at 0.5 MPa to 14.6% at 1.0 MPa. The product selectivity was more strongly affected by reaction pressure, where an increased selectivity to MeOH (4.1 to 5.9 to 7.0%) and DME (13.7 to 22.9 to 29.1%) was observed with a decrease in CO selectivity (82.2 to 71.2 to 63.9%). This selectivity trend is consistent with the thermodynamic assessment for methanol formation (Reaction 1) at higher pressures, as discussed above. However, hydrocarbon formation from the subsequent conversion of MeOH and DME over Cu/BEA was negligible. For the stacked catalyst bed configuration, CZA+ A|Cu/BEA, a similar trend for the $CO_2$ conversion and product selectivity to MeOH, DME and CO with increasing reaction pressure was observed. The most important difference between the two bed configurations was the significant increase in the DME-to-hydrocarbon activity over Cu/BEA in the stacked catalyst bed configuration. The selectivity to hydrocarbons increased from 9.3 to 14.8% as reaction pressure increased from 0.5 to 1 MPa. The hydrocarbon products were predominantly isobutane and isopentane.

TABLE 2

Catalytic performance data for reactions of syngas with co-fed $CO_2$ over a stacked catalyst bed of CZA + A|Cu/BEA catalysts with catalyst compositions of 32:5:4, 32:5:8, and 3:1:3. Reaction conditions were 220° C., 740 kPa, with $SV_{CO}$ of 0.3 $g_{CO}\text{-}g_{CZA+A}^{-1}\text{-}h^{-1}$, and a molar feed composition of 2:1 for $H_2$:CO without $CO_2$ and 2:1:0.8 for $H_2$:CO:$CO_2$. The SV based on CO + $CO_2$ was 0.35 $g_{CO+CO2}\text{-}g_{CZA+A}^{-1}\text{-}h^{-1}$.

|  | \multicolumn{6}{c}{Catalyst composition} |
| --- | --- | --- | --- | --- | --- | --- |
| Metric | 32:5:4 | | 32:5:8 | | 3:1:3 | |
| $CO_2$ co-feed | No | Yes | No | Yes | No | Yes |
| CO + $CO_2$ conversion (%) | 35.1 | 10.5 | 33.2 | 12.5 | 77.3 | 27.0 |
| $C_{4+}$ HC yield (%) | 5.7 | 3.4 | 14.4 | 9.6 | 44.9 | 23.8 |
| Triptane yield (%) | 0.51 | 0.22 | 1.0 | 0.44 | 2.0 | 0.46 |
| $CO_2$ C-selectivity (%) | 31.5 | 21.4 | 31.9 | 20.1 | 38.8 | 28.4 |
| $C_{4+}$ C-selectivity (%) | 12.1 | 15.5 | 28.5 | 39.8 | 53.9 | 63.2 |

TABLE 3

Effect of catalyst bed configurations and reaction pressures to $CO_2$ conversion and product C-selectivity in $CO_2$ hydrogenation. Reaction conditions: 220° C., $H_2$:$CO_2$ = 3:1, WHSV = 1.5 (g $CO_2$/g CZA/h); Mixed catalyst bed: physical mixture of CZA, g-$Al_2O_3$, and Cu/BEA catalysts with catalyst composition of CZA:g-$Al_2O_3$:Cu/BEA = 1:1:0.6; A stacked catalyst bed configuration includes top bed: physical mixture of CZA and g-$Al_2O_3$; and bottom bed: Cu/BEA with catalyst composition of CZA:g-$Al_2O_3$:Cu/BEA = 1:1:0.5.

| Pressure (MPa) | 0.5 | | 0.8 | | 1 | |
|---|---|---|---|---|---|---|
| Bed configuration | Mixed | Stacked | Mixed | Stacked | Mixed | Stacked |
| Conversion | 13.2% | 12.3% | 14.0% | 13.5% | 14.6% | 14.2% |
| Carbon Monoxide (CO) | 82.2% | 88.0% | 71.2% | 78.7% | 63.9% | 70.2% |
| Dimethyl Ether ($CH_3OCH_3$) | 13.7% | 1.3% | 22.9% | 4.1% | 29.1% | 10.6% |
| Methanol ($CH_3OH$) | 4.1% | 1.4% | 5.9% | 2.6% | 7.0% | 4.4% |
| Totals HCs | <0.1% | 9.3% | <0.1% | 14.6% | <0.1% | 14.8% |
| $C_{4+}$ HCs | <0.1% | 8.7% | <0.1% | 13.8% | <0.1% | 13.9% |
| $C_{5+}$ HCs | <0.1% | 3.6% | <0.1% | 6.9% | <0.1% | 7.7% |

The stark contrast in hydrocarbon production from the two catalyst bed configurations is attributed to the kinetics of MeOH and DME production along the catalyst bed, and the subsequent effect on the rate of hydrocarbon pool chemistry in the Cu/BEA zeolite. In the mixed catalyst bed configuration, as the reaction mixture (i.e., $CO_2$+$H_2$) travels through the catalyst bed, the MeOH/DME product concentration increases gradually. DME concentration is expected to be low at the top of the catalyst bed, leading to slow initiation of the hydrocarbon pool chemistry over Cu/BEA, and thus, a low rate of hydrocarbon formation from Reaction 3. DME concentration is greater at the downstream section of the catalyst bed, however, only a small portion of the Cu/BEA catalyst remains in this section for conversion of DME to hydrocarbons. These phenomena combine to result in low overall $CO_2$ to hydrocarbon activity. In the stacked catalyst bed configuration, MeOH and DME concentration increased from zero in the first CZA+A bed, providing a greater concentration of oxygenates for reaction over the full portion of the downstream Cu/BEA catalyst. As a result, the bed-averaged hydrocarbon formation rate increased.

Figure 15A:
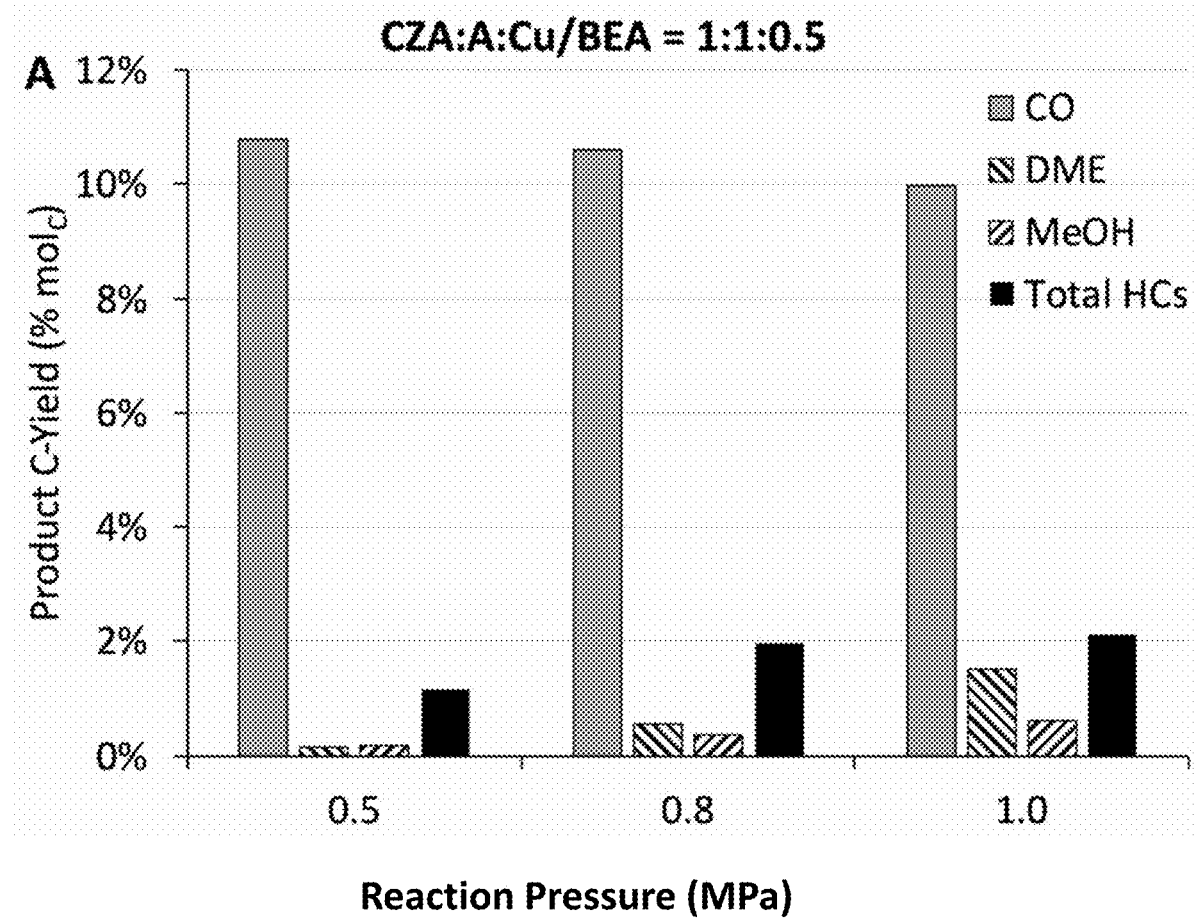
FIGS. 15A-15B illustrate product yields at different reaction pressures in $CO_2$ to hydrocarbons over stacked catalyst bed configurations using CZA:A:Cu/BEA catalysts having compositions of (A) 1:1:0.5 and (B) 1:1:1, according to some embodiments of the present disclosure. Reaction conditions were 220° C., $H_2$:$CO_2$ ratio of 3:1, and $SV_{CO2}$ of 1.5 $g_{CO2}$-$g_{CZA}^{-1}$-$h^{-1}$.
Figure 15B:
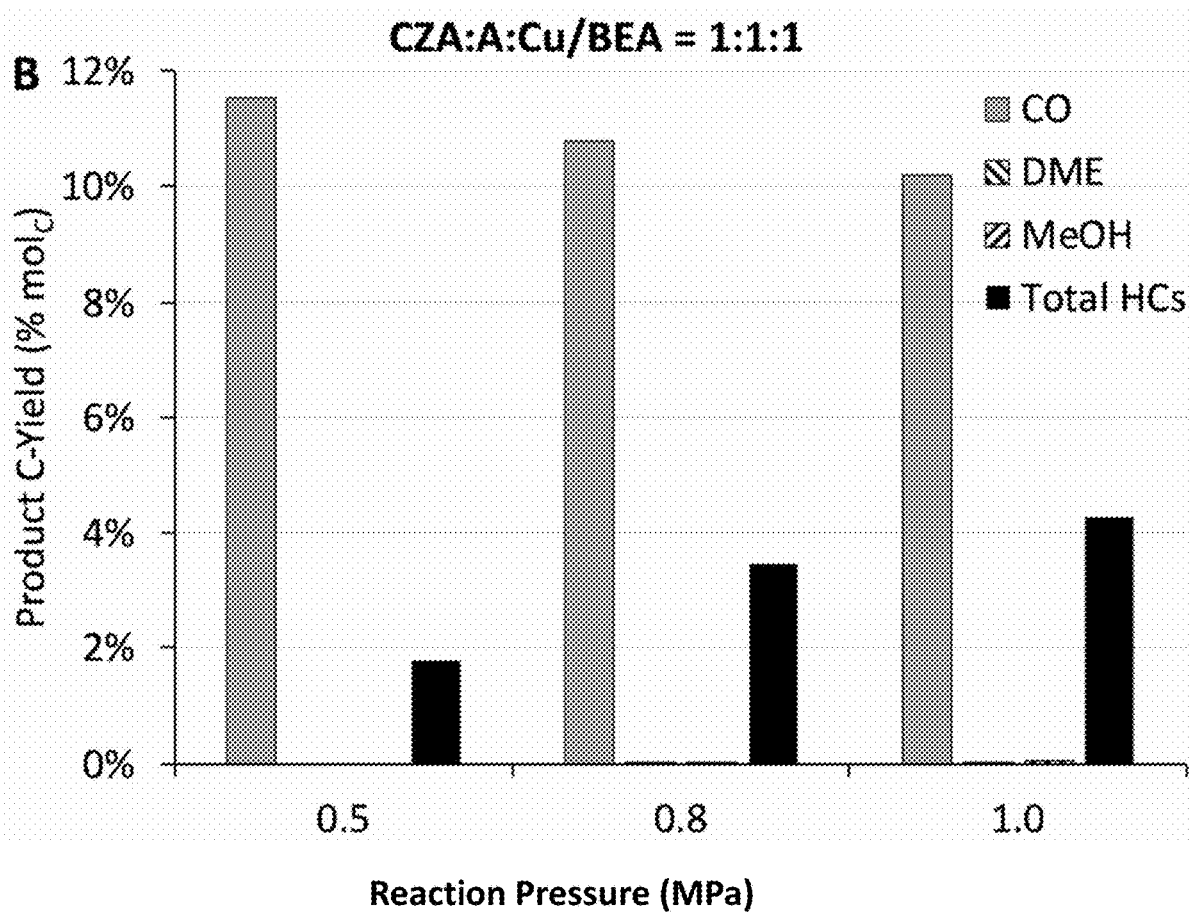

Increasing hydrocarbon yield from $CO_2$-Catalyst composition: As presented above, MeOH and DME were not fully consumed by the Cu/BEA catalyst in the initial experiments, potentially limiting the hydrocarbon yield. One approach to increase the conversion of the oxygenate intermediates is to increase the relative amount of the Cu/BEA catalyst. FIG. 15A presents product yields for the reaction at 220° C. and a pressure range of between 0.5 MPa and 1.0 MPa over a stacked catalyst bed with catalyst compositions for CZA:A: Cu/BEA of 1:1:0.5 and 1:1:1. Increased reaction pressure thermodynamically favors $CO_2$ hydrogenation to produce MeOH, which then initiates the sequential reactions to ultimately form hydrocarbons. Accordingly, the yield of MeOH, DME, and hydrocarbons increased with reaction pressure for both compositions (see FIGS. 15A and 15B). When the Cu/BEA content was doubled (see FIG. 15B), complete conversion of MeOH and DME was observed, and the yield of hydrocarbon products increased substantially at each investigated condition: increasing from 1.1 to 1.8% at 0.5 MPa, 2.0 to 3.5% at 0.8 MPa, and 2.1 to 4.4% at 1.0 MPa. For the 1:1:1 catalyst composition, CO-free selectivity to $C_{4+}$ hydrocarbons, which are the preferred HOG products, was over 94%. This high selectivity is unprecedented and advantageous for downstream separation, since CO can be easily separated and recycled to improve hydrocarbon production.

Figure 16A:
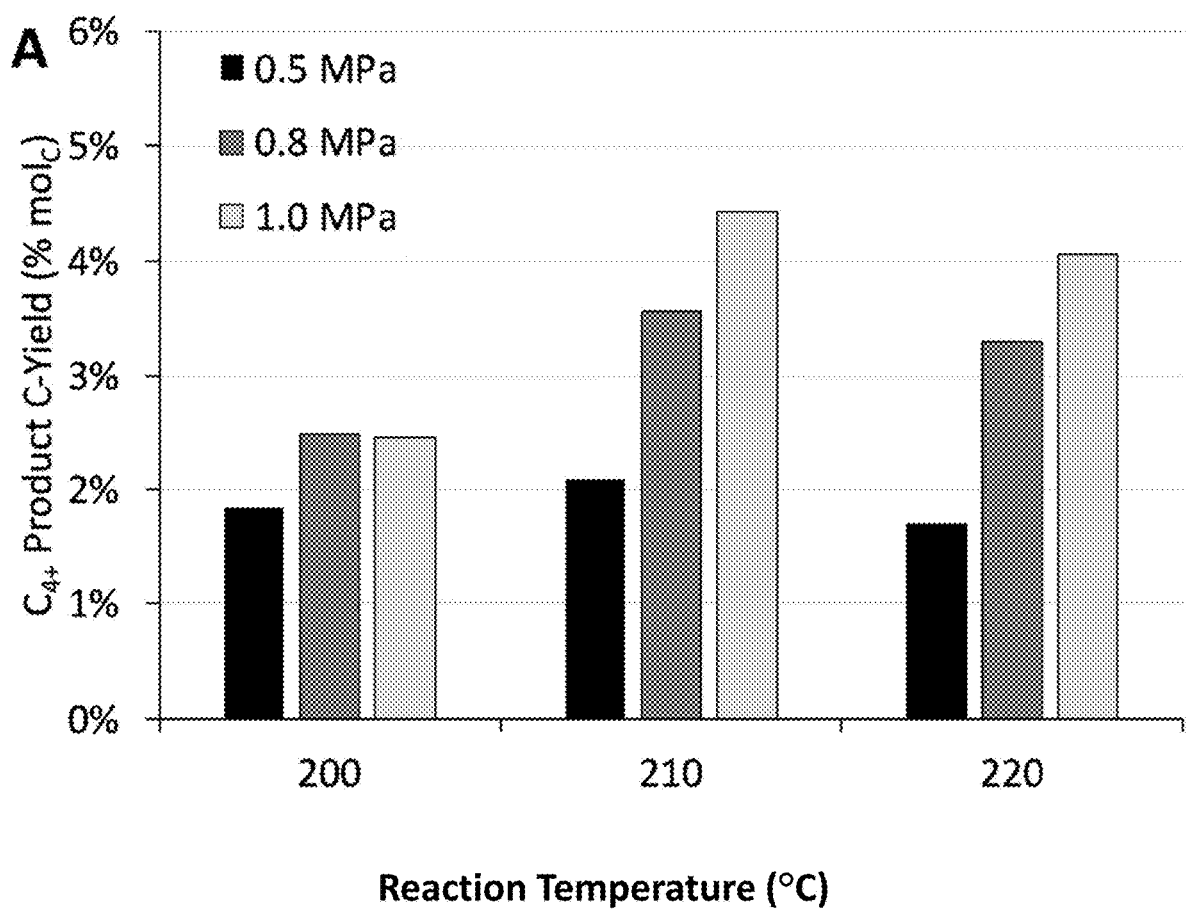
FIGS. 16A-16D illustrate the effect of reaction temperature and pressure on (A) $C_{4+}$ carbon yield, (B) MeOH and DME carbon yield, (C) CO-free $C_{4+}$ carbon selectivity, and (D) CO carbon yield over a stacked catalyst bed of CZA+A|Cu/BEA catalyst, according to some embodiments of the present disclosure. Reaction conditions were $H_2$:$CO_2$ ratio of 3:1, $SV_{CO2}$ of 1.5 $g_{CO2}$-$g_{CZA}^{-1}$-$h^{-1}$, and catalyst composition CZA:A:Cu/BEA of 1:1:1.
Figure 16B:
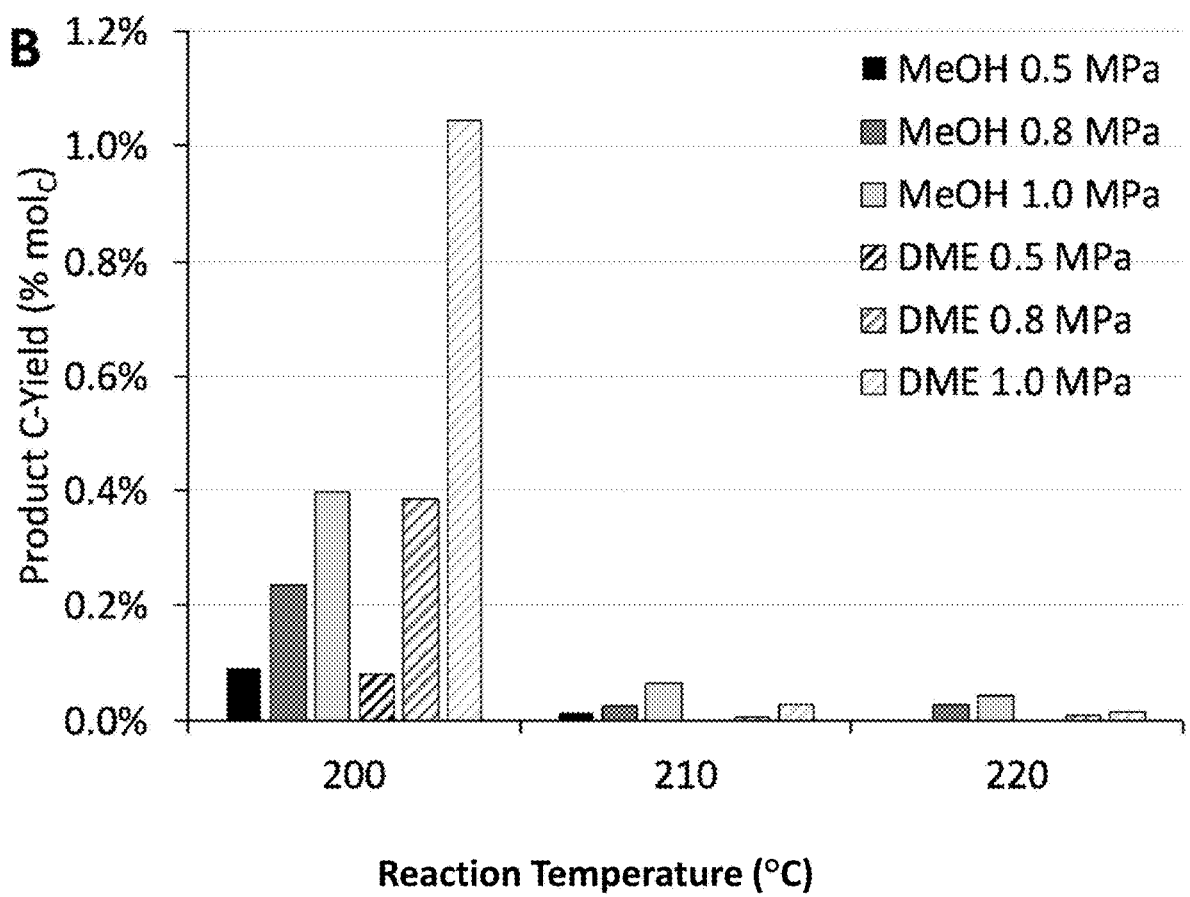
Figure 16C:
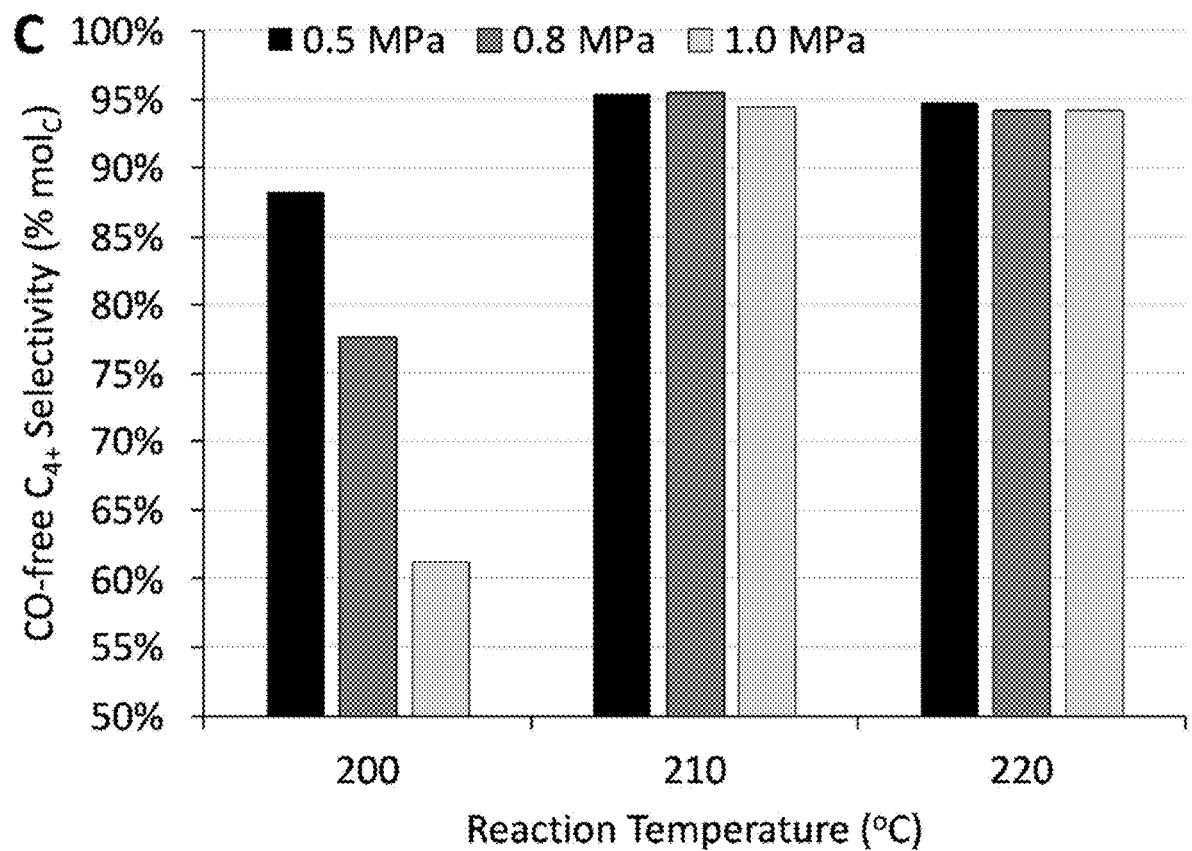
Figure 16D:
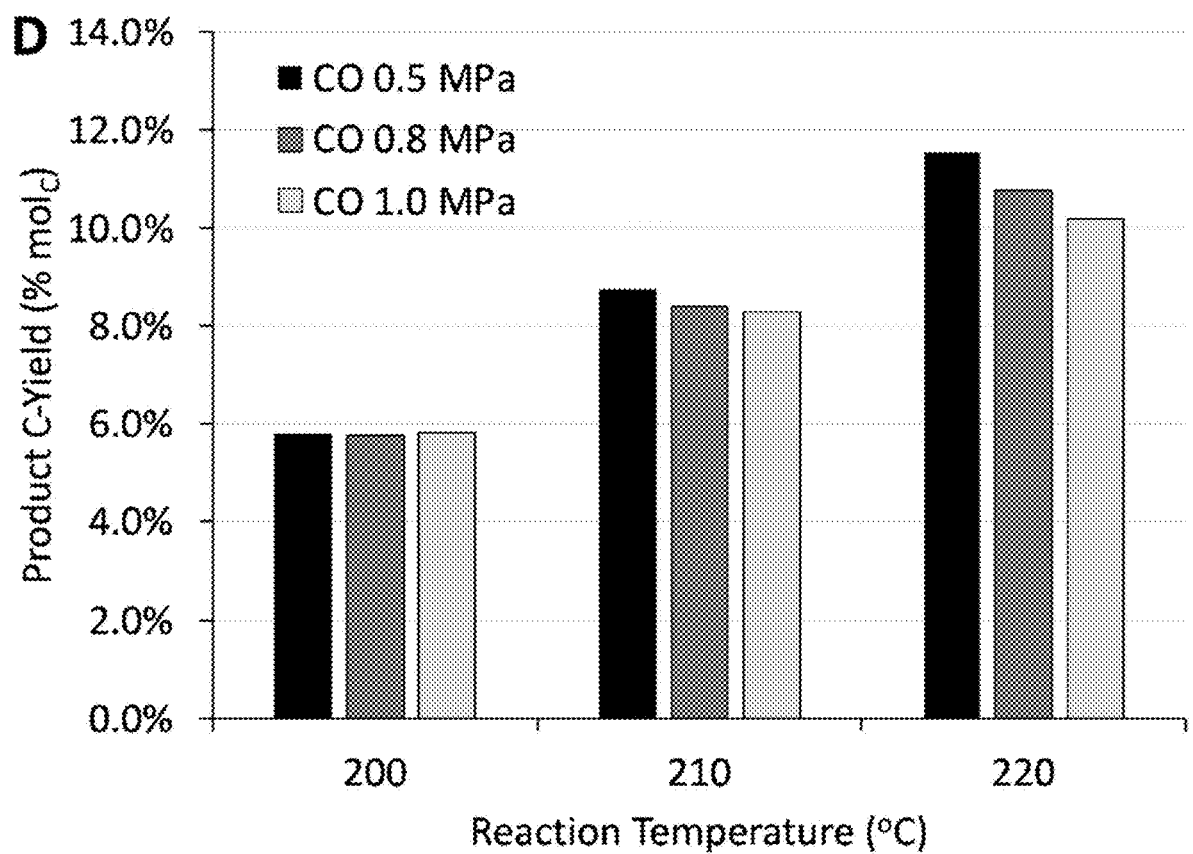

HOG yield in response to temperature and pressure: The effect of reaction temperature and pressure on yield and selectivity of desired $C_{4+}$ products were investigated towards increasing $C_{4+}$ production. Temperature and pressure strongly affect the thermodynamic equilibrium of MeOH synthesis, which ultimately affects hydrocarbon formation in the subsequent reactions. In general, increasing the reaction pressure increased $C_{4+}$ yield, attributed to the expected increase in MeOH and DME production with increasing pressure (see FIG. 16A). Varying the reaction temperature between 20° and 220° C. had mixed effects on $C_{4+}$ hydrocarbon yield (see FIG. 16A). At 200° C., MeOH and DME were not completely converted to hydrocarbons, especially at higher reaction pressure where a combined carbon yield of 1.4% was observed (see FIG. 16B). Increasing the reaction temperature to 210° C. greatly enhanced MeOH and DME conversion, resulting in increased $C_{4+}$ selectivity and yield (see FIG. 16C), even though CO formation was slightly more favored at 210° C. than 200° C. (see FIG. 16D). Further increasing the reaction temperature to 220° C. led to a decrease of both $C_{4+}$ selectivity and yield with a corresponding increase in CO yield.

Varying reaction temperature and pressure also affected the hydrocarbon product distribution over the stacked catalyst bed with a catalyst composition of CZA:A:Cu/BEA=1: 1:1. Across all conditions of temperature and pressure investigated here, the major hydrocarbon products were $C_4$ and $C_5$ species, consisting predominantly of isobutane and isopentane, respectively (see FIGS. 17A and 17B). In contrast to most reports of $CO_2$-to-hydrocarbon catalysis that focus on the production of $C_{2-3}$ olefins, light hydrocarbons (i.e., $C_{1-3}$) were a minor fraction of the hydrocarbon products from the stacked catalyst bed of CZA:A|Cu/BEA catalyst, accounting for less than 5% C-selectivity and comparable to the typical selectivity observed from DME-to-hydrocarbons over Cu/BEA. Low selectivity was also observed for $C_7$ products under these reaction conditions. Thus, the catalyst composition utilized here generates a unique product selectivity from $CO_2$ through MeOH/DME intermediates.

Figure 17A:
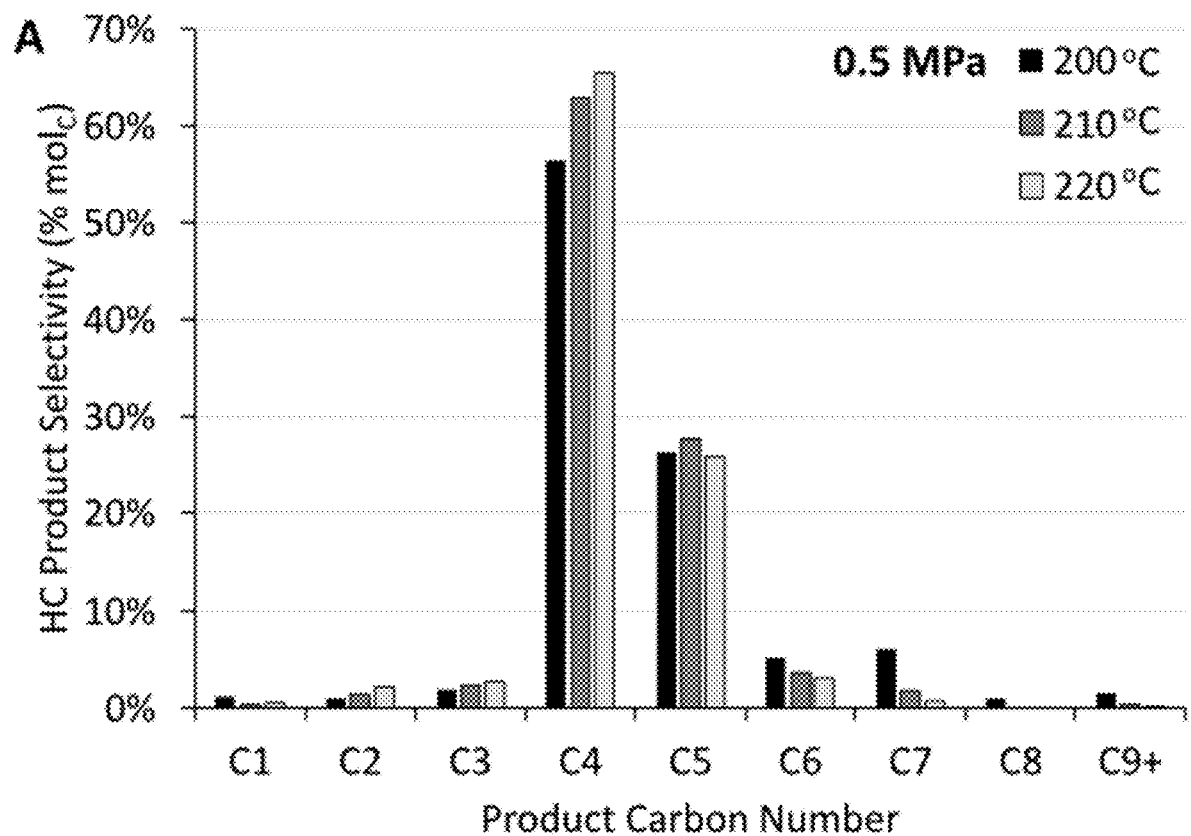
FIGS. 17A-17B illustrate a carbon number distribution of hydrocarbon products from $CO_2$ over a stacked catalyst bed of CZA+A|Cu/BEA catalyst at (A) 0.5 MPa with varying reaction temperature, and (B) 210° C. with varying reaction pressure, according to some embodiments of the present disclosure. Reaction conditions were $H_2$:$CO_2$ ratio of 3:1, $SV_{CO2}$ of 1.5 $g_{CO2}$-$g_{CZA}^{-1}$-$h^{-1}$, and catalyst composition CZA:A:Cu/BEA of 1:1:1.
Figure 17B:
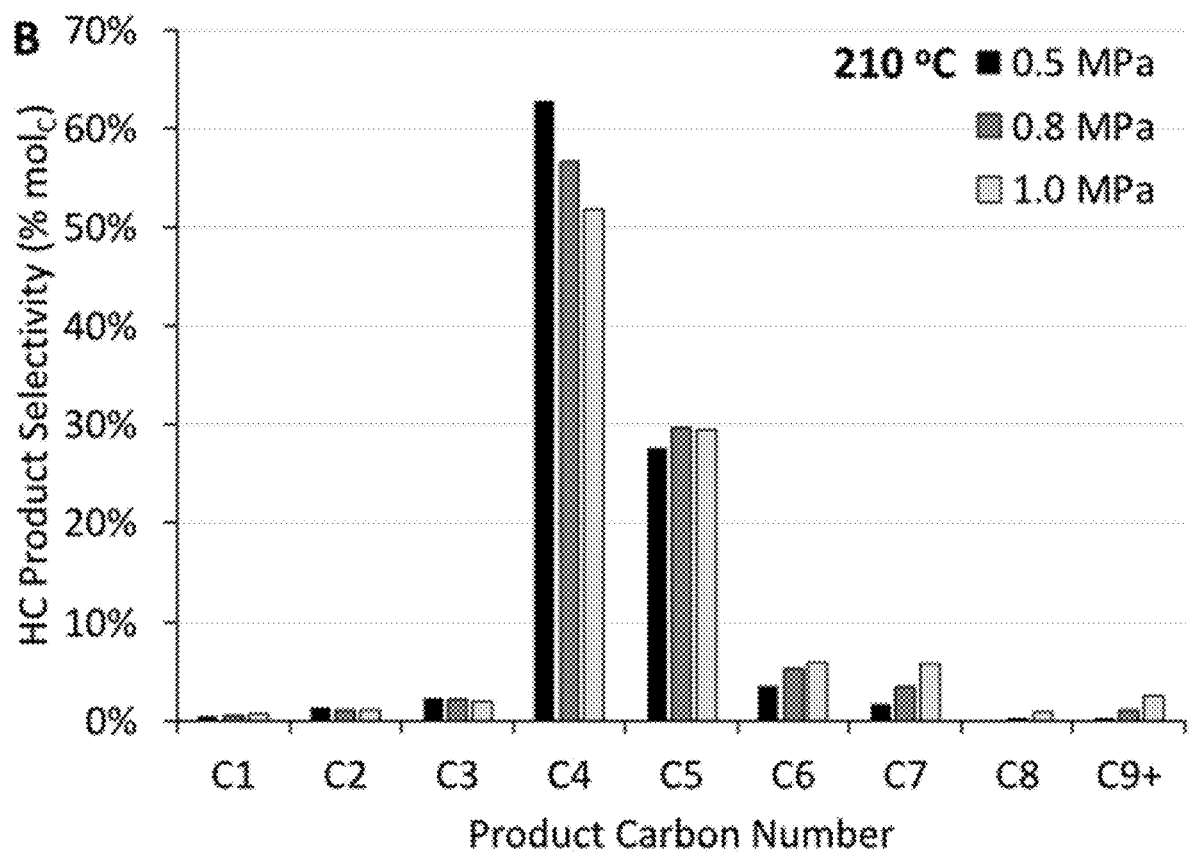

At a constant pressure of 0.5 MPa, increasing the reaction temperature from 200° C. to 220° C. resulted in greater selectivity to $C_{1-4}$ hydrocarbons, and an associated decrease in $C_{5+}$ product selectivity (see FIG. 17A). This shift in selectivity is attributed to increased cracking of $C_{5+}$ hydrocarbons in the Cu/BEA catalyst at higher temperatures. At a constant temperature of 210° C., increasing the reaction pressure from 0.5 to 1.0 MPa resulted in greater selectivity to $C_{5+}$ hydrocarbon products, with an associated decrease in $C_{1-4}$ selectivity (see FIG. 17B). This shift towards higher carbon number products at higher reaction pressure is attributed to greater conversion of MeOH and DME intermediates (as noted above), leading to enhanced methylation and chain growth of the hydrocarbon products.

The total hydrocarbon product included predominantly paraffins, with an olefin-to-paraffin ratio (O/P) less than 0.06 $mol_{C\text{-}olefin}/mol_{C\text{-}paraffin}$ for the variety of temperature and pressure conditions explored here. This is attributed to olefin hydrogenation under the high concentration of $H_2$ and in the presence of metallic Cu catalysts. The major products, $C_4$ and $C_5$ hydrocarbons, were essentially olefin-free. Ethylene and propylene were observed, attributed to cracking of long-chain hydrocarbons. Olefins in the $C_{6+}$ fraction were also observed, attributed to their participation in methylation and chain growth that ultimately results in heavier products.

Methods:

Materials: The baseline performance for the direct conversion of syngas to HOG was investigated utilizing mixed catalyst beds and stacked catalyst bed configurations containing three catalysts: (1) a commercially available Cu/ZnO/$Al_2O_3$ methanol synthesis catalyst (Megamax 800, Clariant, abbreviated "CZA"), (2) a γ-$Al_2O_3$ methanol dehydration catalyst (NorPro® SA6173, St. Gobain-Norpro, abbreviated "A"), and (3) a hydrocarbon synthesis catalyst. The hydrocarbon synthesis catalyst was either a beta zeolite (BEA; Tosoh) or a Cu-modified BEA zeolite (Cu/BEA). The CZA and A were used as received. BEA was obtained in ammonium form and had a $SiO_2$:$Al_2O_3$ ratio of 27. To achieve the proton form, BEA was calcined under flowing air at 550° C. Cu/BEA was synthesized from BEA via incipient wetness impregnation; an aqueous solution of Cu(NO$_3$)$_2$·2.5H$_2$O was added dropwise to NH$_4$-BEA until the incipient wetness point was reached, then the slurry was mixed and dried at 50° C. to yield Cu/BEA having ca. 4.5 wt % Cu. The Cu/BEA was calcined under flowing air at 550° C. prior to subsequent use.

Catalyst bed configurations: All catalysts were pressed (22 kN), crushed in a porcelain mortar and pestle, and sieved to 212-300 μm (50-70 mesh). In several cases, catalyst components were pressed, crushed and sieved together, and these are noted in brackets to indicate which species were processed together: [CZA+A] indicates Cu/ZnO/$Al_2O_3$ and γ-$Al_2O_3$ were pressed, crushed and sieved together. In other cases, catalyst components were pressed, crushed and sieved independently, and then physically mixed together and are notated without brackets: CZA+A indicates Cu/ZnO/$Al_2O_3$ and γ-$Al_2O_3$ were pressed, crushed and sieved to 212-300 μm independently, and then physically mixed together prior to loading in the reactor. The catalysts were loaded into a 7.9 mm ID stainless-steel tubular reactor, operating in top-down configuration, and positioned within the isothermal zone of an electric tube furnace using quartz chips and quartz wool. A four-point thermocouple positioned within the catalyst bed was used to monitor reaction temperatures. The reaction temperatures during an experiment were maintained within ±0.5° C. of the set point.

Catalyst mixtures were loaded into the reactor as either stacked catalyst beds or as mixed catalyst beds. For the stacked catalyst bed configuration, the top bed was separated from the bottom bed by a thin plug of quartz wool. For mixed catalyst beds, a single catalyst bed mixture was loaded. The vertical line symbol, |, is used to notate top and bottom beds, when a stacked catalyst bed configuration was used, where the first catalyst component(s) listed corresponds to top bed: CZA+A|Cu/BEA indicates a physical mixture of independently pressed, crushed and sieved CZA and A, loaded above a bed of Cu/BEA separated by a plug of quartz wool. The notation [CZA+A]|Cu/BEA would indicate a similar stacked catalyst bed configuration, with the CZA and A components pressed, crushed and sieved together. No attempt to directly measure homogeneity of mixed catalyst beds was made, although size- and shape-dependent settling differences were sought to be minimized by sieving all catalyst components to a consistent particle size range between 212 μm and 300 μm.

Reactions of syngas with or without co-fed $CO_2$: A constant total catalyst mass (CZA+A+Cu/BEA) of 3.75 g was used, regardless of the catalyst composition, which is defined as the relative mass loading of each component. Catalyst bed volumes ranged between 4.3 cm$^3$ and 4.6 cm$^3$. Catalyst mixtures were diluted with 3.6 g of low surface-area, inert silicon carbide to minimize channeling, axial dispersion, and temperature gradients in the bed. Catalyst compositions of CZA:A:Cu/BEA were 30:5:2, 32:5:4, 32:5:8, or 3:1:3. Catalyst compositions were selected in an attempt to balance DME formation rates observed in preliminary CZA+A experiments (data not shown), with the DME space velocity typically used in DME-to-hydrocarbons reactions (between 0.3 5 $g_{DME}\text{-}g_{Cu/BEA}$-h$^{-1}$ and 1.5 $g_{DME}\text{-}g_{Cu/BEA}$-h$^{-1}$). Prior to reaction testing, the catalyst was reduced at 230° C. under 25 sccm $H_2$ flow for 2 hours, initially heated from room temperature at a rate of 0.5° C.-min$^{-1}$. Syngas conversion experiments were performed at reactor temperatures between about 220° C. and about 320° C. Reaction pressure ranged from 430-5500 kPa absolute, the $H_2$:CO molar ratio was either 1 or 2 (mol-mol$^{-1}$) and the space velocity (SV) of CO was varied between 0.2 $g_{CO}\text{-}g_{CZA+A}^{-1}$-h$^{-1}$ and 1.0 $g_{CO}\text{-}g_{CZA+A}^{-1}$-h$^{-1}$, where $g_{CZA+A}$ is the combined mass of the CZA and A catalysts. When $CO_2$ was co-fed, the CO:$CO_2$ ratio was 1.1 or 2.8 (mol$_{CO}$-mol$_{CO2}^{-1}$). All volumetric flow rates are given at NTP (20° C., 101.3 kPa), and all pressures are absolute. The weight-hourly space velocity of CO (SV$_{CO}$) relative to the total mass loading of CZA+A was calculated with Equation 2:

$$SV_{CO} = \frac{\dot{n}_{CO,in}}{(m_{CZA} + m_A)} * MW_{CO} \qquad \text{Equation (2)}$$

where $\dot{n}_{CO,\,in}$ is the molar flow rate of CO into the reactor (mol-h$^{-1}$), MW$_{CO}$ is the molecular weight of CO (g-mol$^{-1}$) and m$_{CZA}$ and m$_A$ are the mass of CZA and A, respectively, loaded into the reactor.

The syngas mixture was prepared using $H_2$, CO, and Ar to generate a 49:49:2 molar ratio (equimolar $H_2$:CO ratio). To achieve greater $H_2$:CO ratios, 95% $H_2$/5% Ar was added using an independent mass flow controller. Mass flow controllers (Brooks Instrument) were used to control gas flow rates to the reactor system and were calibrated for the specific gas streams prior to use. Reactor pressure was maintained using a backpressure regulator and was monitored at the reactor inlet and outlet using pressure transducers.

Reactions of $CO_2$ without syngas: Catalyst compositions of CZA:A:Cu/BEA were between 1:1:0.5 and 1:1:1. Silicon carbide diluent was not used. A greater relative A-catalyst loading was employed to increase MeOH dehydration to DME (reaction 2), and therefore facilitate the conversion of $CO_2$ toward MeOH formation. A greater relative Cu/BEA loading was employed to increase DME and MeOH conversion to hydrocarbons. Prior to reaction testing, the catalyst was reduced at 230° C. under 50 sccm 95% H$_2$/5% Ar flow for 2 hours, initially heated from room temperature at a rate of 0.5° C.-min$^{-1}$. CO$_2$ conversion experiments were performed at reactor temperatures between about 200° C. and about 220° C. Reaction pressure was between about 0.5 MPa and about 1.0 MPa absolute. The feed gas composition of CO$_2$:H$_2$:Ar was 24:72:4, corresponding to an H$_2$:CO$_2$ molar ratio of three. The space velocity (SV) of CO$_2$ was set to about 0.75 g$_{CO2}$-g$_{CZA+A}$$^{-1}$-h$^{-1}$, where g$_{CZA+A}$ is the combined mass of the CZA and A catalysts. All volumetric flow rates are given at NTP (20° C., 101.3 kPa), and all pressures are absolute.

Equations for performance evaluation: Reactor inlet and outlet gases were sampled through heated (170-200° C.) lines using two Agilent 7890 GCs. One GC was equipped with a flame ionization detector (FID) to quantify light hydrocarbons (C$_{1-5}$) and two thermal conductivity detectors with argon and helium carrier gases to quantify inert and permanent gases. The second GC was fitted with two FIDs, one to quantify heavy hydrocarbons (C$_{5+}$) and the second to quantify oxygenates (MeOH, DME, methyl acetate). GC responses for reactants and products (hydrocarbons C$_1$-C$_4$ and all other products except H$_2$O) were calibrated using traceable gravimetric gas standards. For hydrocarbons C$_5$ or higher, GC responses for the respective detector were linearly extrapolated from the FID response of C$_1$-C$_4$ compounds.

Catalyst performance was evaluated from GC measurements using Ar as an internal standard. The net CO+CO$_2$ conversion, X$_{CO+CO2}$, was calculated with Equation 3:

$$X_{CO+CO2} = \frac{\dot{n}_{C,CO,in} - (\dot{n}_{C,CO,out} + \dot{n}_{C,CO2,out})}{\dot{n}_{C,CO,in}} * 100\% \quad (3)$$

where $\dot{n}_{C,CO,in}$, $\dot{n}_{c, CO, out}$, and $\dot{n}_{c, CO2, out}$ represent the molar flow rate of carbon in CO (mol$_C$-s$^{-1}$), in the inlet and effluent reactor streams, and the molar flow rate of carbon in effluent CO$_2$, respectively. This net CO+CO$_2$ conversion metric is used to quantify the amount of carbon converted to MeOH, DME, and hydrocarbons through the sequential reaction network, and incorporates the contribution from the WGSR.

The product carbon yield for various products, and product groupings (e.g., C4+. Hydrocarbons), was calculated with Equation 4:

$$Y_i = \frac{\dot{n}_{C,i,out}}{\dot{n}_{C,CO,in}} * 100\% \quad (4)$$

where $\dot{n}_{C,CO,in}$ is used as previously defined, and $\dot{n}_{C,i,out}$ is the molar flow rate of carbon in product(s) i. For example, yield to triptane (2,3,3-trimethylbutane) would use $\dot{n}_{C,triptane}$ for $\dot{n}_{C,i,out}$, the yield to C$_1$ oxygenates would use $\dot{n}_{c,MeOH}$+ $\dot{n}_{C,DME}$ for $\dot{n}_{C,i,out}$ and the yield to C$_{4+}$ hydrocarbons (i.e., HOG-range) was calculated with $\Sigma\dot{n}_{C,C4+}$, summed over all C$_4$-C$_9$ hydrocarbons, substituted for $\dot{n}_{C,i,out}$. No products of carbon number>9 were observed. Product-based conversion in CO$_2$ conversion experiments was calculated with Equation 5:

$$X_{CO2} = \frac{\Sigma\dot{n}_{C,i,out}}{\dot{n}_{C,CO2,in}} * 100\% \quad (5)$$

The product carbon selectivity, S$_i$ (in carbon %, noted as C-Selectivity), was calculated via Equation 6:

$$S_i = \frac{\dot{n}_{C,i,out}}{\Sigma\dot{n}_{C,i,out}} * 100\% \quad (6)$$

where $\dot{n}_{C,i,out}$ represents the effluent molar flow rate of carbon in product i (mol$_C$-s$^{-1}$), and may be summed over a group of desired products as exemplified for Y$_i$. The denominator term $\Sigma\dot{n}_{C,i}$ was summed over all products. The gravimetric activity of product(s), P$_i$ (g$_i$-g$_{cat}$$^{-1}$-h$^{-1}$), was calculated with Equation 7:

$$P_i = \frac{\dot{n}_i}{m_{cat}} * MW_i \quad (7)$$

where $\dot{n}_i$ is the molar flow rate of product i (mol-h$^{-1}$), MW$_i$ is the molecular weight of product i (g-mol$^{-1}$) and m$_{cat}$ is the mass of catalyst, either Cu/BEA or cumulative CZA+A mass. For grouped gravimetric activity metrics (e.g., C$_{4+}$ hydrocarbons), individual product P$_i$ values were summed.

The carbon balance was calculated, on the basis of amount of reactant carbon converted and amount of carbon observed in products, offering greater sensitivity to unquantified carbon than a balance performed on a total carbon basis due to incomplete reactant conversion. This carbon-converted balance was calculated with Equation 8:

$$\text{Carbon Converted Balance} = \frac{(\dot{n}_{C,CO,in} - \dot{n}_{C,CO,out}) - \Sigma\dot{n}_{C,i,out}}{(\dot{n}_{C,CO,in} - \dot{n}_{C,CO,out})} * 100\% \quad (8)$$

where $\dot{n}_{C,CO,in}$, $\dot{n}_{c, CO,out}$ are used as previously defined, and $\Sigma\dot{n}_{C,i,out}$ is the effluent molar flow rate of carbon in product i, summed over all products. A conventional carbon balance was calculated with Equation 9:

$$\text{Total Carbon Balance} = \frac{(\dot{n}_{C,i,in} - \dot{n}_{C,i,out})}{\dot{n}_{C,i,in}} * 100\% \quad (9)$$

where $\Sigma\dot{n}_{C,i,in}$ and $\Sigma\dot{n}_{C,i,out}$ are the summation, over all compounds i, of molar flow rate of carbon (mol$_C$-s$^{-1}$) in inlet and effluent streams, respectively.

METHOD EXAMPLES

Example 1. A method comprising: converting a gas stream comprising hydrogen (H$_2$) and carbon monoxide (CO) to a second mixture comprising a hydrocarbon having between 1 and 15 carbon atoms, wherein: the converting is performed using a first catalyst configured to convert H$_2$ and CO to methanol, a second catalyst configured to convert methanol to dimethyl ether (DME), and a third catalyst configured to convert DME to the hydrocarbon.

Example 2. The method of Example 1, wherein the H$_2$ and the CO are initially at a ratio between 1:1 and 4:1.

Example 3. The method of Example 2, wherein the ratio is between 1:1 and 3:1.

Example 4. The method of Example 1, wherein the first catalyst comprises copper and a zinc oxide.

Example 5. The method of Example 4, wherein the first catalyst further comprises at least one of silica, alumina, zirconia, or ceria.

Example 6. The method of Example 1, wherein the second catalyst comprises at least one of an alumina or silica.

Example 7. The method of Example 1, wherein the third catalyst comprises at least one of copper or a zeolite.

Example 8. The method of Example 7, wherein the zeolite comprises a beta zeolite having a silica to alumina ratio between about 20:1 and about 300:1.

Example 9. The method of Example 8, wherein the silica to alumina ratio is between about 25:1 and about 30:1.

Example 10. The method of Example 8, wherein the copper in the third catalyst is present at a concentration between about 1 wt % and about 20 wt %, relative to the total weight of the third catalyst.

Example 11. The method of Example 10, wherein copper in the third catalyst is present at a concentration between about 4 wt % and 10 wt %.

Example 12. The method of Example 1, wherein the first catalyst and the second catalyst are present at a ratio between about 1:1 and about 8:1.

Example 13. The method of Example 1, wherein the ratio of the first catalyst and the second catalyst is between about 1:1 and about 32:5.

Example 14. The method of Example 12, wherein the second catalyst and the third catalyst are present at a ratio between about 0.1:1 and about 5:2.

Example 15. The method of Example 1, wherein the first catalyst is positioned in a first zone, the second catalyst is positioned in a second zone, and the third catalyst is positioned in a third zone; and the first zone, the second zone and the third zone are all contained in a single reactor.

Example 16. The method of Example 15, wherein the single reactor is a packed bed.

Example 17. The method of Example 16, wherein: the first catalyst is positioned in the packed bed in a first layer, the second catalyst is positioned in the packed bed in a second layer, the third catalyst is positioned in the packed bed in a third layer, and the second layer is positioned in series between the first layer and the third layer.

Example 18. The method of Example 16, wherein: the first catalyst and the second catalyst are positioned in the packed bed as a well-mixed mixture in a first layer, the third catalyst is positioned in the packed bed in a second layer, and the first layer and the second layer are positioned in series.

Example 19. The method of Example 16, wherein the first catalyst, the second catalyst, and the third catalyst are positioned in the packed bed as a well-mixed mixture in a single layer.

Example 20. The method of Example 16, wherein: the first catalyst is positioned in the packed bed in a first layer, the second catalyst and the third catalyst are positioned in the packed bed as a well-mixed mixture in a second layer, and the first layer and the second layer are positioned in series.

Example 21. The method of Example 1, wherein: the first catalyst and the second catalyst are positioned in a first reactor; the third catalyst is positioned in a second reactor, and the first reactor and the second reactor are positioned in series.

Example 22. The method of Example 21, wherein the first catalyst and second catalyst are positioned in a packed bed as a well-mixed mixture.

Example 23. The method of Example 21, wherein the first reactor is maintained at a temperature between about 180° C. and about 320° C.

Example 24. The method of Example 23, wherein the temperature is between about 200 and 250° C.

Example 25. The method of Example 21, wherein the second reactor is maintained at a temperature between about 180° C. and about 320° C.

Example 26. The method of Example 25, wherein the temperature of the second reactor is maintained between about 200° C. and 320° C.

Example 27. The method of Example 21, wherein the first reactor is a packed bed.

Example 28. The method of Example 21, wherein the second reactor is a packed bed.

Example 29. The method of Example 21, wherein the first reactor is maintained at a pressure between about 300 kPa and about 10.0 MPa.

Example 30. The method of Example 29, wherein the pressure of the first reactor is maintained between about 400 kPa and 5.5 MPa.

Example 31. The method of Example 1, wherein the CO is provided at a flow rate resulting in a space velocity between about 0.2 g/g hr and about 1.0 g/g hr.

Example 32. The method of Example 1, wherein the gas stream further comprises carbon dioxide.

Example 33. The method of Example 32, wherein the gas stream has a concentration of carbon dioxide greater than or equal to 10 wt %.

COMPOSITION EXAMPLES

Example 1. A composition comprising: a first portion comprising copper and a zinc oxide; a second portion comprising at least one of an alumina or silica; and a third portion comprising a zeolite.

Example 2. The composition of Example 1, wherein the first portion further comprises at least one of silica, alumina, zirconia, or ceria.

Example 3. The composition of Example 1, wherein the third portion further comprises copper.

Example 4. The composition of Example 1, wherein the zeolite comprises a beta zeolite having a silica to alumina ratio between about 20:1 and about 300:1.

Example 5. The composition of Example 4, wherein the silica to alumina ratio is between of about 25:1 and 30:1.

Example 6. The composition of Example 3, wherein the copper of the third portion is present at a concentration between about 1 wt % and about 20 wt %, relative to the total weight of the third portion.

Example 7. The composition of Example 6, wherein the copper of the third portion is present at a concentration between about 4 wt % and 10 wt %.

Example 8. The composition of Example 1, wherein the first portion and the second portion are present at a ratio between about 1:1 and about 8:1.

Example 9. The composition of Example 1, wherein the ratio of the first portion and the second portion is between about 0.1:1 and 32:5.

Example 10. The composition of Example 8, wherein the second portion and the third portion are present at a ratio between about 0.1:1 and about 5:2.

Example 11. The composition of Example 1, wherein the first portion, the second portion, and the third portion are thoroughly mixed into a single mixture.

Example 12. The composition of Example 1, wherein: the first portion is in a first layer, the second layer is in a second layer, the third layer is in a third layer, and the second layer is positioned between the first layer and the third layer.

SYSTEM EXAMPLE

Example 1. A system comprising: at least one of a first reactor or a second reactor, wherein: at least one of the first reactor or the second reactor contains a catalyst or composition as described herein.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. While certain aspects of conventional technology have been discussed to facilitate disclosure of some embodiments of the present invention, the Applicants in no way disclaim these technical aspects, and it is contemplated that the claimed invention may encompass one or more of the conventional technical aspects discussed herein. Thus, the following claims are hereby incorporated into this Detailed Description, with each claim standing on its own as a separate aspect, embodiment, or configuration.

What is claimed is:

1. A method comprising:
    converting a gas stream comprising hydrogen ($H_2$) and carbon monoxide (CO) to a mixture comprising a hydrocarbon having between 3 and 15 carbon atoms, wherein:
    the converting is performed using a first catalyst configured to convert $H_2$ and CO to methanol, a second catalyst configured to convert methanol to dimethyl ether (DME), and a third catalyst configured to convert DME to the hydrocarbon;
    the first catalyst and the second catalyst are physically mixed in a first catalyst bed and the third catalyst is positioned in a second catalyst bed;
    the first catalyst bed and second catalyst bed are contained in a single stacked packed-bed reactor in series;
    the first catalyst comprises copper-zinc oxide-alumina (CZA);
    the second catalyst comprises gamma alumina (A); and
    the third catalyst comprises copper modified BEA zeolite (Cu/BEA).

2. The method of claim 1, wherein the Cu/BEA catalyst comprises a beta zeolite having a silica to alumina ratio between about 20:1 and about 300:1.

3. The method of claim 2, wherein the copper in the third catalyst is present at a concentration between about 1 wt % and about 20 wt %, relative to the total weight of the third catalyst.

4. The method of claim 1, wherein the first catalyst and the second catalyst are present at a ratio between about 1:1 and about 8:1.

5. The method of claim 4, wherein the second catalyst and the third catalyst are present at a ratio between about 0.1:1 and about 5:2.

6. The method of claim 1, wherein the gas stream further comprises carbon dioxide ($CO_2$).

7. The method of claim 6, wherein the gas stream has a concentration of carbon dioxide greater than or equal to 10 mol %.

* * * * *